(12) United States Patent
Alvizo et al.

(10) Patent No.: US 12,031,159 B2
(45) Date of Patent: *Jul. 9, 2024

(54) KETOREDUCTASE POLYPEPTIDES FOR THE PREPARATION OF PHENYLEPHRINE

(71) Applicant: Codexis, Inc., Redwood City, CA (US)

(72) Inventors: Oscar Alvizo, Fremont, CA (US); Steven J. Collier, Concord, MA (US); Hans-Georg Joerg Hennemann, Bedburg (DE); Seong Ho Oh, Singapore (SG); Wenjuan Zha, Singapore (SG)

(73) Assignee: Codexis, Inc., Redwood City, CA (US)

( * ) Notice: Subject to any disclaimer, the term of this patent is extended or adjusted under 35 U.S.C. 154(b) by 124 days.

This patent is subject to a terminal disclaimer.

(21) Appl. No.: 17/731,635

(22) Filed: Apr. 28, 2022

(65) Prior Publication Data

US 2022/0267744 A1    Aug. 25, 2022

Related U.S. Application Data

(60) Continuation of application No. 17/085,783, filed on Oct. 30, 2020, now Pat. No. 11,345,898, which is a continuation of application No. 16/778,368, filed on Jan. 31, 2020, now Pat. No. 10,870,835, which is a continuation of application No. 16/437,354, filed on Jun. 11, 2019, now Pat. No. 10,590,396, which is a continuation of application No. 15/812,628, filed on Nov. 14, 2017, now Pat. No. 10,358,631, which is a continuation of application No. 14/755,056, filed on Jun. 30, 2015, now Pat. No. 9,834,758, which is a division of application No. 13/390,677, filed as application No. PCT/US2010/046020 on Aug. 19, 2010, now Pat. No. 9,102,959.

(60) Provisional application No. 61/235,324, filed on Aug. 19, 2009.

(51) Int. Cl.
*A61K 31/137* (2006.01)
*C12N 9/04* (2006.01)
*C12P 13/00* (2006.01)

(52) U.S. Cl.
CPC .......... *C12N 9/0006* (2013.01); *A61K 31/137* (2013.01); *C12P 13/001* (2013.01); *C12Y 101/01184* (2013.01)

(58) Field of Classification Search
CPC ............................. C12P 13/001; A61K 31/137
See application file for complete search history.

(56) References Cited

U.S. PATENT DOCUMENTS

| | | |
|---|---|---|
| 5,064,761 A | 11/1991 | Schneider et al. |
| 5,200,335 A | 4/1993 | Hummel et al. |
| 5,225,339 A | 7/1993 | Wong et al. |
| 5,342,767 A | 8/1994 | Wong et al. |
| 5,385,833 A | 1/1995 | Bradshaw et al. |
| 5,427,933 A | 6/1995 | Chen et al. |
| 5,491,077 A | 2/1996 | Chartrain et al. |
| 5,538,867 A | 7/1996 | Durliat et al. |
| 5,559,030 A | 9/1996 | Matsuyama et al. |
| 5,618,707 A | 4/1997 | Homann et al. |
| 5,700,670 A | 12/1997 | Yamagishi et al. |
| 5,712,388 A | 1/1998 | Matsumoto et al. |
| 5,767,115 A | 6/1998 | Rosenblum et al. |
| 5,891,685 A | 4/1999 | Yamagishi et al. |
| 5,891,703 A | 4/1999 | Van Der Laan et al. |
| 6,033,823 A | 3/2000 | Van Der Laan et al. |
| 6,037,158 A | 3/2000 | Hummel et al. |
| 6,117,679 A | 9/2000 | Stemmer |
| 6,207,822 B1 | 3/2001 | Thiruvengadam et al. |
| 6,225,099 B1 | 5/2001 | Hummel et al. |
| 6,376,246 B1 | 4/2002 | Crameri et al. |
| 6,399,339 B1 | 6/2002 | Wolberg et al. |
| 6,413,750 B1 | 7/2002 | Hummel et al. |
| 6,495,023 B1 | 12/2002 | Zeikus et al. |
| 6,586,182 B1 | 7/2003 | Patten et al. |
| 6,627,757 B2 | 9/2003 | Fu et al. |
| 6,645,746 B1 | 11/2003 | Kizaki et al. |
| 6,800,477 B2 | 10/2004 | Patel et al. |
| 7,067,675 B2 | 6/2006 | Reddy et al. |
| 7,083,962 B2 | 8/2006 | Kimoto et al. |
| 9,102,959 B2 | 8/2015 | Alvizo et al. |
| 9,834,758 B2 * | 12/2017 | Alvizo .................. C12P 13/001 |
| 10,358,631 B2 * | 7/2019 | Alvizo ........... C12Y 101/01184 |
| 10,590,396 B2 * | 3/2020 | Alvizo ........... C12Y 101/01184 |
| 10,870,835 B2 * | 12/2020 | Alvizo ................. A61K 31/137 |
| 11,345,898 B2 * | 5/2022 | Alvizo ........... C12Y 101/01184 |
| 2002/0061564 A1 | 5/2002 | Rozzell |
| 2003/0054520 A1 | 3/2003 | Bommanus et al. |
| 2003/0068811 A1 | 4/2003 | Patel et al. |

(Continued)

FOREIGN PATENT DOCUMENTS

| | | |
|---|---|---|
| EP | 0369691 B1 | 7/1994 |
| EP | 1 013 758 A1 | 6/2000 |

(Continued)

OTHER PUBLICATIONS

Amidjojo et al., 2005, "Asymmetric Synthesis of Tert-butyl (3R, 5S)6-chloro-dihydroxyhexanoate with *Lactobacillus kefir*," *Appl Microbiol Biotechnol.*, 69:9-15.

(Continued)

*Primary Examiner* — Tekchand Saidha

(74) *Attorney, Agent, or Firm* — Codexis, Inc.

(57) ABSTRACT

The disclosure relates to engineered ketoreductase polypeptides and processes of using the polypeptides for production of phenylephrine.

14 Claims, 1 Drawing Sheet

Specification includes a Sequence Listing.

(56) References Cited

U.S. PATENT DOCUMENTS

| | | |
|---|---|---|
| 2004/0214297 A1 | 10/2004 | Davis et al. |
| 2004/0265978 A1 | 12/2004 | Gupta et al. |
| 2005/0095619 A1 | 5/2005 | Davis et al. |
| 2005/0124029 A1 | 6/2005 | Van Der Laan et al. |
| 2006/0195947 A1 | 8/2006 | Davis et al. |
| 2006/0286646 A1 | 12/2006 | Patel et al. |
| 2007/0083055 A1 | 4/2007 | Sturmer et al. |
| 2007/0243594 A1 | 10/2007 | Gupta et al. |
| 2008/0220990 A1 | 9/2008 | Fox |
| 2008/0248539 A1 | 10/2008 | Giver et al. |
| 2008/0318295 A1 | 12/2008 | Ching et al. |
| 2009/0093031 A1 | 4/2009 | Liang et al. |
| 2009/0104671 A1 | 4/2009 | Yasohara et al. |
| 2009/0155863 A1 | 6/2009 | Liang et al. |
| 2009/0162909 A1 | 6/2009 | Campopiano et al. |
| 2009/0191605 A1 | 7/2009 | Liang et al. |
| 2009/0311762 A1 | 12/2009 | Tschentscher et al. |
| 2009/0312196 A1 | 12/2009 | Colbeck et al. |
| 2010/0062499 A1 | 3/2010 | Mundorff et al. |
| 2011/0171700 A1 | 7/2011 | Breuer et al. |

FOREIGN PATENT DOCUMENTS

| | | | |
|---|---|---|---|
| EP | 1176203 A1 | | 1/2002 |
| EP | 1 179 595 A1 | | 2/2002 |
| EP | 1908845 A1 | | 4/2008 |
| WO | WO 1995/22625 | | 8/1995 |
| WO | WO 1997/20078 | | 6/1997 |
| WO | WO 1997/35966 | | 10/1997 |
| WO | WO 1998/27230 | | 6/1998 |
| WO | WO 2000/42651 | | 7/2000 |
| WO | WO 2001/040450 A1 | | 6/2001 |
| WO | WO 2001/075767 A2 | | 10/2001 |
| WO | WO 2002/086126 A2 | | 10/2002 |
| WO | WO 2005/017135 A1 | | 2/2005 |
| WO | WO 2005/018579 A2 | | 3/2005 |
| WO | WO 2005/033094 A2 | | 4/2005 |
| WO | WO 2005/054491 A1 | | 6/2005 |
| WO | 2005/077171 A1 | | 8/2005 |
| WO | WO 2007/010944 A1 | | 1/2007 |
| WO | WO 2007/012428 A1 | | 2/2007 |
| WO | WO 2008/042876 A2 | | 4/2008 |
| WO | WO 2008/103248 A1 | | 8/2008 |
| WO | 2009/036404 A2 | | 3/2009 |
| WO | WO 2009/086283 A1 | | 7/2009 |
| WO | WO 2010/031776 A2 | | 3/2010 |

OTHER PUBLICATIONS

Baerga-Ortiz et al., 2006, "Directed Mutagenesis Alters the Stereochemistry of Catalysis by Isolated Ketoreductase Domains from the Erythromycin Polyketide Synthase," *Chem Biol.*, 13(3):277-85.
Bisel et al., 2007, "Stereochemical clarification of the enzyme-catalysed reduction of 2-acetylchromen-4-one," *Tetrahedron Asymmetry*, 18(9):1142-1144.
Bradshaw et al., 1992, "*Lactobacillus kefir* Alcohol Dehydrogenase: A Useful Catalyst for Synthesis," *J. Org. Chem.* 57(5):1532-1536.
Breyer-Pfaff et al., 1999, "High-affinity Stereoselective Reduction of the Enantiomers of Ketotifen and of Ketonic Nortriptyline Metabolites by Aldo-Keto Reductases from Human Liver," *Biochem. Pharmacol.*, 59:249-260.
Cha et al., 2002, "Stereochemical control in diastereoselective reduction of α-substituted-β-ketoesters using a reductase purified from *Kluyveromyces marxianus*," *Biotechnol. Lett* , 24:1695-1698.
Daussmann et al., 2006, "Oxidoreductases and Hydroxynitrilase Lyases: Complementary Enzymatic Technologies for Chiral Alcohols," *Eng Life Sci.*, 6(2):125-129.
Fuganti et al., 1993, "Microbial Generation of (2R,3S)- and (2S,3S)-Ethyl 2-Benzamidomethyl-3-hydroxybutyrate, a Key Intermediate in the Synthesis of (3S,1'R)-3-(1'-Hydroxyethyl)azetidin-2-one," *J Chem. Soc. Perkin Trans.* 1:2247-2249.
Genbank Accession No. 1NXQ_A dated Sep. 24, 2008.
Genbank Accession No. AB036927 dated Feb. 2, 2001.
Genbank Accession No. ABJ63353.1 dated Mar. 5, 2010.
Genbank Accession No. AJ544275 dated Feb. 5, 2010.
Genbank Accession No. AAN73270 dated Nov. 3, 2003.
Genbank Accession No. AAP94029 dated Apr. 1, 2004.
Genbank Accession No. AF160799 dated Dec. 9, 1999.
Genbank Accession No. BAA24528.1 dated Jan. 28, 1998.
Genbank Accession No. CAD66648 dated Feb. 5, 2010.
Genbank Accession No. CP00046 dated Mar. 5, 2010.
Genbank Accession No. JC7338 dated Jun. 3, 2002.
Genbank Accession No. NP011476 dated May 17, 2010.
Genbank Accession No. NP010656.1 dated May 17, 2010.
Genbank Accession No. NP010159.1 dated May 17, 2010.
Genbank Accession No. NP014490.1 dated May 17, 2010.
Genbank Accession No. NP631415.1 dated Mar. 30, 2010.
Genbank Accession No. P41747 dated Apr. 20, 2010.
Genbank Accession No. Q07551 dated Apr. 20, 2010.
Genbank Accession No. Q9UUN9 dated Mar. 2, 2010.
Genbank Accession No. X64841.1 dated Jan. 8, 1997.
Genbank Accession No. ZP00318704.1 dated Jun. 17, 2004.
Genbank Accession No. ZP00202558.1 dated Oct. 4, 2004.
Goldberg et al., 2007, "Biocatalytic ketone reduction—a powerful tool for the production of chiral alcohols—part I: processes with isolated enzymes," *Appl Microbiol Biotechnol*, 76(2):237-248.
Gröger et al., 2004, "Preparative asymmetric reduction of ketones in a biphasic medium with an (S)-alcohol dehydrogenase under in situ-cofactor-recycling with a formate dehydrogenase," *Tetrahedron* 60:633-640.
Hönig et al., 1994, "Enzymatic Resolutions of Heterocyclic Alcohols," *Biocatalysis* 9:61-69.
Hummel et al., 1989, "Dehydrogenases for the synthesis of chiral compounds," *Eur. J. Biochem.* 184:1-13.
Hummel, 1990, "Reduction of acetophenone to R(+)-phenylethanol by a new alcohol dehydrogenase from *Lactobacillus kefir*," *Appl Microbiol Biotechnol*, 34(1):15-19.
Hummel, 1999, "Large-scale applications of NAD(P)-dependent oxidoreductases: recent developments," *Trends Biotechnol.* 17(12):487-492.
Jörnvall et al., 1995, "Short-chain dehydrogenase/reductases (SDR)," *Biochemistry* 34(18):6003-6013.
Kallberg et al., 2002, "Short-chain dehydrogenase/reductase (SDR) relationships: A large family with eight clusters common to human, animal, and plant genomes," *Protein Sci.* 11(3):636-641.
Kallberg et al., 2002, "Short-chain dehydrogenases/reductases (SDRs) Coenzyme-based functional assignments in completed genomes," *Eur. J. Biochem.* 269:4409-4417.
Kaluzna et al., 2005, "Ketoreductases: stereoselective catalysts for the facile synthesis of chiral alcohols," Tetrahedron: Asymmetry 16: 3682-3689.
Kataoka et al., 2003, "Novel bioreduction system for the production of chiral alcohols," Appl Microbiol Biotechnol 62:437-445.
Nakamura et al. 2003, "Recent developments in asymmetric reduction of ketones with biocatalysts," Tetrahedron: *Asymmetry* 14: 2659-2681.
Neifind et al., 2000, "Crystallization and preliminary characterization of crystals of R-alcohol dehydrogenase from lactobacillus brevis," *Acta Crystallogr. D. Biol. Crystallogr.* 56:1696-1698.
Niefind et al., 2003, "The Crystal Structure of R-specific Alcohol Dehydrogenase from *Lactobacillus brevis* Suggests the Structural Basis of its Metal Dependency," *J Mol Bio.* 327(2):317-28.
Petrash et al., 2001, "Functional Genomic Studies of Aldo-keto Reductases," *Chem Biol Interact.*, 130-132(1-3):673-83.
Rodrigues et al., 2004, "Recent Advances in the Biocatalytic Asymmetric Reduction of Acetophenones and α,β-Unsaturated Carbonyl Compounds," *Food Technol. Biotechnol.* 42 (4) 295-303.
Santaniello et al., 1984, "Chiral Synthesis of a Component of Amanita muscaria, (−)-4-hydroxypyrrolidin-2-one, and Assessment of its Absolute Configuration," *J. Chem. Res.*, Synop., 132-133.
Schlieben et al., 2005, "Atomic Resolution Structures of R-specific Alcohol Dehydrogenase from *Lactobacillus brevis* Provide the Structural Bases of its Substrate and Cosubstrate Specificity," *J. Mol. Biol.* 349(4):801-13.

(56) References Cited

OTHER PUBLICATIONS

Stemmer et al., 1994, "DNA shuffling by random fragmentation and reassembly: in vitro recombination for molecular evolution," *Prod. Natl. Acad. Sci.USA* 91:10747-10751.
Sulzenbacher et al., 2004, "Crystal Structure of *E. coli* Alcohol Dehydrogenase YqhD: Evidence of a Covalently Modified NADP Coenzyme," *Journal Mol. Biol.* 342:489-502.
Temino et al., 2005, "Entrapment of the alcohol dehydrogenase from *Lactobacillus kefir* in polyvinyl alcohol for the synthesis of chiral hydrophobic alcohols in organic solvents," *Enzyme Microb. Technol.*, 36(1):3-9.
Weckbecker et al., 2006, "Cloning, expression, and characterization of an (R)-specific alcohol dehydrogenase from *Lactobacillus kefir*," *Biocatal. Biotransform.*, 24(5):380-389.
Wolberg et al., 2000, "Highly Regio- and Enantioselective Reduction of 3,5-Dioxocarboxylates," *Angew Chem. Int. Ed. Engl.* 39(23):4306-4308.
Wolberg, 2001, "Enzymatic Reduction of Hydrophobic beta, delta-Diketo Esters," *Synthesis* 937-942.
Xie et al., 2006, "Asymmetric Reduction of o-Chloroacetophenone with *Candida pseudotropicalis* 104," *Biotechnol. Prog.* 22:1301-1304.
Zhao et al., 1999, "Molecular evolution by staggered extension process (StEP) in vitro recombination," *Nature Biotech.* 16:258.
Zhu et al., 2005, "Evaluation of substituent effects on activity and enantioselectivity in the enzymatic reduction of aryl ketones," *Tetrahedron Asymm.* 16:1541-1546.
International Search Report of the International Searching Authority of PCT/US2010/046020 mailed May 27, 2011.
Broussy et al., 2009, Enantioselective, ketoreductase-based intry into pharmaceutical building blocks: ethanol as tunable nicotinamid reductant: *Organic Ltrs*, vol. 11(2), 305-308.
Sorgedrager et al., 2008, "Asymetric carbonyl reductions with microbial ketoreductases," *Adv. Synthesis and Cataly.* 350:14-15, 2322-2328.
Makino et al., 2007, "Engineering the phenylacetaldehyde reductase mutant for improved substrate conversion in the presence of concentrated 2-propanol," *Appl. Microbiol. Biotechnol.* 78:833-843.
Stampfer et al., 2002, "Biocatalytic asymmetric hydrogen Transfer," *Angew.Chem. Intl. Ed.* 41:6 1014-1017.
Yamada-Onodera et al., 2007, "Purification and Characterization of 2-Aminoacetophenone Reductase of Newly Isolated *Burkholderia* sp. YT" *Journal Biosci and Bioeng.* vol. 104:5 416-419.
Supplementary European Search Report dated Feb. 12, 2013.
Guo, H.H. et al., "Protein tolerance to random amino acid change," PNAS, 101(25):9205-9210 [2004].
Lazar, E., et al., "Transforming Growth Factor ox: Mutation of Aspartic Acid 47 and Leucine 48 Results in Different Biological Activities," Molecular and Cellular Biology, 8(3):1247-1252 [1988].
Hill, M.A., et al., "Functional Analysis of Conserved Histidines in ADP-Glucose Pyrophosphorylase from *Escherichia coli*," Biocm. Biophys. Res. Comm., 244(2):573-577 [1998].
Branden, C., et al., Introduction to Protein Structure, 2nd edition, Garland Science Publisher, pp. 3-12 [1999].
Wacey, A.I., et al., "Disentangling the perturbational effects of amino acid substitutions in the DNA-binding domain of p53," Hum. Genet., 104:15-22 [1999].
Genpept Accession No. WP_035452557.1 dated Dec. 23, 2014.
Genpept Accession No. WP054768785.1 dated Oct. 31, 2016.

* cited by examiner

| Table 8: Chromatographic Conditions | |
|---|---|
| Instrument | Varian 920-LC |
| Column | Mightysil RP18 GP, 250 x 4.6 mm, 5 µm (1 x Aqua R18 guard column before analytical column). |
| Mobile Phase (gradient) | A: Aq. buffer: 0.25% NaOAc; pH 5.0<br>B: MeCN<br><table><tr><th>Time</th><th>%A</th><th>%B</th></tr><tr><td>0</td><td>93</td><td>7</td></tr><tr><td>10</td><td>93</td><td>7</td></tr><tr><td>15</td><td>20</td><td>80</td></tr><tr><td>25</td><td>20</td><td>80</td></tr><tr><td>25.1</td><td>93</td><td>7</td></tr><tr><td>30</td><td>93</td><td>7</td></tr></table> |
| Column Temperature | Ambient |
| Flow Rate | 1 mL/min |
| Detection Wavelength | 275 nm |
| Injection volume | 10 µL |
| Run time | 25 min |
| Retention time | phenylephrine: 5.4 min; substrate: 6.4 min |

SEQUENCE LISTING

<160> NUMBER OF SEQ ID NOS: 34

<210> SEQ ID NO 1
<211> LENGTH: 756
<212> TYPE: DNA
<213> ORGANISM: Lactobacillus kefir

<400> SEQUENCE: 1

```
atgactgatc gtttaaaagg caaagtagca attgtaactg gcggtacctt gggaattggc      60
ttggcaatcg ctgataagtt tgttgaagaa ggcgcaaagg ttgttattac cggccgtcac     120
gctgatgtag gtgaaaaagc tgccaaatca atcggcggca cagacgttat ccgttttgtc     180
caacacgatg cttctgatga agccggctgg actaagttgt ttgatacgac tgaagaagca     240
tttggcccag ttaccacggt tgtcaacaat gccggaattg cggtcagcaa gagtgttgaa     300
gataccacaa ctgaagaatg gcgcaagctg ctctcagtta acttggatgg tgtcttcttc     360
ggtacccgtc ttggaatcca acgtatgaag aataaaggac tcggagcatc aatcatcaat     420
atgtcatcta tcgaaggttt tgttggtgat ccaactctgg gtgcatacaa cgcttcaaaa     480
ggtgctgtca gaattatgtc taaatcagct gccttggatt gcgctttgaa ggactacgat     540
gttcgggtta acactgttca tccaggttat atcaagacac cattggttga cgatcttgaa     600
ggggcagaag aaatgatgtc acagcggacc aagacaccaa tgggtcatat cggtgaacct     660
aacgatatcg cttggatctg tgtttacctg gcatctgacg aatctaaatt tgccactggt     720
gcagaattcg ttgtcgatgg tggatacact gctcaa                               756
```

<210> SEQ ID NO 2
<211> LENGTH: 252
<212> TYPE: PRT
<213> ORGANISM: Lactobacillus kefir

<400> SEQUENCE: 2

```
Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Ser
                85                  90                  95
```

```
Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
            115                 120                 125

Met Lys Asn Lys Gly Leu Gly Ala Ser Ile Ile Asn Met Ser Ser Ile
        130                 135                 140

Glu Gly Phe Val Gly Asp Pro Thr Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Tyr Ile Lys
            180                 185                 190

Thr Pro Leu Val Asp Asp Leu Glu Gly Ala Glu Glu Met Met Ser Gln
            195                 200                 205

Arg Thr Lys Thr Pro Met Gly His Ile Gly Glu Pro Asn Asp Ile Ala
        210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250
```

<210> SEQ ID NO 3
<211> LENGTH: 756
<212> TYPE: DNA
<213> ORGANISM: Artificial sequence
<220> FEATURE:
<223> OTHER INFORMATION: variant of L. kefir ketoreductase

<400> SEQUENCE: 3

```
atgaccgatc gtctgaaggg caaagtagcc atcgtaaccg gcgggactct gggtatcggt      60
ttggcaatcg ccgataaatt tgtagaggag ggtgcgaaag tagttattac tggtcgtcac     120
gcggatgtag gtgaaaaggc cgccaaatca atcggcggca ctgatgttat cgctttgtc      180
cagcacgatg catccgatga agcaggctgg acgaaactgt tcgacaccac cgaggaggca     240
ttcggcccgg ttacgaccgt cgtgaacaat gcagggattg cagtttccaa aagcgttgaa     300
gacactacca cggaggaatg gcgtaaactg ctgtccgtta atctggatgg tgtttttttc     360
ggcacccgtc tgggcattca gcgcatgaaa aataaaggct gggcgctag catcatcaat     420
atgagcagta ttgcggggct ggtaggcgat ccgacgctgg gggcatacaa cgcttccaag     480
ggggcggtac gtatcatgtc gaaaagcgca gcgctggatt gcgcactgaa ggactacgat     540
gtgcgtgtca acacagtaca tccgggctgc atcaagaccc cgctggtcga tgatctggaa     600
ggtgctgagg aaatgatgtc acagcgtacg aaaaccccta tgggccacat tggcgaaccg     660
aatgacatcg catggatctg tgtgtacctg gcatctgacg aatcgaaatt tgcgacgggt     720
gcagaatttg tggtcgacgg cgggtatacc gcacag                               756
```

<210> SEQ ID NO 4
<211> LENGTH: 252
<212> TYPE: PRT
<213> ORGANISM: Artificial sequence
<220> FEATURE:
<223> OTHER INFORMATION: variant of L. kefir ketoreductase

<400> SEQUENCE: 4

```
Met Thr Asp Arg Leu Lys Gly Lys Val Ala Ile Val Thr Gly Gly Thr
1               5                   10                  15
```

Leu Gly Ile Gly Leu Ala Ile Ala Asp Lys Phe Val Glu Glu Gly Ala
         20                  25                  30

Lys Val Val Ile Thr Gly Arg His Ala Asp Val Gly Glu Lys Ala Ala
     35                  40                  45

Lys Ser Ile Gly Gly Thr Asp Val Ile Arg Phe Val Gln His Asp Ala
 50                  55                  60

Ser Asp Glu Ala Gly Trp Thr Lys Leu Phe Asp Thr Thr Glu Glu Ala
65                  70                  75                  80

Phe Gly Pro Val Thr Thr Val Asn Asn Ala Gly Ile Ala Val Ser
                 85                  90                  95

Lys Ser Val Glu Asp Thr Thr Glu Glu Trp Arg Lys Leu Leu Ser
             100                 105                 110

Val Asn Leu Asp Gly Val Phe Phe Gly Thr Arg Leu Gly Ile Gln Arg
             115                 120                 125

Met Lys Asn Lys Gly Leu Gly Ala Ser Ile Ile Asn Met Ser Ser Ile
130                 135                 140

Ala Gly Leu Val Gly Asp Pro Thr Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Cys Ile Lys
             180                 185                 190

Thr Pro Leu Val Asp Asp Leu Glu Gly Ala Glu Glu Met Met Ser Gln
         195                 200                 205

Arg Thr Lys Thr Pro Met Gly His Ile Gly Glu Pro Asn Asp Ile Ala
     210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250

<210> SEQ ID NO 5
<211> LENGTH: 756
<212> TYPE: DNA
<213> ORGANISM: Artificial Sequence
<220> FEATURE:
<223> OTHER INFORMATION: variant of L. kefir ketoreductase

<400> SEQUENCE: 5

```
atgaccgatc gtctgaaggg caaagtagcc atcgtaaccg gcgggactct gggtatcggt      60
ttggcaatcg ccgataaatt tgtagaggag ggtgcgaaag tagttattac tggtcgtcac     120
gcggatgtag gtgaaaaggc cgccaaatca atcggcggca ctgatgttat tcgctttgtc     180
cagcacgatg catccgatga ggcaggctgg acgaaactgt tcgacaccac cgaggaggca     240
ttcggcccgg ttacgaccgt cgtgaacaat gcaggattgc aatgagtaa agcgttgaa      300
gacactacca cggaggaatg gcgtaaactg ctgtccgtta atctggatgg tgttttttc      360
ggcacccgtc tgggcattca gcgcatgaaa aataaaggct gggcgctag catcatcaat      420
atgagcagta ttgcggggct ggtaggcgat ccgacgctgg ggcatacaa cgcttccaag      480
ggggcggtac gtatcatgtc gaaaagcgca gcgctggatt gcgcactgaa ggactacgat      540
gtgcgtgtca acacagtaca tccgggctgc atcaagaccc cgctggtcga tgatctggaa      600
ggttttgagg aaatgtgttc acagcgtacg aaaacccta tgggccacat tggcgaaccg      660
aatgacatcg catggatctg tgtgtacctg gcatctgacg aatcgaaatt tgcgacgggt      720
```
gcagaatttg tggtcgacgg cgggtatacc gcacag 756

<210> SEQ ID NO 6
<211> LENGTH: 252
<212> TYPE: PRT
<213> ORGANISM: Artificial Sequence
<220> FEATURE:
<223> OTHER INFORMATION: variant of L. kefir ketoreductase

<400> SEQUENCE: 6

```
Met Thr Asp Arg Leu Lys Gly Lys Val Ala Ile Val Thr Gly Gly Thr
1               5                   10                  15
Leu Gly Ile Gly Leu Ala Ile Ala Asp Lys Phe Val Glu Glu Gly Ala
            20                  25                  30
Lys Val Val Ile Thr Gly Arg His Ala Asp Val Gly Glu Lys Ala Ala
        35                  40                  45
Lys Ser Ile Gly Gly Thr Asp Val Ile Arg Phe Val Gln His Asp Ala
    50                  55                  60
Ser Asp Glu Ala Gly Trp Thr Lys Leu Phe Asp Thr Thr Glu Glu Ala
65                  70                  75                  80
Phe Gly Pro Val Thr Thr Val Val Asn Asn Ala Gly Ile Ala Met Ser
                85                  90                  95
Lys Ser Val Glu Asp Thr Thr Thr Glu Glu Trp Arg Lys Leu Leu Ser
            100                 105                 110
Val Asn Leu Asp Gly Val Phe Phe Gly Thr Arg Leu Gly Ile Gln Arg
        115                 120                 125
Met Lys Asn Lys Gly Leu Gly Ala Ser Ile Ile Asn Met Ser Ser Ile
    130                 135                 140
Ala Gly Leu Val Gly Asp Pro Thr Leu Gly Ala Tyr Asn Ala Ser Lys
145                 150                 155                 160
Gly Ala Val Arg Ile Met Ser Lys Ser Ala Ala Leu Asp Cys Ala Leu
                165                 170                 175
Lys Asp Tyr Asp Val Arg Val Asn Thr Val His Pro Gly Cys Ile Lys
            180                 185                 190
Thr Pro Leu Val Asp Asp Leu Glu Gly Phe Glu Glu Met Cys Ser Gln
        195                 200                 205
Arg Thr Lys Thr Pro Met Gly His Ile Gly Glu Pro Asn Asp Ile Ala
    210                 215                 220
Trp Ile Cys Val Tyr Leu Ala Ser Asp Glu Ser Lys Phe Ala Thr Gly
225                 230                 235                 240
Ala Glu Phe Val Val Asp Gly Gly Tyr Thr Ala Gln
                245                 250
```

<210> SEQ ID NO 7
<211> LENGTH: 756
<212> TYPE: DNA
<213> ORGANISM: Artificial Sequence
<220> FEATURE:
<223> OTHER INFORMATION: variant of L. kefir ketoreductase

<400> SEQUENCE: 7
atgaccgatc gtctgaaggg caaagtagcc atcgtaaccg gcgggactct gggtatcggt    60
ttggcaatcg ccgataaatt tgtagaggag ggtgcgaaag tagttattac tggtcgtcac   120
gcggatgtag gtgaaaaggc cgccaaatca atcggcggca ctgatgttat tcgctttgtc   180
cagcacgatg catccgatga ggcaggctgg acgaaactgt tcgacaccac cgaggaggca   240

| | |
|---|---|
| ttcggcccgg ttacgaccgt cgtgaacaat gcagggattg caatgagtaa aagcgttgaa | 300 |
| gacactacca cggaggaatg gcgtaaactg ctgtccgtta atctggatgg tgttttttc | 360 |
| ggcacccgtc tgggcattca gcgcatgaaa aataaaggct tgggcgctag catcatcaat | 420 |
| atgagcagta ttgcggggct ggtaggcgat ccgacgctgg gggcatacaa cgcttccaag | 480 |
| ggggcggtac gtatcatgtc gaaaagcgca gcgctggatt gcgcactgaa ggactacgat | 540 |
| gtgcgtgtca acacagtaca tccgggcggt atcaagaccc cgctggtcga tgatctggaa | 600 |
| ggttttgagg aaatgtgttc acagcgtacg aaaaccccta tgggccacat tggcgaaccg | 660 |
| aatgacatcg catggatctg tgtgtacctg gcatctgacg aatcgaaatt tgcgacgggt | 720 |
| gcagaatttg tggtcgacgg cgggtatacc gcacag | 756 |

<210> SEQ ID NO 8
<211> LENGTH: 252
<212> TYPE: PRT
<213> ORGANISM: Artificial Sequence
<220> FEATURE:
<223> OTHER INFORMATION: variant of L. kefir ketoreductase

<400> SEQUENCE: 8

```
Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Met Ser
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Ala Gly Leu Val Gly Asp Pro Thr Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Gly Ile Lys
            180                 185                 190

Thr Pro Leu Val Asp Asp Leu Glu Gly Phe Glu Glu Met Cys Ser Gln
        195                 200                 205

Arg Thr Lys Thr Pro Met Gly His Ile Gly Glu Pro Asn Asp Ile Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250
```

<210> SEQ ID NO 9
<211> LENGTH: 756

<212> TYPE: DNA
<213> ORGANISM: Artificial Sequence
<220> FEATURE:
<223> OTHER INFORMATION: variant of L. kefir ketoreductase

<400> SEQUENCE: 9

```
atgaccgatc gtctgaaggg caaagtagcc atcgtaaccg gcgggactct gggtatcggt      60
ttggcaatcg ccgataaatt tgtagaggag ggtgcgaaag tagttattac tggtcgtcac     120
gcggatgtag gtgaaaaggc cgccaaatca atcggcggca ctgatgttat tcgctttgtc     180
cagcacgatg catccgatga ggcaggctgg acgaaactgt tcgacaccac cgaggaggca     240
ttcggcccgg ttacgaccgt cgtgaacaat gcagggattg caatgctgaa aagcgttgaa     300
gacactacca cggaggaatg gcgtaaactg ctgtccgtta atctggatgg tgttttttc      360
ggcacccgtc tgggcattca gcgcatgaaa aataaaggct gggcgctag catcatcaat      420
atgagcagta ttgcggggct ggtaggcgat ccgacgctgg gggcatacaa cgcttccaag     480
ggggcggtac gtatcatgtc gaaaagcgca gcgctggatt gcgcactgaa ggactacgat     540
gtgcgtgtca acacagtaca tccgggcggt atcaagaccc cgctggtcga tgatctggaa     600
ggttttgagg aaatgtgttc acagcgtacg aaaaccccta tgggccacat ggcgaaccg      660
aatgacatcg catggatctg tgtgtacctg gcatctgacg aatcgaaatt tgcgacgggt     720
gcagaatttg tggtcgacgg cgggtttacc gcacag                              756
```

<210> SEQ ID NO 10
<211> LENGTH: 252
<212> TYPE: PRT
<213> ORGANISM: Artificial Sequence
<220> FEATURE:
<223> OTHER INFORMATION: variant of L. kefir ketoreductase

<400> SEQUENCE: 10

```
Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Met Leu
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Ala Gly Leu Val Gly Asp Pro Thr Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Gly Ile Lys
            180                 185                 190
```

```
Thr Pro Leu Val Asp Asp Leu Glu Gly Phe Glu Met Cys Ser Gln
            195                 200                 205

Arg Thr Lys Thr Pro Met Gly His Ile Gly Pro Asn Asp Ile Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Phe Thr Ala Gln
                245                 250
```

<210> SEQ ID NO 11
<211> LENGTH: 756
<212> TYPE: DNA
<213> ORGANISM: Artificial Sequence
<220> FEATURE:
<223> OTHER INFORMATION: variant of L. kefir ketoreductase

<400> SEQUENCE: 11

```
atgtcagatc gtctgaaggg caaagtagcc atcgtaaccg gcgggacgct gggtatcggt     60
ttggcaatcg ccgataaatt tgtagaggag ggtgcgaaag tagttattac tggtcgtcac    120
gcggatgtag gtgaaaaggc cgccaaatca atcggcggca ctgatgttat tcgctttgtc    180
cagcacgatg catccgatga ggcaggctgg acgaaactgt tcgacatcac cgaggaggca    240
ttcggcccgg ttacgaccgt cgtgaacaat gcagggattg caatgctgaa agcgttgaa     300
gacactacca cggaggaatg gcgtaaactg ctgtccgtta atctggatgg tgtttttttc    360
ggcacccgtc tgggcattca gcgcatgaaa ataaaggct tgggcgctag catcatcaat    420
atgagcagta ttgcggggct gatcggcgat ccgacgctgg gggcatacaa cgcttccaag    480
ggggcggtac gtatcatgtc gaaaagcgca gcgctggatt gcgcactgaa ggactacgat    540
gtgcgtgtca acacagtaca tccgggcggt atcaagaccc cgctggtcga tgatctggaa    600
ggttttgagg aaatgtgttc acagcgtacg aaaaccccta tgggccacat tggcgaaccg    660
aatgacatcg catggatctg tgtgtacctg gcatctgacg aatcgaaatt tgcgacgggt    720
gcagaatttg tggtcgacgg cgggtttacc gcacag                              756
```

<210> SEQ ID NO 12
<211> LENGTH: 252
<212> TYPE: PRT
<213> ORGANISM: Artificial Sequence
<220> FEATURE:
<223> OTHER INFORMATION: variant of L. kefir ketoreductase

<400> SEQUENCE: 12

```
Met Ser Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Ile Thr Glu Glu Ala
65                  70                  75                  80

Phe Gly Pro Val Thr Thr Val Val Asn Asn Ala Gly Ile Ala Met Leu
                85                  90                  95

Lys Ser Val Glu Asp Thr Thr Thr Glu Glu Trp Arg Lys Leu Leu Ser
            100                 105                 110
```

Val Asn Leu Asp Gly Val Phe Phe Gly Thr Arg Leu Gly Ile Gln Arg
            115                 120                 125

Met Lys Asn Lys Gly Leu Gly Ala Ser Ile Ile Asn Met Ser Ser Ile
        130                 135                 140

Ala Gly Leu Ile Gly Asp Pro Thr Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Gly Ile Lys
            180                 185                 190

Thr Pro Leu Val Asp Asp Leu Glu Gly Phe Glu Glu Met Cys Ser Gln
        195                 200                 205

Arg Thr Lys Thr Pro Met Gly His Ile Gly Glu Pro Asn Asp Ile Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Phe Thr Ala Gln
                245                 250

<210> SEQ ID NO 13
<211> LENGTH: 756
<212> TYPE: DNA
<213> ORGANISM: Artificial Sequence
<220> FEATURE:
<223> OTHER INFORMATION: variant of L. kefir ketoreductase

<400> SEQUENCE: 13

```
atgactgatc gtctgaaggg caaagtagcc atcgtaaccg gcgggacgct gggtatcggt      60
ttggcaatcg ccgataaatt tgtagaggag ggtgcgaaag tagttattac tggtcgtcac     120
gcggatgtag gtgaaaaggc cgccaaatca atcggcggca ctgatgttat tcgctttgtc     180
cagcacgatg catccgatga ggcaggctgg acgaaactgt tcgacatcac cgaggaggca     240
ttcggcccgg ttacgaccgt cgtgaacaat gcagggattg caatgctgaa agcgttgaa      300
gacactacca cggaggaatg gcgtaaactg ctgtccgtta atctggatgg tgtttttttc     360
ggcacccgtc tgggcattca gcgcatgaaa aataaaggct gggcgctag catcatcaat     420
atgagcagta ttgcgggggct gatcggcgat ccggcaatgg gggcatacaa cgcttccaag     480
ggggcggtac gtatcatgtc gaaaagcgca gcgctggatt gcgcactgaa ggactacgat     540
gtgcgtgtca acacagtaca tccgggcggt atcaagaccc cgctggtcga tgatctggaa     600
ggttttgagg aaatgtgttc acagcgtacg aaaacccccta tgggccacat tggcgaaccg     660
aatgacatcg catggatctg tgtgtacctg gcatctgacg aatcgaaatt tgcgacgggt     720
gcagaatttg tggtcgacgg cgggtttacc gcacag                                756
```

<210> SEQ ID NO 14
<211> LENGTH: 252
<212> TYPE: PRT
<213> ORGANISM: Artificial Sequence
<220> FEATURE:
<223> OTHER INFORMATION: variant of L. kefir ketoreductase

<400> SEQUENCE: 14

Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

```
Lys Val Val Ile Thr Gly Arg His Ala Asp Val Gly Glu Lys Ala Ala
             35                  40                  45
Lys Ser Ile Gly Gly Thr Asp Val Ile Arg Phe Val Gln His Asp Ala
 50                  55                  60
Ser Asp Glu Ala Gly Trp Thr Lys Leu Phe Asp Ile Thr Glu Glu Ala
 65                  70                  75                  80
Phe Gly Pro Val Thr Thr Val Asn Asn Ala Gly Ile Ala Met Leu
                 85                  90                  95
Lys Ser Val Glu Asp Thr Thr Glu Glu Trp Arg Lys Leu Leu Ser
                100                 105                 110
Val Asn Leu Asp Gly Val Phe Phe Gly Thr Arg Leu Gly Ile Gln Arg
            115                 120                 125
Met Lys Asn Lys Gly Leu Gly Ala Ser Ile Ile Asn Met Ser Ser Ile
130                 135                 140
Ala Gly Leu Ile Gly Asp Pro Ala Met Gly Ala Tyr Asn Ala Ser Lys
145                 150                 155                 160
Gly Ala Val Arg Ile Met Ser Lys Ser Ala Ala Leu Asp Cys Ala Leu
                165                 170                 175
Lys Asp Tyr Asp Val Arg Val Asn Thr Val His Pro Gly Gly Ile Lys
            180                 185                 190
Thr Pro Leu Val Asp Asp Leu Glu Gly Phe Glu Glu Met Cys Ser Gln
            195                 200                 205
Arg Thr Lys Thr Pro Met Gly His Ile Gly Glu Pro Asn Asp Ile Ala
210                 215                 220
Trp Ile Cys Val Tyr Leu Ala Ser Asp Glu Ser Lys Phe Ala Thr Gly
225                 230                 235                 240
Ala Glu Phe Val Val Asp Gly Gly Phe Thr Ala Gln
                245                 250

<210> SEQ ID NO 15
<211> LENGTH: 756
<212> TYPE: DNA
<213> ORGANISM: Artificial Sequence
<220> FEATURE:
<223> OTHER INFORMATION: variant of L. kefir ketoreductase

<400> SEQUENCE: 15
atgactgatc gtctgaaggg caaagtagcc atcgtaaccg gcgggacgct gggtatcggt      60
ttggcaatcg ccgataaatt tgtagaggag ggtgcgaaag tagttattac tggtcgtcac     120
gcggatgtag gtgaaaaggc cgccaaatca atcggcggca ctgatgttat tcgctttgtc     180
cagcacgatg tatccgatga ggcaggctgg acgaaactgt tcgacatcac cgaggaggca     240
ttcggcccgg ttacgaccgt cgtgaacaat gcagggattg caatgctgaa aagccttgaa     300
gacactacca cggaggaatg gcgtaaactg ctgtccgtta atctggatgg tgttttttc     360 ggcacccgtc tgggcattca gcgcatgaaa aataaaggct gggcgctag catcatcaat     420 atgagcagta ttgcggggct gatcggcgat ccggcaatgg gggcatacaa cgctaccaag     480
ggggcggtac gtatcatgtc gaaaagcgca gcgctggatt gcgcactgaa ggactacgat     540
gtgcgtgtca acacagtaca tccgggcggt atcaagaccc cgctggtcgc agatctgccg     600
ggttttgagg aaatgtgttc acagcgtacg aaaacccta tgggccacat tggcgaaccg     660
aatgacatcg catggatctg tgtgtacctg gcatctgacg aatcgaaatt tgcgacgggt     720
gcagaatttg tggtcgacgg cgggtttacc gcacag                              756
```

-continued

<210> SEQ ID NO 16
<211> LENGTH: 252
<212> TYPE: PRT
<213> ORGANISM: Artificial Sequence
<220> FEATURE:
<223> OTHER INFORMATION: variant of L. kefir ketoreductase

<400> SEQUENCE: 16

```
Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Thr Lys Leu Phe Asp Ile Thr Glu Glu Ala
65                  70                  75                  80

Phe Gly Pro Val Thr Thr Val Val Asn Asn Ala Gly Ile Ala Met Leu
                85                  90                  95

Lys Ser Leu Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Ala Gly Leu Ile Gly Asp Pro Ala Met Gly Ala Tyr Asn Ala Thr Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Gly Ile Lys
            180                 185                 190

Thr Pro Leu Val Ala Asp Leu Pro Gly Phe Glu Glu Met Cys Ser Gln
        195                 200                 205

Arg Thr Lys Thr Pro Met Gly His Ile Gly Glu Pro Asn Asp Ile Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Phe Thr Ala Gln
                245                 250
```

<210> SEQ ID NO 17
<211> LENGTH: 756
<212> TYPE: DNA
<213> ORGANISM: Artificial Sequence
<220> FEATURE:
<223> OTHER INFORMATION: variant of L. kefir ketoreductase

<400> SEQUENCE: 17
atgactgatc gtctgaaggg caaagtagcc ctggtaaccg gcgggacgct gggtatcggt    60
ttggcaatcg ccgataaatt tgtagaggag ggtgcgaaag tagttattac tggtcgtcac   120
gcggatgtag gtgaaaaggc cgccaaatca atcggcggca ctgatgttat tcgctttgtc   180
cagcacgatg tatccgatga ggcaggctgg acgaaactgt tcgacatcac cgaggaggca   240
ttcggcccgg ttacgaccgt cgtgaacaat gcaggattg caatgctgaa agccttgaa    300 gacactacca cggaggaatg gcgtaaactg ctgtccgtta atctggatgg tgttttttc   360

-continued

```
ggcacccgtc tgggcattca gcgcatgaaa aataaaggct tgggcgctag catcatcaat    420
atgagcagta ttgcggggct gatcggcgat ccggcaatgg gggcatacaa cgctaccaag    480
ggggcggtac gtatcatgtc gaaaagcgca gcgctggatt gcgcactgaa ggactacgat    540
gtgcgtgtca acacagtaca tccgggcggt atcaagaccc cgctggtcgc agatctgccg    600
ggttttgagg aaatgtgttc acagcgtacg aaaaccccta tgggccacat tggcgaaccg    660
aatgacatcg catggatctg tgtgtacctg gcatctgacg aatcgaaatt tgcgacgggt    720
gcagaatttg tggtcgacgg cgggtttacc gcacag                              756
```

<210> SEQ ID NO 18
<211> LENGTH: 252
<212> TYPE: PRT
<213> ORGANISM: Artificial Sequence
<220> FEATURE:
<223> OTHER INFORMATION: variant of L. kefir ketoreductase

<400> SEQUENCE: 18

```
Met Thr Asp Arg Leu Lys Gly Lys Val Ala Leu Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Thr Lys Leu Phe Asp Ile Thr Glu Glu Ala
65                  70                  75                  80

Phe Gly Pro Val Thr Thr Val Val Asn Asn Ala Gly Ile Ala Met Leu
                85                  90                  95

Lys Ser Leu Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Ala Gly Leu Ile Gly Asp Pro Ala Met Gly Ala Tyr Asn Ala Thr Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Gly Ile Lys
            180                 185                 190

Thr Pro Leu Val Ala Asp Leu Pro Gly Phe Glu Glu Met Cys Ser Gln
        195                 200                 205

Arg Thr Lys Thr Pro Met Gly His Ile Gly Glu Pro Asn Asp Ile Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Phe Thr Ala Gln
                245                 250
```

<210> SEQ ID NO 19
<211> LENGTH: 756
<212> TYPE: DNA
<213> ORGANISM: Artificial Sequence
<220> FEATURE:
<223> OTHER INFORMATION: variant of L. kefir ketoreductase

<400> SEQUENCE: 19

```
atgactgatc gtctgaaggg caaagtagcc ctggtaaccg gcgggacgct gggtatcggt      60
ttggcaatcg ccgataaatt tgtagaggag ggtgcgaaag tagttattac tggtcgtcac     120
gcggatgtag gtgaaaaggc cgccaaatca atcggcggca ctgatgttat tcgctttgtc     180
cagcacgatg tatccgatga ggcaggctgg acgaaactgt tcgacatcac cgaggaggca     240
ttcggcccgg ttacgaccgt cgtgaacaat gcagggattg caatgctgaa aagccttgaa     300
gacactacca cggaggaatg gcgtaaactg ctgtccgtta atctggatgg tgttttttc      360
ggcacccgtc tggcattca gcgcatgaaa aataaaggct ggcgctag catcatcaat        420
atgagcagta ttgcggggat catcggcgat ccggcaatgg gggcatacaa cgctaccaag     480
ggggcggtac gtatcatgtc gaaaagcgca gcgctggatt gcgcactgaa ggactacgat     540
gtgcgtgtca acacagtaca tccgggcggt atcaagaccc cgctggtcgc agatctgccg     600
ggttttgagg aaatgtgttc acagcgtacg aaaacccta tggccacat tggcgaaccg       660
aatgacatcg catggatctg tgtgtacctg gcatctgacg aatcgaaatt tgcgacgggt     720
gcagaatttg tggtcgacgg cgggtttacc gcacag                               756
```

<210> SEQ ID NO 20
<211> LENGTH: 252
<212> TYPE: PRT
<213> ORGANISM: Artificial Sequence
<220> FEATURE:
<223> OTHER INFORMATION: variant of L. kefir ketoreductase

<400> SEQUENCE: 20

```
Met Thr Asp Arg Leu Lys Gly Lys Val Ala Leu Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Thr Lys Leu Phe Asp Ile Thr Glu Glu Ala
65                  70                  75                  80

Phe Gly Pro Val Thr Thr Val Val Asn Asn Ala Gly Ile Ala Met Leu
                85                  90                  95

Lys Ser Leu Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Ala Gly Ile Ile Gly Asp Pro Ala Met Gly Ala Tyr Asn Ala Thr Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Gly Ile Lys
            180                 185                 190

Thr Pro Leu Val Ala Asp Leu Pro Gly Phe Glu Glu Met Cys Ser Gln
        195                 200                 205

Arg Thr Lys Thr Pro Met Gly His Ile Gly Glu Pro Asn Asp Ile Ala
```

```
                210              215              220
Trp Ile Cys Val Tyr Leu Ala Ser Asp Glu Ser Lys Phe Ala Thr Gly
225                      230                  235                  240

Ala Glu Phe Val Val Asp Gly Gly Phe Thr Ala Gln
                245                  250
```

<210> SEQ ID NO 21
<211> LENGTH: 756
<212> TYPE: DNA
<213> ORGANISM: Artificial sequence
<220> FEATURE:
<223> OTHER INFORMATION: variant of L. kefir ketoreductase

<400> SEQUENCE: 21

```
atgaccgatc gtctgaaggg caaagtagcc atcgtaaccg gcgggactct gggtatcggt        60
ttggcaatcg ccgataaatt tgtagaggag ggtgcgaaag tagttattac tggtcgtcac       120
gcggatgtag gtgaaaaggc cgccaaatca atcggcggca ctgatgttat tcgctttgtc       180
cagcacgatg catccgatga ggcaggctgg acgaaactgt tcgacaccac cgaggaggca       240
ttcggcccgg ttacgaccgt cgtgaacaat gcaggattg caatgagtaa aagcgttgaa        300
gacactacca cggaggaatg gcgtaaactg ctgtccgtta atctggatgg tgttttttc        360
ggcacccgtc tgggcattca gcgcatgaaa aataaaggct ggggcgctag catcatcaat       420
atgagcagta ttgcggggct ggtaggcgat ccgacgctgg gggcatacaa cgcttccaag       480
ggggcggtac gtatcatgtc gaaaagcgca gcgctggatt gcgcactgaa ggactacgat       540
gtgcgtgtca acacagtaca tccgggctgc atcaagaccc cgctggtcga tgatctggaa       600
ggtgctgagg aaatgatgtc acagcgtacg aaaaccccta tgggccacat tggcgaaccg       660
aatgacatcg catggatctg tgtgtacctg gcatctgacg aatcgaaatt tgcgacgggt       720
gcagaatttg tggtcgacgg cgggtatacc gcacag                                756
```

<210> SEQ ID NO 22
<211> LENGTH: 252
<212> TYPE: PRT
<213> ORGANISM: Artificial sequence
<220> FEATURE:
<223> OTHER INFORMATION: variant of L. kefir ketoreductase

<400> SEQUENCE: 22

```
Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Met Ser
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
```

Ala Gly Leu Val Gly Asp Pro Thr Leu Gly Ala Tyr Asn Ala Ser Lys
145                 150                 155                 160

Gly Ala Val Arg Ile Met Ser Lys Ser Ala Ala Leu Asp Cys Ala Leu
            165                 170                 175

Lys Asp Tyr Asp Val Arg Val Asn Thr Val His Pro Gly Cys Ile Lys
            180                 185                 190

Thr Pro Leu Val Asp Asp Leu Glu Gly Ala Glu Glu Met Met Ser Gln
        195                 200                 205

Arg Thr Lys Thr Pro Met Gly His Ile Gly Glu Pro Asn Asp Ile Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250

<210> SEQ ID NO 23
<211> LENGTH: 756
<212> TYPE: DNA
<213> ORGANISM: Artificial sequence
<220> FEATURE:
<223> OTHER INFORMATION: variant of L. kefir ketoreductase

<400> SEQUENCE: 23
atgaccgatc gtctgaaggg caaagtagcc atcgtaaccg gcgggactct gggtatcggt        60
ttggcaatcg ccgataaatt tgtagaggag ggtgcgaaag tagttattac tggtcgtcac       120
gcggatgtag gtgaaaaggc cgccaaatca atcggcggca ctgatgttat tcgctttgtc       180
cagcacgatg catccgatga ggcaggctgg acgaaactgt tcgacaccac cgaggaggca       240
ttcggcccgg ttacgaccgt cgtgaacaat gcagggattg cagtttccaa aagcgttgaa       300
gacactacca cggaggaatg cgtaaactg ctgtccgtta atctggatgg tgttttttc       360 ggcacccgtc tgggcattca gcgcatgaaa aataaaggct gggcgctag catcatcaat       420 atgagcagta ttgcgggggct ggtaggcgat ccgacgctgg gggcatacaa cgcttccaag       480
ggggcggtac gtatcatgtc gaaaagcgca gcgctggatt gcgcactgaa ggactacgat       540
gtgcgtgtca acacagtaca tccgggctgc atcaagaccc cgctggtcga tgatctggaa       600
ggtgctgagg aaatgtgttc acagcgtacg aaaaccccta tgggccacat tggcgaaccg       660
aatgacatcg catggatctg tgtgtacctg gcatctgacg aatcgaaatt tgcgacgggt       720
gcagaatttg tggtcgacgg cgggtatacc gcacag                                 756

<210> SEQ ID NO 24
<211> LENGTH: 252
<212> TYPE: PRT
<213> ORGANISM: Artificial sequence
<220> FEATURE:
<223> OTHER INFORMATION: variant of L. kefir ketoreductase

<400> SEQUENCE: 24

Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala

|   |   |   |   | 50 |   |   |   | 55 |   |   |   | 60 |   |   |
|---|---|---|---|---|---|---|---|---|---|---|---|---|---|---|

Ser Asp Glu Ala Gly Trp Thr Lys Leu Phe Asp Thr Thr Glu Glu Ala
65                  70                  75                  80

Phe Gly Pro Val Thr Thr Val Asn Asn Ala Gly Ile Ala Val Ser
                    85                  90                  95

Lys Ser Val Glu Asp Thr Thr Glu Glu Trp Arg Lys Leu Leu Ser
                100                 105                 110

Val Asn Leu Asp Gly Val Phe Phe Gly Thr Arg Leu Gly Ile Gln Arg
            115                 120                 125

Met Lys Asn Lys Gly Leu Gly Ala Ser Ile Ile Asn Met Ser Ser Ile
        130                 135                 140

Ala Gly Leu Val Gly Asp Pro Thr Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Cys Ile Lys
                180                 185                 190

Thr Pro Leu Val Asp Asp Leu Glu Gly Ala Glu Glu Met Cys Ser Gln
            195                 200                 205

Arg Thr Lys Thr Pro Met Gly His Ile Gly Glu Pro Asn Asp Ile Ala
        210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250

<210> SEQ ID NO 25
<211> LENGTH: 756
<212> TYPE: DNA
<213> ORGANISM: Artificial sequence
<220> FEATURE:
<223> OTHER INFORMATION: variant of L. kefir ketoreductase

<400> SEQUENCE: 25
atgaccgatc gtctgaaggg caaagtagcc atcgtaaccg gcgggactct gggtatcggt    60
ttggcaatcg ccgataaatt tgtagaggag ggtgcgaaag tagttattac tggtcgtcac   120
gcggatgtag gtgaaaaggc cgccaaatca atcggcggca ctgatgttat cgctttgtc    180
cagcacgatg catccgatga ggcaggctgg acgaaactgt tcgacaccac cgaggaggca   240
ttcggcccgg ttacgaccgt cgtgaacaat gcaggattg cagtttccaa agcgttgaa    300
gacactacca cggaggaatg gcgtaaactg ctgtccgtta atctggatgg tgttttttc    360
ggcacccgtc tgggcattca gcgcatgaaa aataaaggct gggcgctag catcatcaat   420
atgagcagta ttgcggggct ggtaggcgat ccgacgctgg ggcatacaa cgcttccaag    480
gggcggtac gtatcatgtc gaaaagcgca gcgctggatt gcgcactgaa ggactacgat   540
gtgcgtgtca acacagtaca tccgggctgc atcaagaccc cgctggtcga tgatctggaa   600
ggttttgagg aaatgatgtc acagcgtacg aaaaccccta tgggccacat tggcgaaccg   660
aatgacatcg catggatctg tgtgtacctg gcatctgacg aatcgaaatt tgcgacgggt   720
gcagaatttg tggtcgacgg cgggtatacc gcacag                             756

<210> SEQ ID NO 26
<211> LENGTH: 252
<212> TYPE: PRT
<213> ORGANISM: Artificial sequence
<220> FEATURE:
<223> OTHER INFORMATION: variant of L. kefir ketoreductase

<400> SEQUENCE: 26

Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Ser
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Ala Gly Leu Val Gly Asp Pro Thr Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Cys Ile Lys
            180                 185                 190

Thr Pro Leu Val Asp Asp Leu Glu Gly Phe Glu Glu Met Met Ser Gln
        195                 200                 205

Arg Thr Lys Thr Pro Met Gly His Ile Gly Glu Pro Asn Asp Ile Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250

<210> SEQ ID NO 27
<211> LENGTH: 756
<212> TYPE: DNA
<213> ORGANISM: Artificial sequence
<220> FEATURE:
<223> OTHER INFORMATION: variant of L. kefir ketoreductase

<400> SEQUENCE: 27
atgaccgatc gtctgaaggg caaagtagcc atcgtaaccg gcgggactct gggtatcggt    60
ttggcaatcg ccgataaatt tgtagaggag ggtgcgaaag tagttattac tggtcgtcac   120
gcggatgtag gtgaaaaggc cgccaaatca atcggcggca ctgatgttat tcgctttgtc   180
cagcacgatg catccgatga ggcaggctgg acgaaactgt tcgacaccac cgaggaggca   240
ttcggcccgg ttacgaccgt cgtgaacaat gcagggattg caatgagtaa agcgttgaa    300 gacactacca cggaggaatg gcgtaaactg ctgtccgtta atctggatgg tgttttttc    360 ggcacccgtc tgggcattca gcgcatgaaa aataaaggct gggcgctag catcatcaat   420 atgagcagta ttgcggggct ggtaggcgat ccgacgctgg ggcatacaa cgcttccaag    480

```
ggggcggtac gtatcatgtc gaaaagcgca gcgctggatt gcgcactgaa ggactacgat    540
gtgcgtgtca acacagtaca tccgggctgc atcaagaccc cgctggtcga tgatctggaa    600
ggttttgagg aaatgatgtc acagcgtacg aaaaccccta tgggccacat tggcgaaccg    660
aatgacatcg catggatctg tgtgtacctg gcatctgacg aatcgaaatt tgcgacgggt    720
gcagaatttg tggtcgacgg cgggtatacc gcacag                             756
```

<210> SEQ ID NO 28
<211> LENGTH: 252
<212> TYPE: PRT
<213> ORGANISM: Artificial sequence
<220> FEATURE:
<223> OTHER INFORMATION: variant of L. kefir ketoreductase

<400> SEQUENCE: 28

```
Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Met Ser
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Ala Gly Leu Val Gly Asp Pro Thr Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Cys Ile Lys
            180                 185                 190

Thr Pro Leu Val Asp Asp Leu Glu Gly Phe Glu Glu Met Met Ser Gln
        195                 200                 205

Arg Thr Lys Thr Pro Met Gly His Ile Gly Glu Pro Asn Asp Ile Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250
```

<210> SEQ ID NO 29
<211> LENGTH: 756
<212> TYPE: DNA
<213> ORGANISM: Artificial sequence
<220> FEATURE:
<223> OTHER INFORMATION: variant of L. kefir ketoreductase

<400> SEQUENCE: 29

```
atgaccgatc gtctgaaggg caaagtagcc atcgtaaccg gcgggactct gggtatcggt    60
```

```
ttggcaatcg ccgataaatt tgtagaggag ggtgcgaaag tagttattac tggtcgtcac    120
gcggatgtag gtgaaaaggc cgccaaatca atcggcggca ctgatgttat tcgctttgtc    180
cagcacgatg catccgatga ggcaggctgg acgaaactgt tcgacaccac cgaggaggca    240
ttcggcccgg ttacgaccgt cgtgaacaat gcagggattg caatgagtaa aagcgttgaa    300
gacactacca cggaggaatg gcgtaaactg ctgtccgtta atctggatgg tgttttttc     360 ggcacccgtc tgggcattca gcgcatgaaa aataaaggct tgggcgctag catcatcaat    420
atgagcagta ttgcggggct ggtaggcgat ccgacgctgg ggcatacaa cgcttccaag     480 ggggcggtac gtatcatgtc gaaaagcgca gcgctggatt gcgcactgaa ggactacgat    540
gtgcgtgtca acacagtaca tccgggctgc atcaagaccc cgctggtcga tgatctggaa    600
ggttttgagg aaatgtgttc acagcgtacg aaaaccccta tgggccacat tggcgaaccg    660
aatgacatcg catggatctg tgtgtacctg gcatctgacg aatcgaaatt tgcgacgggt    720
gcagaatttg tggtcgacgg cgggtttacc gcacag                              756
```

```
<210> SEQ ID NO 30
<211> LENGTH: 252
<212> TYPE: PRT
<213> ORGANISM: Artificial sequence
<220> FEATURE:
<223> OTHER INFORMATION: variant of L. kefir ketoreductase

<400> SEQUENCE: 30

Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Asn Asn Ala Gly Ile Ala Met Ser
                85                  90                  95

Lys Ser Val Glu Asp Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Ala Gly Leu Val Gly Asp Pro Thr Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Cys Ile Lys
            180                 185                 190

Thr Pro Leu Val Asp Asp Leu Glu Gly Phe Glu Met Cys Ser Gln
        195                 200                 205

Arg Thr Lys Thr Pro Met Gly His Ile Gly Glu Pro Asn Asp Ile Ala
    210                 215                 220

Trp Ile Cys Val Tyr Leu Ala Ser Asp Glu Ser Lys Phe Ala Thr Gly
225                 230                 235                 240
```

```
Ala Glu Phe Val Val Asp Gly Gly Phe Thr Ala Gln
            245                 250
```

<210> SEQ ID NO 31
<211> LENGTH: 756
<212> TYPE: DNA
<213> ORGANISM: Artificial sequence
<220> FEATURE:
<223> OTHER INFORMATION: variant of L. kefir ketoreductase

<400> SEQUENCE: 31

```
atgaccgatc gtctgaaggg caaagtagcc atcgtaaccg gcgggactct gggtatcggt      60
ttggcaatcg ccgataaatt tgtagaggag ggtgcgaaag tagttattac tggtcgtcac     120
gcggatgtag gtgaaaaggc cgccaaatca atcggcggca ctgatgttat tcgctttgtc     180
cagcacgatg catccgatga ggcaggctgg acgaaactgt tcgacaccac cgaggaggca     240
ttcggcccgg ttacgaccgt cgtgaacaat gcaggggattg caatgagtaa agcgttgaa     300
gacactacca cggaggaatg gcgtaaactg ctgtccgtta atctggatgg tgtttttttc     360
ggcacccgtc tgggcattca gcgcatgaaa aataaaggct tgggcgctag catcatcaat     420
atgagcagta ttgcggggct ggtaggcgat ccgacgctgg gggcatacaa cgcttccaag     480
ggggcggtac gtatcatgtc gaaaagcgca gcgctggatt gcgcactgaa ggactacgat     540
gtgcgtgtca acacagtaca tccgggcggt atcaagaccc cgctggtcga tgatctggaa     600
ggttttgagg aaatgtgttc acagcgtacg aaaacccctta tgggccacat tggcgaaccg     660
aatgacatcg catggatctg tgtgtacctg gcatctgacg aatcgaaatt tgcgacgggt     720
gcagaatttg tggtcgacgg cgggtttacc gcacag                               756
```

<210> SEQ ID NO 32
<211> LENGTH: 252
<212> TYPE: PRT
<213> ORGANISM: Artificial sequence
<220> FEATURE:
<223> OTHER INFORMATION: variant of L. kefir ketoreductase

<400> SEQUENCE: 32

```
Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Met Ser
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Ala Gly Leu Val Gly Asp Pro Thr Leu Gly Ala Tyr Asn Ala Ser Lys
145                 150                 155                 160
```

```
Gly Ala Val Arg Ile Met Ser Lys Ser Ala Ala Leu Asp Cys Ala Leu
            165                 170                 175

Lys Asp Tyr Asp Val Arg Val Asn Thr Val His Pro Gly Gly Ile Lys
        180                 185                 190

Thr Pro Leu Val Asp Asp Leu Glu Gly Phe Glu Glu Met Cys Ser Gln
    195                 200                 205

Arg Thr Lys Thr Pro Met Gly His Ile Gly Glu Pro Asn Asp Ile Ala
210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Phe Thr Ala Gln
                245                 250
```

<210> SEQ ID NO 33
<211> LENGTH: 756
<212> TYPE: DNA
<213> ORGANISM: Artificial sequence
<220> FEATURE:
<223> OTHER INFORMATION: variant of L. kefir ketoreductase

<400> SEQUENCE: 33

```
atgtcagatc gtctgaaggg caaagtagcc atcgtaaccg gcgggactct gggtatcggt    60
ttggcaatcg ccgataaatt tgtagaggag ggtgcgaaag tagttattac tggtcgtcac   120
gcggatgtag gtgaaaaggc cgccaaatca atcggcggca ctgatgttat tcgctttgtc   180
cagcacgatg catccgatga ggcaggctgg acgaaactgt tcgacaccac cgaggaggca   240
ttcggcccgg ttacgaccgt cgtgaacaat gcagggattg caatgagtaa agcgttgaa   300
gacactacca cggaggaatg cgtaaactg ctgtccgtta atctggatgg tgttttttc    360
ggcacccgtc tgggcattca cgcatgaaa atcaaaggct gggcgctag catcatcaat   420
atgagcagta ttgcggggct ggtaggcgat ccgacgctgg gggcatacaa cgcttccaag   480
ggggcggtac gtatcatgtc gaaaagcgca gcgctggatt gcgcactgaa ggactacgat   540
gtgcgtgtca acacagtaca tccgggcggt atcaagaccc cgctggtcga tgatctggaa   600
ggttttgagg aaatgtgttc acagcgtacg aaaaccccta tgggccacat tggcgaaccg   660
aatgacatcg catggatctg tgtgtacctg gcatctgacg aatcgaaatt tgcgacgggt   720
gcagaatttg tggtcgacgg cgggtatacc gcacag                              756
```

<210> SEQ ID NO 34
<211> LENGTH: 252
<212> TYPE: PRT
<213> ORGANISM: Artificial sequence
<220> FEATURE:
<223> OTHER INFORMATION: variant of L. kefir ketoreductase

<400> SEQUENCE: 34

```
Met Ser Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80
```

```
Phe Gly Pro Val Thr Thr Val Val Asn Asn Ala Gly Ile Ala Met Ser
            85              90              95
Lys Ser Val Glu Asp Thr Thr Thr Glu Glu Trp Arg Lys Leu Leu Ser
            100             105             110
Val Asn Leu Asp Gly Val Phe Phe Gly Thr Arg Leu Gly Ile Gln Arg
            115             120             125
Met Lys Asn Lys Gly Leu Gly Ala Ser Ile Ile Asn Met Ser Ser Ile
            130             135             140
Ala Gly Leu Val Gly Asp Pro Thr Leu Gly Ala Tyr Asn Ala Ser Lys
145             150             155             160
Gly Ala Val Arg Ile Met Ser Lys Ser Ala Ala Leu Asp Cys Ala Leu
                165             170             175
Lys Asp Tyr Asp Val Arg Val Asn Thr Val His Pro Gly Gly Ile Lys
            180             185             190
Thr Pro Leu Val Asp Asp Leu Glu Gly Phe Glu Glu Met Cys Ser Gln
            195             200             205
Arg Thr Lys Thr Pro Met Gly His Ile Gly Glu Pro Asn Asp Ile Ala
            210             215             220
Trp Ile Cys Val Tyr Leu Ala Ser Asp Glu Ser Lys Phe Ala Thr Gly
225             230             235             240
Ala Glu Phe Val Val Asp Gly Gly Tyr Thr Ala Gln
            245             250
```

KETOREDUCTASE POLYPEPTIDES FOR THE PREPARATION OF PHENYLEPHRINE

1. CROSS-RELATED APPLICATIONS

The present application is a Continuation of U.S. patent application Ser. No. 17/085,783, filed Oct. 30, 2020, which is a Continuation of U.S. patent application Ser. No. 16/778, 368, filed Jan. 31, 2020, now U.S. Pat. No. 10,870,835, which is a Continuation of U.S. patent application Ser. No. 16/437,354, filed Jun. 11, 2019, now U.S. Pat. No. 10,590, 396, which is a Continuation of U.S. patent application Ser. No. 15/812,628, filed Nov. 14, 2017, now U.S. Pat. No. 10,358,631, which is a Continuation of U.S. patent application Ser. No. 14/775,056, filed Jun. 30, 2015, now U.S. Pat. No. 9,834,758, which is a Divisional of U.S. patent application Ser. No. 13/390,677, filed Feb. 15, 2012, now U.S. Pat. No. 9,102,959, which is a national stage application filed under 35 USC § 371 and claims priority of the international application PCT/US2010/046020, filed Aug. 19, 2010, and U.S. provisional patent application 61/235, 324, filed Aug. 19, 2009, which is hereby incorporated by reference herein.

2. TECHNICAL FIELD

The disclosure relates to engineered ketoreductase polypeptides and processes of using the polypeptides for production of phenylephrine.

3. REFERENCE TO SEQUENCE LISTING, TABLE OR COMPUTER PROGRAM

The Sequence Listing concurrently submitted herewith with the specification as an ASCII formatted text file via EFS-Web with a file name of CX2-015WO1_ST25.txt with a creation date of Aug. 19, 2010, and a size of 58,319 bytes. The Sequence Listing filed via EFS-Web is part of the specification and is hereby incorporated in its entirety by reference herein.

4. BACKGROUND (R)-Phenylephrine (depicted herein as compound (1)) is an al-adrenergic receptor agonist used as a decongestant, a pupil dilator and to increase blood pressure.

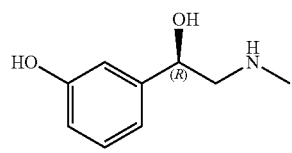

(1)

Phenylephrine is used as a substitute for pseudoephedrine (e.g., Pfizer's Sudafed®). Phenylephrine is a selective α-adrenergic receptor agonist and does not cause the release of endogenous noradrenaline. Phenylephrine is less likely to cause side-effects such as central nervous system stimulation, insomnia, anxiety, irritability, and restlessness.

Various chemical reaction methods have been described for the synthesis of phenylephrine. U.S. Pat. No. 6,900,203 describes a synthetic route to phenylephrine that includes a chiral addition of cyanide to a ring-fluorinated phenaldehyde intermediate using hydroxynitrile lyase enzyme. No routes to phenylephrine have been described involving a stereoselective reduction using a ketoreductase.

5. SUMMARY

The disclosure provides methods and polypeptides for stereoselective reduction of 1-(3-hydroxyphenyl)-2-(methylamino)ethanone (depicted herein as compound (2)) to phenylephrine using a engineered ketoreductase polypeptide (alternatively referred to as a KRED).

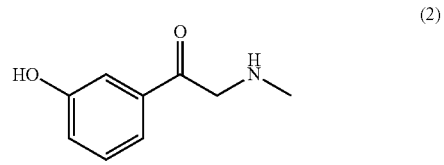

(2)

The disclosure provides engineered polypeptides having ketoreductase activity, polynucleotides encoding the polypeptides, and methods of using the polypeptides for the synthesis of enantiospecific compounds.

The engineered ketoreductase polypeptides of the disclosure are capable of catalyzing the conversion of compound (2) to compound (1) with a relative activity at least 10-fold greater than the wild-type ketoreductase polypeptide of SEQ ID NO: 2, and with an improved stereoselectivity capable of providing compound (1) in >99% e.e. Accordingly, in some embodiments, the disclosure provides methods of using the engineered polypeptides for synthesizing (R)-phenylephrine of compound (1). The methods include pH ranges, isopropyl alcohol (IPA) concentrations, and buffer substances that are useful for maintaining substrate stability and providing improved catalysis (e.g., higher conversion with higher substrate loading at lower enzyme concentrations).

In one embodiment, the engineered polypeptides have improved enzyme properties as compared to the naturally occurring ketoreductase of L. kefir, the sequence of which is represented by SEQ ID NO: 2, in particular the engineered polypeptides are capable of converting 1-(3-hydroxyphenyl)-2-(methylamino)ethanone to (R)-phenylephrine with improved activity and enantioselectivity. In some embodiments, the engineered polypeptides having ketoreductase activity are improved in activity and enantioselectivity for converting compound (2) to compound (1) as compared to another engineered ketoreductase polypeptide, such as a polypeptide of SEQ ID NO: 4, 6, 8, 10, 12, 14, 16, 18, 20, 22, 24, 26, 28, 30, 32, or 34. The improved properties of the engineered polypeptides provide for improved processes for preparing compound (1) and related compounds of Formula I (see below). In addition to improved enzyme activity (e.g., conversion rate), the engineered polypeptides of the disclosure comprise improved pH stability, improved solvent characteristics (e.g., activity in 50% isopropyl alcohol), and reduced non-enzymatic decomposition of substrate (i.e., compound (2)). In some embodiments, the engineered polypeptides having ketoreductase activity are characterized by a combination of improved properties, such as increased enzymatic activity, pH stability, and reduced compound (2) decomposition compared to a wild-type ketoreductase (e.g., an L. kefir ketoreductase).

In some embodiments, the engineered polypeptides having ketoreductase activity are improved with respect to enzyme activity as compared to the activity of the polypeptide comprising SEQ ID NO: 4 in the synthesis of compound (1). In some embodiments, the engineered polypeptides having ketoreductase activity have at least 7-fold greater than the activity of SEQ ID NO: 4 at a reaction condition of pH about 6.0-7.5 and temperature of about 25-35° C. In some embodiments, the engineered polypeptides are capable of converting compound (2) to compound (1) with an activity at least 14-fold, at least 28-fold, at least 46-fold, at least 74-fold, at least 112-fold, at least 134-fold, at least 160-fold greater than the activity of the polypeptide of SEQ ID NO: 4.

In some embodiments, the improved enzymatic activity of the engineered polypeptides having ketoreductase activity can be characterized by an increase in the generation of a chiral alcohol (e.g., compound of Formula I) from a ketone (e.g., compound of Formula II), such as the enantiospecific conversion of 1-(3-hydroxyphenyl)-2-(methylamino)ethanone (compound (2)) to (R)-phenylephrine (compound (1)) under a defined condition. In some embodiments, the engineered polypeptides are capable of this conversion with a yield of compound (1) of at least 80%, 90%, 92%, 94%, 96%, 98%, 99% or more up to the theoretical yield of 100% under the defined condition. In some embodiments, the defined condition for the enzymatic conversion using an engineered polypeptide of the disclosure comprises pH about 6.0-7.5 (e.g., about 7.0). In some embodiments, the defined condition comprises a pH adjusted after two hours of reaction from about pH 7.0 to about pH 6.75. In some embodiments, the defined condition comprises a temperature of about 25-40° C. (e.g., about 30° C.). In some embodiments, the defined condition comprises a solvent comprising a buffer solution (e.g., 0.1 M TEA or 0.05 M potassium phosphate) and 50% (v/v) isopropyl alcohol. In some embodiments, the defined condition comprises a substrate loading of (e.g., concentration of compound (2)) of at least about 50-400 g/L (e.g., about 50-100 g/L, about 50-200 g/L, about 50-300 g/L, about 50-400 g/L, about 100 g/L, about 200 g/L, about 300 g/L or about 400 g/L). In some embodiments, the defined condition comprises an engineered polypeptide loading of about 0.1-1.5 g/L, about 0.5-1.2 g/L, or about 0.7-1.0 g/L. In some embodiments, the defined condition comprises about 0.03-0.1 g/L of NADP. In some embodiments, the defined condition comprises carrying out the reaction under an inert atmosphere (e.g., $N_2$).

In some embodiments, the defined condition comprises a combination of the above e.g.: (1) a substrate loading of at least about 50-300 g/L of 1-(3-hydroxyphenyl)-2-(methylamino)ethanone; (2) engineered polypeptide loading of about 0.1-1.5 g/L; (3) a pH of about pH 6.0 to about 7.5; (3) about 50% (v/v) IPA; (4) about 0.03-0.1 g/L NADP; and (5) reaction temperature of about 25-35° C.

In some embodiments, the engineered polypeptides under the defined conditions above are capable of converting at least 50%, at least 60%, at least 70%, at least 80%, at least 90%, at least 95%, at least 97%, at least 99%, or more of compound (2) to compound (1) in a reaction time of about 8-24 hours. In some embodiments, the conversion rate comprises at least 70%, 80%, 90%, or 99% in a reaction time of 24 h or less.

In some embodiments, the engineered polypeptides having ketoreductase activity are improved with respect to the level of undesired non-enzymatic substrate decomposition during the synthesis of (R)-phenylephrine. In some embodiments, the level of compound (2) decomposition products is less than 10%, less than 7.5%, less than 6%, less than 5%, less than 4%, less than 3%, less than 2%, less than 1%, less than 0.5%, less than 0.2%, or less than 0.1% of the total phenylephrine formed.

In some embodiments, the engineered polypeptides are capable of converting 1-(3-hydroxyphenyl)-2-(methylamino)ethanone to (R)-phenylephrine and comprise an amino acid sequence having at least 70%, 75%, 80%, 81%, 82%, 83%, 84%, 85%, 86%, 87%, 88%, 89%, 90%, 91%, 92%, 93%, 94%, 95%, 96%, 97%, 98%, 99% or more identity to a reference sequence of SEQ ID NO:2, 4, 6, 8, 10, 12, 14, 16, 18, 20, 22, 24, 26, 28, 30, 32, or 34 and comprising at least one residue difference at a position corresponding to T2, I11, A64, T76, V95, S96, V99, E145, A145, F147, L147, V148, T152, L153, S159, Y190, C190, D197, E200, A202, M206, or Y249.

In some embodiments, the engineered polypeptide is capable of converting 1-(3-hydroxyphenyl)-2-(methylamino)ethanone to (R)-phenylephrine and has at least 70%, 80%, 85%, 90%, 95% or more identity to the reference sequence of SEQ ID NO: 4 and comprises at least one residue difference at a position of SEQ ID NO: 4 corresponding to T2, I11, A64, T76, V95, V99, V148, T152, L153, S159, or D197. In certain embodiments, the engineered polypeptide further comprises at least one residue difference at a position of SEQ ID NO: 4 corresponding to S96, L147, T152, L153, C190, E200, or Y249. In certain embodiments, the amino acid sequence of the engineered polypeptide comprises at least one residue difference compared to SEQ ID NO: 4 selected from T2S, I111L, A64V, T76I, V95M, S96L, L147I, C190G, A202F, M206C, and Y249F, and in one embodiment comprises the residue difference V95M. In certain embodiments, the amino acid sequence of the engineered polypeptide comprises at least two residue differences compared to SEQ ID NO: 4 selected from V95M, S96L, L147I, C190G, A202F, M206C, and Y249F, and in one embodiment the amino acid sequence comprises the residue differences compared to SEQ ID NO: 4 of: V95M, A202F, and M206C. In certain embodiments, the amino acid sequence of the engineered polypeptide comprises the residue differences compared to SEQ ID NO: 4 of: V95M, C190G, A202F, and M206C.

In certain embodiments, the engineered polypeptide is capable of converting 1-(3-hydroxyphenyl)-2-(methylamino)ethanone to (R)-phenylephrine and has at least 70% identity to the reference sequence of SEQ ID NO: 4, comprises an amino acid sequence having at least one residue difference at a position of SEQ ID NO: 4 corresponding to T2, I11, A64, T76, V95, S96, V99, A145, L147, V148, T152, L153, S159, C190, D197, E200, A202, M206, or Y249, and further comprises at least 1-60 conservative amino acid substitutions at positions of SEQ ID NO: 4 other than those corresponding to I11, A64, T76, V95, S96, V99, A145, L147, V148, T152, L153, S159, C190, D197, E200, A202, M206, and Y249.

In certain embodiments, the engineered polypeptide is capable of converting 1-(3-hydroxyphenyl)-2-(methylamino)ethanone to (R)-phenylephrine and has at least 70% identity to the reference sequence of SEQ ID NO: 4, comprises an amino acid sequence having at least one residue difference at a position of SEQ ID NO: 4 corresponding to T2, I11, A64, T76, V95, S96, V99, A145, L147, V148, T152, L153, S159, C190, D197, E200, A202, M206, or Y249, and further comprises at least one residue difference selected from one of the six following groups: (1) I11, A64, T76, S96, L147 and/or V148 is substituted with an amino acid selected from alanine (A), leucine (L), isoleucine (I), and valine (V); (2) V95, V99, T152, L153, C190, and/or D197 is substituted with an amino acid selected from alanine (A), valine (V), leucine (L), isoleucine (I), glycine (G), or methionine (M); (3) A202 and/or Y249 is substituted with an amino acid selected from tyrosine (Y), phenylalanine (F), or tryptophan (W); (4) S159 is substituted with an amino acid selected from asparagine (N), glutamine (Q), serine (S) or threonine (T); (5) E200 is substituted with an amino acid selected from proline (P) or histidine (H); (6) M206 is substituted with a cysteine.

In some embodiments, the engineered polypeptides of the present disclosure can comprise an amino acid sequence having one or more residue difference at a position of SEQ ID NO: 4 corresponding to T2, I11, A64, T76, V95, S96, V99, A145, L147, V148, T152, L153, S159, C190, D197, E200, A202, M206, and Y249, and can further include one or more residue differences at other residue positions (i.e., positions other than T2, I11, A64, T76, V95, S96, V99, A145, L147, V148, T152, L153, S159, C190, D197, E200, A202, M206, and Y249). Accordingly, in certain embodiments, the engineered ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40, 1-45, 1-50, 1-55, or 1-60 residue differences at other amino acid residue positions. In some embodiments, the number of differences can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, or 60 residue differences at the other amino acid residue positions (i.e., beside residues 11, 64, 76, 95, 96, 99, 145, 147, 148, 152, 153, 159, 190, 197, 200, 202, 206, and 249). In some embodiments, the residue differences at SEQ ID NO: 4 positions other than T2, I11, A64, T76, V95, S96, V99, A145, L147, V148, T152, L153, S159, C190, D197, E200, A202, M206, and Y249 comprise conservative substitutions.

In some embodiments, the engineered polypeptides capable of converting 1-(3-hydroxyphenyl)-2-(methylamino)ethanone to (R)-phenylephrine comprise an amino acid sequence at least about 70%, 75%, 80%, 81%, 82%, 83%, 84%, 85%, 86%, 87%, 88%, 89%, 90%, 91%, 92%, 93%, 94%, 95%, 96%, 97%, 98%, 99% or more identical to SEQ ID NO: 2, and further comprises the combination of residue differences of any one of SEQ ID NO: 4, 6, 8, 10, 12, 14, 16, 18, 20, 22, 24, 26, 28, 30, 32, or 34 as compared to SEQ ID NO: 2. In certain embodiments, the engineered polypeptides comprise an amino acid sequence at least about 70% identical to SEQ ID NO: 4, and further comprise the combination of residue differences of any one of SEQ ID NO: 6, 8, 10, 12, 14, 16, 18, 20, 22, 24, 26, 28, 30, 32, or 34 as compared to SEQ ID NO: 2.

In some embodiments, the engineered polypeptides having ketoreductase activity catalyzing an enantiomeric excess of at least 99% of (R)-phenylephrine comprises an amino acid sequence selected from SEQ ID NO: 4, 6, 8, 10, 12, 14, 16, 18, 20, 22, 24, 26, 28, 30, 32, and 34.

In another embodiment, the present disclosure provides methods for preparing an (R)-phenylephrine product compound comprising: contacting an engineered polypeptide of the present disclosure (e.g., as described above and elsewhere herein) with a mixture comprising a 1-(3-hydroxyphenyl)-2-(methylamino)ethanone substrate and a buffer under reaction conditions suitable to convert 1-(3-hydroxyphenyl)-2-(methylamino)ethanone to (R)-phenylephrine.

Accordingly, in some embodiments, the methods for preparing an (R)-phenylephrine product compound can be carried out wherein the engineered polypeptide is selected from the polypeptides of SEQ ID NO: 4, 6, 8, 10, 12, 14, 16, 18, 20, 22, 24, 26, 28, 30, 32, or 34; or an amino acid sequence at least about 70%, 75%, 80%, 81%, 82%, 83%, 84%, 85%, 86%, 87%, 88%, 89%, 90%, 91%, 92%, 93%, 94%, 95%, 96%, 97%, 98%, 99% or more identical to SEQ ID NO: 2, which further comprises the combination of residue differences of any one of SEQ ID NO: 4, 6, 8, 10, 12, 14, 16, 18, 20, 22, 24, 26, 28, 30, 32, or 34 as compared to SEQ ID NO: 2.

In certain embodiments, the methods for preparing an (R)-phenylephrine product compound can be carried out wherein the 1-(3-hydroxyphenyl)-2-(methylamino)ethanone substrate is selected from compound (2) or compound (2a) (i.e., the hydrosulfate form of compound (2) shown below).

In certain embodiments, the methods for preparing (R)-phenylephrine of the present disclosure can be carried out wherein the reaction conditions comprise a pH of about 6.0 to about 7.5 (e.g., about 6.5 to about 7.0, or about 7.0). In some embodiments, the method can be carried out wherein the reaction conditions comprise an initial pH of about 7.0 and then adjusting the initial pH to about 6.75 after about 2 hours. In some embodiments, the method further comprises after completion of the enzymatic reaction the steps of saturating the mixture with salt (e.g., NaCl) and adjusting the pH to 8.0 to 9.0, thereby producing a free base of compound (1). In some embodiments, the method further comprises after completion of the enzymatic reaction the step of extraction of the free base of compound (1) with isopropyl alcohol (IPA). In some embodiments, the method further comprises after completion of the enzymatic reaction the step of acidifying (e.g., with HCl) the IPA extract of the mixture and isolating the (R)-phenylephrine salt (e.g., HCl salt of compound (1a) below).

In some embodiments, the methods for preparing (R)-phenylephrine of the present disclosure can be carried out wherein the mixture comprises at least about 50-400 g/L 1-(3-hydroxyphenyl)-2-(methylamino)ethanone substrate loading (e.g., about 50-100 g/L, about 50-200 g/L, about 50-300 g/L, about 50-400 g/L, about 100 g/L, about 200 g/L, about 300 g/L or about 400 g/L). The values for substrate loadings provided herein are based on the molecular weight of 1-(3-hydroxyphenyl)-2-(methylamino)ethanone (i.e., compound (2)) and contemplates that the equivalent molar amounts of 1-(3-hydroxyphenyl)-2-(methylamino)ethanone hydrosulfate (compound (2a)) also can be used (e.g., 100 g/L of compound (2) equals about 130 g/L of compound (2a)).

In some embodiments, the methods for preparing (R)-phenylephrine of the present disclosure can be carried out wherein the resulting engineered polypeptide concentration in the mixture is about 0.1-1.5 g/L, about 0.5-1.2 g/L, or about 0.7-1.0 g/L. In certain embodiments, the method can be carried out wherein the reaction conditions comprise a temperature of about 25° C. to about 35° C. (e.g., at about 30° C.). In certain embodiments, the method can be carried out wherein the mixture comprises a solvent comprising a buffer and 50% (v/v) isopropyl alcohol. In some embodiments, the buffer is selected from triethanolamine (e.g., about 0.05 M to about 0.25 M TEA, or about 0.1 M TEA) and potassium phosphate (e.g., about 0.025 M to about 0.1 M phosphate, or about 0.05 M phosphate). In certain embodiments, the method can be carried out wherein the mixture comprises about 0.03-0.1 g/L NADP (e.g., about 0.05 g/L NADP). In certain embodiments, the method can be carried out wherein the reaction conditions comprise an inert atmosphere (e.g., $N_2$, Ar, etc.).

Accordingly, in some embodiments, the methods for preparing (R)-phenylephrine of the present disclosure can be carried out using a combination of any of the mixture and reaction conditions disclosed above (and elsewhere herein) e.g., (1) a pH of about 6.75-7.0; (2) a temperature of about 30° C.; (3) about 50% isopropyl alcohol; (4) about 0.05 g/L NADP; (5) about 100 g/L 1-(3-hydroxyphenyl)-2-(methylamino)ethanone; (5) and about 0.7-1.1 g/L of the polypeptide; and (6) N$_2$ atmosphere.

In some embodiments, the method can reaction conditions comprise a pH of about 6.75-7.0, a temperature of about 30° C., about 100 g/L of compound (2) (or 130 g/L of the hydrosulfate of compound (2a)), and about 1 g/L of an polypeptide having a sequence as set forth in SEQ ID NO: 4, 6, 8, 10, 12, 14, 16, 18, 20, 22, 24, 26, 28, 30, 32, or 34 in a reaction time of about 19-24 hrs, wherein at least 50%-99% of the substrate is converted to (R)-phenylephrine.

In another aspect, the disclosure provides a method for the stereoselective conversion of a substrate compound of Formula II:

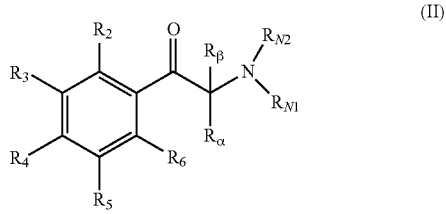

to a product compound of Formula I:

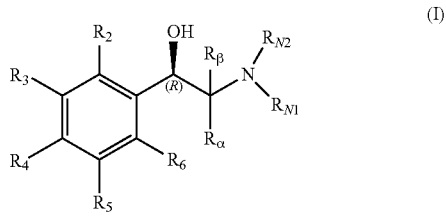

wherein R$_2$ is a group selected from: —H, —Cl, —Br, —I, —F, —CH$_3$, —OH, —OCH$_3$, —SH, —SCH$_3$, —NH$_2$, —NHCH$_3$, or a long chain alkyl; R$_3$ is a group selected from: —H, —Cl, —Br, —I, —F, —CH$_3$, —OH, —OCH$_3$, —SH, —SCH$_3$, —S(O)CH$_3$, —NH$_2$, —NHCH$_3$, —N(CH$_3$)$_2$, —OR, —SR, —NR$_2$, —SO$_2$NR$_2$ (wherein R=—H, —CH$_3$, or alkyl), ethyl, propyl, isopropyl, cyclopropyl, or a long chain alkyl; R$_4$ is a group selected from: —H, —Cl, —Br, —I, —F, —CH$_3$, —OH, —OCH$_3$, —SH, —SCH$_3$, —S(O)CH$_3$, —SO$_2$CH$_3$, —NH$_2$, —NHCH$_3$, —N(CH$_3$)$_2$, SO$_2$NR$_2$ (wherein R=—H, —CH$_3$); R$_5$ is a group selected from: —H, —Cl, —Br, —I, —F, —CH$_3$, —OH, —OCH$_3$, —SH, —SCH$_3$, —S(O)CH$_3$, —SO$_2$CH$_3$, —NH$_2$, —NHCH$_3$, —N(CH$_3$)$_2$, —OR, —SR, —NR$_2$, —SO$_2$NR$_2$ (wherein R=—H, —CH$_3$, or alkyl), ethyl, propyl, isopropyl, or cyclopropyl; R$_6$ is a group selected from: —H, —Cl, —Br, —I, —F, —CH$_3$, —OH, —SH, or —NH$_2$; wherein R$_2$ and R$_3$, R$_3$ and R$_4$, or R$_4$ and R$_5$ can optionally be connected as part of a 5 or 6 membered ring; wherein R$_\alpha$ is a group selected from: —H, —CH$_3$, ethyl, propyl, isopropyl, cyclopropyl, or a long chain alkyl; wherein R$_\beta$ is a group selected from: —H, —CH$_3$, ethyl, propyl, isopropyl, or cyclopropyl; wherein R$_\alpha$ and R$_\beta$ can form a ring, or wherein the R$_\alpha$-R$_\beta$ unit is a carbonyl or imino functional group; wherein R$_{N1}$ and R$_{N2}$ can be independently a group selected from: —H, —CH$_3$, —OH, —OCH$_3$, —OR, —C(O)R (wherein R=—H, —CH$_3$, or alkyl), ethyl, propyl, isopropyl, cyclopropyl, long chain alkyl, carbonyl, or carboxy.

In some embodiments of the method, the substrate compound of Formula II is 1-(3-hydroxyphenyl)-2-(methylamino)ethanone, compound (2), and the product of Formula I is compound (1), (R)-phenylephrine.

In another aspect, the disclosure provides polynucleotides encoding the engineered polypeptides described herein or polynucleotides that hybridize to such polynucleotides under highly stringent conditions. The polynucleotide can include promoters and other regulatory elements useful for expression of the encoded polypeptide having ketoreductase activity, and can utilize codons optimized for specific desired expression systems. Exemplary polynucleotides include, but are not limited to SEQ ID NO: 5, 7, 9, 11, 13, 15, 17, 19, 21, 23, 25, 27, 29, 31, and 33.

In another embodiment, the disclosure provides host cells comprising the polynucleotides and/or expression vectors described herein. The host cells may be prokaryotic or eukaryotic. In one embodiment, the host cell can be E. coli, or a different prokaryotic organism. In another embodiment, the host cell may be a yeast cell. The host cells can be used for the expression and isolation of the engineered polypeptides described herein, or, alternatively, they can be used directly for the conversion of the substrate to, for example, a phenylephrine product.

6. BRIEF DESCRIPTION OF THE FIGURES

FIG. 1 provides Table 8, which depicts Chromatographic Conditions, including chromatographic equipment, conditions, and analytical parameters.

7. DETAILED DESCRIPTION

As used herein and in the appended claims, the singular forms "a," "and," and "the" include plural referents unless the context clearly dictates otherwise. Thus, for example, reference to "a substrate" includes a plurality of such substrates and reference to "the enzyme" includes reference to one or more enzymes, and so forth.

Unless defined otherwise, all technical and scientific terms used herein have the same meaning as commonly understood to one of ordinary skill in the art to which this disclosure belongs. Although any methods and reagents similar or equivalent to those described herein can be used in the practice of the disclosed methods and compositions, the exemplary methods and materials are now described.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

All publications mentioned herein are incorporated herein by reference in full for the purpose of describing and disclosing the methodologies, which are described in the publications, which might be used in connection with the description herein. The publications discussed above and throughout the text are provided solely for their disclosure prior to the filing date of the present application. Nothing herein is to be construed as an admission that the inventors are not entitled to antedate such disclosure by virtue of prior disclosure.

Enzymes belonging to the ketoreductase (KRED) or carbonyl reductase class (EC1.1.1.184) have been found to be useful for the stereoselective conversion of pro-stereoisomeric aldehyde or ketone substrates to the corresponding chiral alcohol products. KREDs typically convert a ketone or aldehyde substrate to the corresponding alcohol product, but may also catalyze the reverse reaction, oxidation of an alcohol substrate to the corresponding ketone/aldehyde product. The reduction of ketones and aldehydes and the oxidation of alcohols by enzymes such as KRED requires a co-factor, most commonly reduced nicotinamide adenine dinucleotide (NADH) or reduced nicotinamide adenine dinucleotide phosphate (NADPH), and nicotinamide adenine dinucleotide (NAD) or nicotinamide adenine dinucleotide phosphate (NADP) for the oxidation reaction. NADH and NADPH serve as electron donors, while NAD and NADP serve as electron acceptors.

KREDs are increasingly being used for the stereoselective conversion of ketones and aldehydes to chiral alcohols compounds used in the production of key pharmaceutical compounds. Examples using KREDs to generate useful chemical compounds include asymmetric reduction of 4-chloroacetoacetate esters (Zhou, J. Am. Chem. Soc. 1983 105:5925-5926; Santaniello, J. Chem. Res. (S) 1984:132-133; U.S. Pat. Nos. 5,559,030; 5,700,670 and 5,891,685), reduction of dioxocarboxylic acids (e.g., U.S. Pat. No. 6,399,339), reduction of tert-butyl (S) chloro-5-hydroxy-3-oxohexanoate (e.g., U.S. Pat. No. 6,645,746 and WO 01/40450), reduction of pyrrolotriazine-based compounds (e.g., U.S. application No. 2006/0286646); reduction of substituted acetophenones (e.g., U.S. Pat. No. 6,800,477); and reduction of ketothiolanes (WO 2005/054491). In another approach, as demonstrated herein, the ketoreduction can be carried out in the presence of an alcohol, such as isopropanol, to provide a substrate for the reverse reaction (alcohol dehydrogenation). In this manner, the NADH/NADPH consumed in the ketoreduction reaction is regenerated by the reverse, oxidative reaction.

The disclosure relates to a polypeptide having ketoreductase activity. In one embodiment, the polypeptide having ketoreductase activity is derived from the organism *Lactobacillus kefir*.

A. Definitions

By "derived" means that the polypeptide is modified in its primary, secondary or tertiary structure to contain one or more amino acid substitutions, deletions or insertions, yet comprises at least 50% or more of the primary sequence of the ketoreductase of *L. kefir* (the parental protein, strand or polypeptide).

A "parent" protein, enzyme, polynucleotide, gene, or cell, is any protein, enzyme, polynucleotide, gene, or cell, from which any other protein, enzyme, polynucleotide, gene, or cell, is derived or made, using any methods, tools or techniques, and whether or not the parent is itself native or mutant. A parent polynucleotide or gene encodes for a parent protein or enzyme.

A "mutation" means any process or mechanism resulting in a mutant protein, enzyme, polynucleotide, gene, or cell relative to a parental protein, polynucleotide, gene, or cell. This includes any mutation in which a protein, enzyme, polynucleotide, or gene sequence is altered. Typically, the mutation will result in a detectable change in the biological activity of a cell, enzyme or polypeptide (e.g., enzyme stability, inhibition, turnover etc.). Typically, a mutation occurs in a polynucleotide or gene sequence, by point mutations, deletions, or insertions of single or multiple nucleotide residues. A mutation includes polynucleotide alterations arising within a protein-encoding region of a gene as well as alterations in regions outside of a protein-encoding sequence, such as, but not limited to, regulatory or promoter sequences. A mutation in a gene can be "silent", i.e., not reflected in an amino acid alteration upon expression, leading to a "sequence-conservative" variant of the gene. This generally arises when one amino acid corresponds to more than one codon.

Non-limiting examples of a modified amino acid include a glycosylated amino acid, a sulfated amino acid, a prenylated (e.g., farnesylated, geranylgeranylated) amino acid, an acetylated amino acid, an acylated amino acid, a pegylated amino acid, a biotinylated amino acid, a carboxylated amino acid, a phosphorylated amino acid, and the like. References adequate to guide one of skill in the modification of amino acids are replete throughout the literature. Example protocols are found in Walker (1998) Protein Protocols on CD-ROM (Humana Press, Towata, N.J.).

An "engineered polypeptide" refers to a polypeptide having a variant sequence generated by human manipulation (e.g., a sequence generated by directed evolution of a naturally occurring parent enzyme or of a variant previously derived from a naturally occurring enzyme). Typically, an engineered polypeptide is derived from a parental polypeptide having some degree of activity. The parental polypeptide may be a wild-type polypeptide obtained from an organism, or a previously derived engineered polypeptide. As disclosed herein, genes encoding engineered polypeptides can be cloned and subjected to further rounds of manipulation (e.g., directed evolution) to obtain another engineered polypeptide having a desired activity or substrate specificity. Thus, a parental polypeptide may be a ketoreductase enzyme that has previously undergone one or more rounds of manipulation to improve or modify the enzymes activity. The present disclosure provides engineered polypeptides having at least ketoreductase activity capable of converting compound (2) to compound (1), but they may have additional activity or substrate specificity.

"Protein," "polypeptide," and "peptide" are used interchangeably herein to denote a polymer of at least two amino acids covalently linked by an amide bond, regardless of length or post-translational modification (e.g., glycosylation, phosphorylation, lipidation, myristilation, ubiquitination, etc.). Included within this definition are D- and L-amino acids, and mixtures of D- and L-amino acids.

"Polynucleotides" or "oligonucleotides" refer to nucleobase polymers or oligomers in which the nucleobases are connected by sugar phosphate linkages (sugar-phosphate backbone). Nucleobase or base include naturally occurring and synthetic heterocyclic moieties commonly known to those who utilize nucleic acid or polynucleotide technology or utilize polyamide or peptide nucleic acid technology to thereby generate polymers that can hybridize to polynucleotides in a sequence-specific manner. Non-limiting examples of nucleobases include: adenine, cytosine, guanine, thymine, uracil, 5-propynyl-uracil, 2-thio-5-propynyl-uracil, 5-methylcytosine, pseudoisocytosine, 2-thiouracil and 2-thiothymine, 2-aminopurine, N9-(2-amino-6-chloropurine), N9-(2,6-diaminopurine), hypoxanthine, N9-(7-deaza-guanine), N9-(7-deaza-8-aza-guanine) and N8-(7-deaza-8-aza-adenine). Exemplary poly- and oligonucleotides include polymers of 2' deoxyribonucleotides (DNA) and polymers of ribonucleotides (RNA). A polynucleotide may be composed entirely of ribonucleotides, entirely of 2' deoxyribonucleotides or combinations thereof.

"Coding sequence" refers to that portion of a polynucleotide (e.g., a gene) that encodes a polypeptide.

"Naturally-occurring" or "wild-type" refers to the form found in nature. For example, a naturally occurring or wild-type polypeptide or polynucleotide sequence is a sequence present in an organism that can be isolated from a source in nature and which has not been intentionally modified by human manipulation. In one embodiment, the naturally occurring ketoreductase polypeptide used in the methods of the disclosure comprises a sequence as set forth in SEQ ID NO:2 and which is encoded by the polynucleotide of SEQ ID NO:1.

"Percentage of sequence identity," "percent identity," and "percent identical" are used herein to refer to comparisons between polynucleotide sequences or polypeptide sequences, and are determined by comparing two optimally aligned sequences over a comparison window, wherein the portion of the polynucleotide or polypeptide sequence in the comparison window may comprise additions or deletions (i.e., gaps) as compared to the reference sequence for optimal alignment of the two sequences. The percentage is calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Determination of optimal alignment and percent sequence identity is performed using the BLAST and BLAST 2.0 algorithms (see e.g., Altschul et al., 1990, *J. Mol. Biol.* 215: 403-410 and Altschul et al., 1977, *Nucleic Acids Res.* 3389-3402). Software for performing BLAST analyses is publicly available through the National Center for Biotechnology Information website.

Briefly, the BLAST analyses involve first identifying high scoring sequence pairs (HSPs) by identifying short words of length W in the query sequence, which either match or satisfy some positive-valued threshold score T when aligned with a word of the same length in a database sequence. T is referred to as, the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=-4, and a comparison of both strands. For amino acid sequences, the BLASTP program uses as defaults a wordlength (W) of 3, an expectation (E) of 10, and the BLOSUM62 scoring matrix (see Henikoff and Henikoff, 1989, *Proc Natl Acad Sci USA* 89:10915).

Other algorithms are available that function similarly to BLAST in providing percent identity for two sequences. Optimal alignment of sequences for comparison can be conducted, e.g., by the local homology algorithm of Smith and Waterman, 1981, *Adv. Appl. Math.* 2:482, by the homology alignment algorithm of Needleman and Wunsch, 1970, *J. Mol. Biol.* 48:443, by the search for similarity method of Pearson and Lipman, 1988, *Proc. Natl. Acad. Sci. USA* 85:2444, by computerized implementations of these algorithms (GAP, BESTFIT, FASTA, and TFASTA in the GCG Wisconsin Software Package), or by visual inspection (see generally, *Current Protocols in Molecular Biology*, F. M. Ausubel et al., eds., Current Protocols, a joint venture between Greene Publishing Associates, Inc. and John Wiley & Sons, Inc., (1995 Supplement) (Ausubel)). Additionally, determination of sequence alignment and percent sequence identity can employ the BESTFIT or GAP programs in the GCG Wisconsin Software package (Accelrys, Madison WI), using default parameters provided.

"Reference sequence" refers to a defined sequence to which an altered sequence is compared. A reference sequence may be a subset of a larger sequence, for example, a segment of a full-length gene or polypeptide sequence. Generally, a reference sequence is at least 20 nucleotide or amino acid residues in length, at least 25 residues in length, at least 50 residues in length, or the full length of the nucleic acid or polypeptide. Since two polynucleotides or polypeptides may each (1) comprise a sequence (i.e., a portion of the complete sequence) that is similar between the two sequences, and (2) may further comprise a sequence that is divergent between the two sequences, sequence comparisons between two (or more) polynucleotides or polypeptide are typically performed by comparing sequences of the two polynucleotides over a comparison window to identify and compare local regions of sequence similarity. The term "reference sequence" is not intended to be limited to wild-type sequences, and can include engineered or altered sequences. For example, in some embodiments, a reference sequence can be a previously engineered or altered amino acid sequence.

"Comparison window" refers to a conceptual segment of at least about 20 contiguous nucleotide positions or amino acids residues wherein a sequence may be compared to a reference sequence of at least 20 contiguous nucleotides or amino acids and wherein the portion of the sequence in the comparison window may comprise additions or deletions (i.e., gaps) of 20 percent or less as compared to the reference sequence (which does not comprise additions or deletions) for optimal alignment of the two sequences. The comparison window can be longer than 20 contiguous residues, and includes, optionally 30, 40, 50, 100, or longer windows.

"Substantial identity" refers to a polynucleotide or polypeptide sequence that has at least 80 percent sequence identity, at least 85 percent sequence identity, at least 89 percent sequence identity, at least 95 percent sequence identity, and even at least 99 percent sequence identity as compared to a reference sequence over a comparison window of at least 20 residue positions, frequently over a window of at least 30-50 residues, wherein the percentage of sequence identity is calculated by comparing the reference sequence to a sequence that includes deletions or additions which total 20 percent or less of the reference sequence over the window of comparison. In specific embodiments applied to polypeptides, the term "substantial identity" means that two polypeptide sequences, when optimally aligned, such as by the programs GAP or BESTFIT using default gap weights, share at least 80 percent sequence identity, preferably at least 89 percent sequence identity, at least 95 percent sequence identity or more (e.g., 99 percent sequence identity). Preferably, residue positions which are not identical differ by conservative amino acid substitutions.

"Stereoselectivity" or "stereospecificity" refer to the preferential formation in a chemical or enzymatic reaction of one stereoisomer over another. Stereoselectivity can be partial, where the formation of one stereoisomer is favored over the other, or it may be complete where only one stereoisomer is formed. When the stereoisomers are enantiomers, the stereoselectivity is referred to as enantioselectivity, the fraction (typically reported as a percentage) of one enantiomer in the sum of both. It is commonly alternatively reported in the art (typically as a percentage) as the enantiomeric excess (e.e.) calculated therefrom according to the formula (major enantiomer−minor enantiomer)/(major enantiomer+minor enantiomer). Where the stereoisomers are diastereoisomers, the stereoselectivity sometimes is referred to as diastereoselectivity, the fraction (typically reported as a percentage) of one diastereomer in a mixture of two diastereomers, commonly alternatively reported as the diastereomeric excess (d.e.). Enantiomeric excess and diastereomeric excess are types of stereomeric excess.

"Highly stereoselective" or "highly stereospecific" refers to a chemical or enzymatic reaction that is capable of preferentially converting a substrate to its corresponding product with at least 85% stereomeric excess.

"Improved enzyme property" refers to any enzyme property made better or more desirable for a particular purpose as compared to that property found in a reference enzyme. For an engineered polypeptide having ketoreductase activity described herein, the comparison is generally made to a wild-type ketoreductase enzyme (e.g., a *L. kefir* ketoreductase (KRED)), although in some embodiments, the reference ketoreductase can be another improved engineered ketoreductase. Enzyme properties for which improvement is desirable include, but are not limited to, enzymatic activity (which can be expressed in terms of percent conversion of the substrate in a period of time), thermal stability, pH stability or activity profile, cofactor requirements, refractoriness to inhibitors (e.g., product inhibition), stereospecificity, and stereoselectivity (including enantioselectivity). In some embodiments, a modified substrate specificity or product production (not normally produced by the wild-type enzyme) is an improved enzyme property.

"Increased enzymatic activity" or "increased activity" or "increased conversion rate" refers to an improved property of an engineered enzyme, which can be represented by an increase in specific activity (e.g., product produced/time/weight protein) or an increase in percent conversion of the substrate to the product (e.g., percent conversion of starting amount of substrate to product in a specified time period using a specified amount of a ketoreductase) as compared to a reference enzyme. Exemplary methods to determine enzyme activity and conversion rate are provided in the Examples. Any property relating to enzyme activity may be affected, including the classical enzyme properties of $K_m$, $V_{mm}$ or $k_{cat}$, changes of which can lead to increased enzymatic activity. Improvements in enzyme activity can be from about 100% improved over the enzymatic activity of the corresponding wild-type ketoreductase, to as much as 200%, 500%, 1000%, or more over the enzymatic activity of the naturally occurring ketoreductases or another engineered R-alcohol dehydrogenase from which an engineered polypeptide is derived. In specific embodiments, the engineered enzymes of the disclosure exhibits improved enzymatic activity in the range of a 100% to 200%, 200% to 1000% or more than a 1500% improvement over that of the parent, wild-type or other reference enzyme. It is understood by the skilled artisan that the activity of any enzyme is diffusion limited such that the catalytic turnover rate cannot exceed the diffusion rate of the substrate, including any required cofactors. Hence, any improvements in the enzyme activity of a ketoreductase will have an upper limit related to the diffusion rate of the substrates acted on by the ketoreductase. Ketoreductase activity can be measured by any one of standard assays used for measuring alcohol dehydrogenase activity, such as the assay condition described below. Comparisons of enzyme activities or conversion rates are made using a defined preparation of enzyme, a defined assay under a set condition, and one or more defined substrates, as further described in detail herein. Generally, when lysates are compared, the numbers of cells and/or the amount of protein assayed are determined as well as use of identical expression systems and identical host cells to minimize variations in amount of enzyme produced by the host cells and present in the lysates.

"Conversion" refers to the enzymatic transformation of a substrate to the corresponding product. "Percent conversion" refers to the percent of the substrate that is converted to the product within a period of time under specified conditions. Thus, for example, the "activity" or "conversion rate" of a ketoreductase polypeptide can be expressed as "percent conversion" of the substrate to the product.

"Thermostable" or "thermal stable" are used interchangeably to refer to a polypeptide that is resistant to inactivation when exposed to temperatures above ambient (e.g., 30-80° C.) for a period of time (e.g., 0.5-24 hrs) compared to the untreated enzyme, thus retaining a certain level of residual activity (more than 60% to 80% for example) after exposure to the elevated temperatures.

"Solvent stable" refers to a polypeptide that maintains similar activity (more than e.g., 60% to 80%) after exposure to varying concentrations (e.g., 5-99%) of solvent, (e.g., isopropyl alcohol, dimethylsulfoxide, tetrahydrofuran, 2-methyltetrahydrofuran, acetone, toluene, butylacetate, methyl tert-butylether, acetonitrile, etc.) for a period of time (e.g., 0.5-24 hrs) compared to the untreated enzyme.

"pH stable" refers to a polypeptide that maintains similar activity (more than e.g. 60% to 80%) after exposure to high or low pH (e.g. 8 to 12 or 4.5-6) for a period of time (e.g. 0.5-24 hrs) compared to the untreated enzyme.

"Thermo- and solvent stable" refers to a polypeptide that is both thermostable and solvent stable.

"Amino acid" or "residue" as used in context of the polypeptides disclosed herein refers to the specific monomer at a sequence position in a polypeptide or polymer of amino acids.

"Hydrophilic Amino Acid or Residue" refers to an amino acid or residue having a side chain exhibiting a hydrophobicity of less than zero according to the normalized consensus hydrophobicity scale of Eisenberg et al., 1984, *J. Mol. Biol.* 179:125-142. Genetically encoded hydrophilic amino acids include L-Thr (T), L-Ser (S), L-His (H), L-Glu (E), L-Asn (N), L-Gln (Q), L-Asp (D), L-Lys (K) and L-Arg (R).

"Acidic Amino Acid or Residue" refers to a hydrophilic amino acid or residue having a side chain exhibiting a pK value of less than about 6 when the amino acid is included in a peptide or polypeptide. Acidic amino acids typically have negatively charged side chains at physiological pH due to loss of a hydrogen ion. Genetically encoded acidic amino acids include L-Glu (E) and L-Asp (D).

"Basic Amino Acid or Residue" refers to a hydrophilic amino acid or residue having a side chain exhibiting a pK value of greater than about 6 when the amino acid is included in a peptide or polypeptide. Basic amino acids typically have positively charged side chains at physiological pH due to association with hydronium ion. Genetically encoded basic amino acids include L-Arg (R) and L-Lys (K).

"Polar Amino Acid or Residue" refers to a hydrophilic amino acid or residue having a side chain that is uncharged at physiological pH, but which has at least one bond in which the pair of electrons shared in common by two atoms is held more closely by one of the atoms. Genetically encoded polar amino acids include L-Asn (N), L-Gln (Q), L-Ser (S) and L-Thr (T).

"Hydrophobic Amino Acid or Residue" refers to an amino acid or residue having a side chain exhibiting a hydrophobicity of greater than zero according to the normalized consensus hydrophobicity scale of Eisenberg et al., 1984, *J. Mol. Biol.* 179:125-142. Genetically encoded hydrophobic amino acids include L-Pro (P), L-Ile (I), L-Phe (F), L-Val (V), L-Leu (L), L-Trp (W), L-Met (M), L-Ala (A) and L-Tyr (Y).

"Aromatic Amino Acid or Residue" refers to a hydrophilic or hydrophobic amino acid or residue having a side chain that includes at least one aromatic or heteroaromatic ring. Genetically encoded aromatic amino acids include L-Phe (F), L-Tyr (Y) and L-Trp (W). Although owing to the pKa of its heteroaromatic nitrogen atom L-His (H) it is sometimes classified as a basic residue, or as an aromatic residue as its side chain includes a heteroaromatic ring, herein histidine is classified as a hydrophilic residue or as a "constrained residue."

"Constrained amino acid or residue" refers to an amino acid or residue that has a constrained geometry. Herein, constrained residues include L-Pro (P) and L-His (H). Histidine has a constrained geometry because it has a relatively small imidazole ring. Proline has a constrained geometry because it also has a five membered ring.

"Non-polar Amino Acid or Residue" refers to a hydrophobic amino acid or residue having a side chain that is uncharged at physiological pH and which has bonds in which the pair of electrons shared in common by two atoms is generally held equally by each of the two atoms (i.e., the side chain is not polar). Genetically encoded non-polar amino acids include L-Gly (G), L-Leu (L), L-Val (V), L-Ile (I), L-Met (M) and L-Ala (A).

"Aliphatic Amino Acid or Residue" refers to a hydrophobic amino acid or residue having an aliphatic hydrocarbon side chain. Genetically encoded aliphatic amino acids include L-Ala (A), L-Val (V), L-Leu (L) and L-Ile (I).

"Cysteine" or amino acid L-Cysteine (C) is unusual in that it can form disulfide bridges with other L-Cys (C) amino acids or other sulfanyl- or sulfhydryl-containing amino acids. The "cysteine-like residues" include cysteine and other amino acids that contain sulfhydryl moieties that are available for formation of disulfide bridges. The ability of L-Cys (C) (and other amino acids with —SH containing side chains) to exist in a peptide in either the reduced free —SH or oxidized disulfide-bridged form affects whether L-Cys (C) contributes net hydrophobic or hydrophilic character to a peptide. While L-Cys (C) exhibits a hydrophobicity of 0.29 according to the normalized consensus scale of Eisenberg (Eisenberg et al., 1984, supra), it is to be understood that for purposes of the present disclosure L-Cys (C) is categorized into its own unique group.

"Small Amino Acid or Residue" refers to an amino acid or residue having a side chain that is composed of a total three or fewer carbon and/or heteroatoms (excluding the α-carbon and hydrogens). The small amino acids or residues may be further categorized as aliphatic, non-polar, polar or acidic small amino acids or residues, in accordance with the above definitions. Genetically-encoded small amino acids include L-Ala (A), L-Val (V), L-Cys (C), L-Asn (N), L-Ser (S), L-Thr (T) and L-Asp (D).

"Hydroxyl-containing Amino Acid or Residue" refers to an amino acid containing a hydroxyl (—OH) moiety. Genetically-encoded hydroxyl-containing amino acids include L-Ser (S), L-Thr (T) and L-Tyr (Y).

"Amino acid difference" or "residue difference" refers to a change in the residue at a specified position of a polypeptide sequence when compared to a reference sequence. For example, a residue difference at position S96L, where the reference sequence has a serine, refers to a change of the residue at position S96 to a leucine. As disclosed herein, an engineered polypeptide having ketoreductase activity can include one or more residue differences relative to a reference sequence, where multiple residue differences typically are indicated by a list of the specified positions where changes are made relative to the reference sequence (e.g., "one or more residue differences as compared to SEQ ID NO:2 at the following residue positions: I11, A64, T76, V95, S96, V99, E145, F147, V148, T152, L153, S159, Y190, D197, E200, A202, M206, Y249").

"Corresponding to," "reference to," or "relative to" when used in the context of the numbering of a given amino acid or polynucleotide sequence refers to the numbering of the residues of a specified reference sequence when the given amino acid or polynucleotide sequence is compared to the reference sequence. In other words, the residue number or residue position of a given polymer is designated with respect to the reference sequence rather than by the actual numerical position of the residue within the given amino acid or polynucleotide sequence. For example, a given amino acid sequence, such as that of an engineered polypeptide, can be aligned to a reference sequence by introducing gaps to optimize residue matches between the two sequences. In these cases, although the gaps are present, the numbering of the residue in the given amino acid or polynucleotide sequence is made with respect to the reference sequence to which it has been aligned.

"Position corresponding to" as used herein in the context of identifying the position of a residue difference (e.g., substitution) in an amino acid sequence of an engineered reductase refers to the equivalent position in the reference sequence and should not absolutely be limited by the numbering system. For example, an equivalent position aligns with the position in the reference despite having a different absolute numbering system. Thus, the present disclosure contemplates that "position corresponding to" refers to an equivalent residue position in another ketoreductase that may e.g., lack a starting Met residue, or include an N-terminal additions, or insertions, deletions, or other modifications elsewhere that result in a different absolute position number at an equivalent residue position. The engineered polypeptides of the present disclosure are described herein with reference to amino acid positions of *L. kefir* ketoreductase of SEQ ID NO:2, or with reference to another engineered ketoreductase, such as any of SEQ ID NO:4, 6, 8, 10, 12, 14, 16, 18, 20, 22, 24, 26, 28, 30, 32, or 34. The amino acid residue positions of these polypeptides are numbered beginning with the initiating methionine (M) residue as residue position 1. However, it is contemplated (and will be understood by the skilled artisan) that this initiating methionine residue may be removed by biological processing machinery, such as in a host cell or in vitro translation system, to generate a mature polypeptide lacking the initiating methionine residue numbered "position 1." Consequently, the term "residue difference at position corresponding to X of SEQ ID NO: 2" as used herein may refer to position X in *L. kefir* ketoreductase or to the equivalent position X-1 in a ketoreductase that has been processed so as to lack the starting methionine.

The polypeptide sequence position at which a particular amino acid or amino acid change ("residue difference") is present is sometimes described herein as "$X_n$", or "position n", where n refers to the residue position with respect to the reference sequence. A specific substitution mutation, which is a replacement of the specific residue in a reference sequence with a different specified residue may be denoted by the conventional notation "X(number)Y", where X is the single letter identifier of the residue in the reference sequence, "number" is the residue position in the reference sequence (e.g., the wild-type ketoreductase of SEQ ID NO:2), and Y is the single letter identifier of the residue substitution in the engineered sequence. In some embodiments disclosed herein, the amino residue difference corresponding to an amino acid position is denoted differently due to the different reference sequence although it corresponds to an equivalent position. For example, a "residue difference at SEQ ID NO: 2 position Y190" is equivalent to a "residue difference at SEQ ID NO: 4 position C190."

A "conservative" amino acid substitution (or mutation) refers to the substitution of a residue with a residue having a similar side chain, and thus typically involves substitution of the amino acid in the polypeptide with amino acids within the same or similar defined class of amino acids. As used herein, in some embodiments, conservative mutations do not include substitutions from a hydrophilic to hydrophilic, hydrophobic to hydrophobic, hydroxyl-containing to hydroxyl-containing, or small to small residue. Additionally, as used herein a conservative mutation can be a substitution from an aliphatic to an aliphatic, non-polar to non-polar, polar to polar, acidic to acidic, basic to basic, aromatic to aromatic, or constrained to constrained residue. Table 1 below shows exemplary conservative substitutions.

TABLE 1

Conservative Substitutions

| Residue | Possible Conservative Mutations |
| --- | --- |
| A, L, V, I | Other aliphatic (A, L, V, I) |
|  | Other non-polar (A, L, V, I, G, M) |
| G, M | Other non-polar (A, L, V, I, G, M) |
| D, E | Other acidic (D, E) |
| K, R | Other basic (K, R) |
| P, H | Other constrained (P, H) |
| N, Q, S,T | Other polar (N, Q, S, T) |
| Y, W, F | Other aromatic (Y, W, F) |
| C | None |

Thus, in certain embodiments, "conservative amino acid substitutions" of a listed polypeptide sequence (e.g., SEQ ID NOs: 2, 4, 6, 8, 10, 12, 14, 16, 18, 20, 22, 24, 26, 28, 30, 32, and 34) can include substitutions of a percentage, typically less than 30% (e.g., less than 20% or less than 10%), of the amino acid sequence with an amino acid of the same conservative substitution group. Accordingly, a conservatively substituted variant of a polypeptide of the disclosure can contain 100, 75, 50, 25, 15, 10, 9, 8, 7, 6, 5, 4, 3, 2, or 1 amino acids substituted with an amino acid of the same conservative substitution group.

"Conservative variants" are polypeptides in which one or more amino acid residues have been changed without altering the overall conformation and function of the polypeptide from which they are derived, including, but not limited to, conservative amino acid substitutions. Typically, a conservative variant has amino acid residue differences at positions other than those indicated as positions that are conserved. Accordingly, the percent amino acid sequence identity between an enzyme and a conservative variant of that enzyme having a similar function may vary and can be, for example, at least 30%, at least 50%, at least 70%, at least 80%, at least 90%, at least 95%, at least 98% or at least 99%.

"Non-conservative substitutions" of a polypeptide are those substitutions which are not characterized as a conservative substitution. For example, any substitution which crosses the bounds of the groups set forth above in Table 1. These include substitutions of basic or acidic amino acids for neutral amino acids, (e.g., Asp, Glu, Asn, or Gln for Val, Ile, Leu or Met), aromatic amino acid for basic or acidic amino acids (e.g., Phe, Tyr or Trp for Asp, Asn, Glu or Gln) or any other substitution not replacing an amino acid with a like amino acid. Basic side chains include lysine (K), arginine (R), histidine (H); acidic side chains include aspartic acid (D), glutamic acid (E); uncharged polar side chains include glycine (G), asparagine (N), glutamine (Q), serine (S), threonine (T), tyrosine (Y), cysteine (C); nonpolar side chains include alanine (A), valine (V), leucine (L), isoleucine (I), proline (P), phenylalanine (F), methionine (M), tryptophan (W); beta-branched side chains include threonine (T), valine (V), isoleucine (I); aromatic side chains include tyrosine (Y), phenylalanine (F), tryptophan (W), histidine (H).

A "Z" group (e.g., a group designated Z1, Z2, Z3, Z4, Z5, Z6, and Z7) as used herein refers to a specific set of amino acids that may substituted at a designated position in a polypeptide and which may include both conservative and non-conservative amino acid substitutions. For example, substitution at specific residues in a polypeptide can be restricted to the specific amino acids listed in a "Z" group. Z groups useful with the polypeptides of the present disclosure are listed below in Table 2.

TABLE 2

Z Groups used to identify groups for substitutions

| Z Group Designation | Amino Acids in Z Group |
| --- | --- |
| Z1 | alanine (A), leucine (L), isoleucine (I), and valine (V) |
| Z2 | alanine (A), valine (V), leucine (L), isoleucine (I), glycine (G), or methionine (M) |
| Z3 | lysine (K), or arginine (R) |
| Z4 | tyrosine (Y), phenylalanine (F), or tryptophan (W) |
| Z5 | asparagine (N), glutamine (Q), serine (S), or threonine (T) |
| Z6 | aspartic acid (D) and glutamic acid (E) |
| Z7 | proline (P) or histidine (H) |

Accordingly, a polypeptide provided herein can include amino acids that are "restricted" to particular amino acid substitutions. For example, residue differences at positions of SEQ ID NO: 4 corresponding to 11, 64, 76, 95, 96, 99, 145, 147, 148, 152, 153, 159, 190, 197, 200, 202, 206, or 249 can be restricted to specific substitutions set forth in any of groups Z1-Z7 as defined above in Table 2, and elsewhere in the specification. It is understood that not all of the identified restricted residues need be altered in the same polypeptide.

In some embodiments, the invention encompasses polypeptides where only about 70%, 75%, 80%, 85%, 90% or 95% of the restricted amino acid residues are altered in a given polypeptide.

The present disclosure also contemplates mutations based on locations or regions in the structure of the parent polypeptide. Accordingly, referring to Table 3, a variant of a parent polypeptide (e.g., SEQ ID NO: 2, 4, 6, 8, 10, 12, 14, 16, 18, 20, 22, 24, 26, 28, 30, 32, or 34) can include an amino acid substitution at a particular residue located in a region of the parent polypeptide where the location is identified as describe instable 3. Exemplary substitutions at each of the relevant locations are also identified in Table 3.

TABLE 3

Enzyme locations useful for substitutions

| Enzyme Location | Specific Mutation (relative to SEQ ID NO: 2) |
|---|---|
| Non active site; buried | I11L |
| Non active site; buried | A64V |
| Surface | T76I |
| Non active site; buried | V95M |
| Active site | S96L |
| Tetramer interface | V99L |
| Active site | E145A |
| Tetramer interface | F147L/I |
| Active site | V148I |
| Active site | T152A |
| Active site | L153M |
| Non active site; buried | S159T |
| Active site | Y190C/G |
| Surface | D197A |
| Active site | E200P |
| Active site | A202F |
| Active site | M206C |
| Active site | Y249F |

"Deletion" refers to modification to the polypeptide by removal of one or more amino acids from the parental or reference polypeptide. Deletions can comprise removal of 1 or more amino acids, 2 or more amino acids, 3 or more amino acids, 4 or more amino acids, 5 or more amino acids, 6 or more amino acids, 7 or more amino acids, 8 or more amino acids, 10 or more amino acids, 12 or more amino acids, 15 or more amino acids, or 20 or more amino acids, up to 10% of the total number of amino acids, or up to 20% of the total number of amino acids making up the reference enzyme while retaining enzymatic activity and/or retaining the improved properties of an engineered ketoreductase enzyme. Deletions can be directed to the internal portions and/or terminal portions of the polypeptide. In various embodiments, the deletion can comprise a continuous segment or can be discontinuous.

"Insertion" refers to modification to the polypeptide by addition of one or more amino acids from the reference polypeptide. In some embodiments, the engineered enzymes of the disclosure can comprise insertions of one or more amino acids to the naturally occurring ketoreductase polypeptide as well as insertions of one or more amino acids to other engineered polypeptides having ketoreductase activity. Insertions can be in the internal portions of the polypeptide, or to the carboxy or amino terminus. Insertions as used herein include fusion polypeptides as is known in the art. The insertion can be a contiguous segment of amino acids or separated by one or more of the amino acids in the naturally occurring polypeptide.

"Fragment" as used herein refers to a polypeptide that has an amino-terminal and/or carboxy-terminal deletion, but where the remaining amino acid sequence is identical to the corresponding positions in the sequence. Fragments can be at least 14 amino acids long, at least 20 amino acids long, at least 50 amino acids long or longer, and up to 70%, 80%, 90%, 95%, 98%, and 99% of a full-length polypeptide of the disclosure. In some embodiment, the fragment is biological active and may have one or more activities of the native or full length polypeptide. For example, a biologically active fragment of a polypeptide of the disclosure will comprise ketoreductase activity. The biological activity may not be identical (e.g., enzymatic activity may be different) relative to the full length polypeptide.

"Isolated polypeptide" or "isolated polynucleotide" refers to a polypeptide or polynucleotide which is substantially separated from other contaminants that naturally accompany it, e.g., protein, lipids, and polynucleotides. The term embraces polypeptides which have been removed or purified from their naturally-occurring environment or expression system (e.g., host cell or in vitro synthesis). The ketoreductase enzymes of the disclosure may be present within a cell, present in the cellular medium, or prepared in various forms, such as lysates or isolated preparations.

"Substantially pure polypeptide" refers to a composition in which the polypeptide species is the predominant species present (e.g., on a molar or weight basis it is more abundant than any other individual macromolecular species in the composition), and is generally a substantially purified composition when the object species comprises at least about 50 percent of the macromolecular species present by mole or % weight. Generally, a substantially pure enzyme preparation will comprise about 60% or more, about 70% or more, about 80% or more, about 90% or more, about 95% or more, and about 98% or more of all macromolecular species by mole or % weight present in the composition. In some embodiments, the object species is purified to essential homogeneity (i.e., contaminant species cannot be detected in the composition by conventional detection methods) wherein the composition consists essentially of a single macromolecular species. Solvent species, small molecules (<500 Daltons), and elemental ion species are not considered macromolecular species.

"Stringent hybridization" is used herein to refer to conditions under which nucleic acid hybrids are stable. As known to those of skill in the art, the stability of hybrids is reflected in the melting temperature ($T_m$) of the hybrids. In general, the stability of a hybrid is a function of ionic strength, temperature, G/C content, and the presence of chaotropic agents. The $T_m$ values for polynucleotides can be calculated using known methods for predicting melting temperatures (see, e.g., Baldino et al., *Methods Enzymology* 168:761-777; Bolton et al., 1962, *Proc. Natl. Acad. Sci. USA* 48:1390; Bresslauer et al., 1986, *Proc. Natl. Acad. Sci USA* 83:8893-8897; Freier et al., 1986, *Proc. Natl. Acad. Sci USA* 83:9373-9377; Kierzek et al., *Biochemistry* 25:7840-7846; Rychlik et al., 1990, *Nucleic Acids Res* 18:6409-6412 (erratum, 1991, *Nucleic Acids Res* 19:698); Sambrook et al., supra); Suggs et al., 1981, In *Developmental Biology Using Purified Genes* (Brown et al., eds.), pp. 683-693, Academic Press; and Wetmur, 1991, *Crit Rev Biochem Mol Biol* 26:227-259. All publications incorporate herein by reference). In some embodiments, the polynucleotide encodes the polypeptide disclosed herein and hybridizes under defined conditions, such as moderately stringent or highly stringent conditions, to the complement of a sequence encoding an engineered polypeptide having ketoreductase activity.

"Hybridization stringency" relates to such washing conditions of nucleic acids. Generally, hybridization reactions are performed under conditions of lower stringency, followed by washes of varying but higher stringency. The term "moderately stringent hybridization" refers to conditions that permit target-DNA to bind a complementary nucleic acid that has about 60% identity, preferably about 75% identity, about 85% identity to the target DNA, with greater than about 90% identity to target-polynucleotide. "High stringency hybridization" refers generally to conditions that are about 10° C. or less from the thermal melting temperature $T_m$ as determined under the solution condition for a defined polynucleotide sequence. In some embodiments, a high stringency condition refers to conditions that permit hybridization of only those nucleic acid sequences that form stable hybrids in 0.018M NaCl at 65° C. (i.e., if a hybrid is not stable in 0.018M NaCl at 65° C., it will not be stable under high stringency conditions, as contemplated herein). Exemplary moderately stringent conditions are conditions equivalent to hybridization in 50% formamide, 5× Denhart's solution, 5×SSPE, 0.2% SDS at 42° C., followed by washing in 0.2×SSPE, 0.2% SDS, at 42° C. Exemplary high stringency conditions can be provided, for example, by hybridization in conditions equivalent to 50% formamide, 5× Denhart's solution, 5×SSPE, 0.2% SDS at 42° C., followed by washing in 0.1×SSPE, and 0.1% SDS at 65° C. Another high stringency condition is hybridizing in conditions equivalent to hybridizing in 5×SSC containing 0.1% (w:v) SDS at 65° C. and washing in 0.1×SSC containing 0.1% SDS at 65° C. Other high stringency hybridization conditions, as well as moderately stringent conditions, are described in the references cited above.

"Codon optimized" refers to changes in the codons of the polynucleotide encoding a protein to those preferentially used in a particular organism such that the encoded protein is efficiently expressed in the organism of interest. Although the genetic code is degenerate in that most amino acids are represented by several codons, called "synonyms" or "synonymous" codons, it is well known that codon usage by particular organisms is nonrandom and biased towards particular codon triplets. This codon usage bias may be higher in reference to a given gene, genes of common function or ancestral origin, highly expressed proteins versus low copy number proteins, and the aggregate protein coding regions of an organism's genome. In some embodiments, the polynucleotides encoding a polypeptide having ketoreductase activity of the disclosure may be codon optimized for optimal production from the host organism selected for expression.

"Preferred, optimal, high codon usage bias codons" refers interchangeably to codons that are used at higher frequency in the protein coding regions than other codons that code for the same amino acid. The preferred codons may be determined in relation to codon usage in a single gene, a set of genes of common function or origin, highly expressed genes, the codon frequency in the aggregate protein coding regions of the whole organism, codon frequency in the aggregate protein coding regions of related organisms, or combinations thereof. Codons whose frequency increases with the level of gene expression are typically optimal codons for expression. A variety of methods are known for determining the codon frequency (e.g., codon usage, relative synonymous codon usage) and codon preference in specific organisms, including multivariate analysis, for example, using cluster analysis or correspondence analysis, and the effective number of codons used in a gene (see GCG CodonPreference, Genetics Computer Group Wisconsin Package; CodonW, John Peden, University of Nottingham; McInerney, J. O, 1998, Bioinformatics 14:372-73; Stenico et al., 1994, Nucleic Acids Res. 222437-46; Wright, F., 1990, Gene 87:23-29). Codon usage tables are available for a growing list of organisms (see for example, Wada et al., 1992, Nucleic Acids Res. 20:2111-2118; Nakamura et al., 2000, Nucl. Acids Res. 28:292; Duret, et al., supra; Henaut and Danchin, "Escherichia coli and Salmonella," 1996, Neidhardt, et al. Eds., ASM Press, Washington D.C., p. 2047-2066. The data source for obtaining codon usage may rely on any available nucleotide sequence capable of coding for a protein. These data sets include nucleic acid sequences actually known to encode expressed proteins (e.g., complete protein coding sequences-CDS), expressed sequence tags (ESTS), or predicted coding regions of genomic sequences (see for example, Mount, D., Bioinformatics: Sequence and Genome Analysis, Chapter 8, Cold Spring Harbor Laboratory Press, Cold Spring Harbor, N.Y., 2001; Uberbacher, E. C., 1996, Methods Enzymol. 266:259-281; Tiwari et al., 1997, Comput. Appl. Biosci. 13:263-270).

"Control sequence" refers to all components that are necessary or advantageous for the expression of a polynucleotide and/or polypeptide of interest. Each control sequence may be native or foreign to a polynucleotide encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

"Operably linked" refers to a configuration in which a control sequence is appropriately placed at a position relative to a polynucleotide (e.g., in a functional relationship) such that the control sequence directs or regulates the expression of a polynucleotide and/or polypeptide.

"Promoter sequence" refers to a nucleic acid sequence that is recognized by a host cell for expression of a polynucleotide of interest (e.g., a coding region). The control sequence may comprise an appropriate promoter sequence. The promoter sequence contains transcriptional control sequences, which mediate the expression of the polypeptide. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

B. Engineered Polypeptides

The disclosure provides engineered polypeptides capable of facilitating the interconversion of alcohols and ketones with the reduction of a cofactor (e.g., NAD+ to NADH or NADP+ to NADPH). In one embodiment, the disclosure provides polypeptides that enantiospecifically catalyze the synthesis of phenylephrine from an appropriate substrate or intermediate.

The stereospecific engineered polypeptides comprising ketoreductase activity of the present disclosure are capable of converting the substrate 1-(3-hydroxyphenyl)-2-(methylamino)ethanone (compound (2)) to R-phenylephrine (compound (1)) (as shown in Scheme 1) with an improved property as compared to the naturally occurring, wild-type ketoreductase from *L. kefir*, represented by SEQ ID NO:2.

Scheme 1

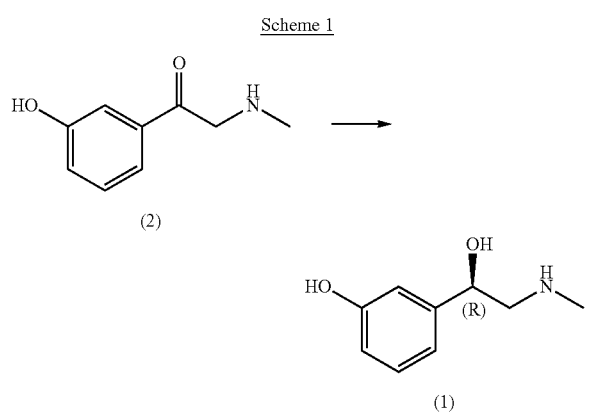

The polypeptides of the disclosure are characterized by an improved property as compared to the naturally occurring, wild-type ketoreductase from *L. kefir*, represented by SEQ ID NO:2. Enzyme properties for which improvement is desirable include, but are not limited to, enzymatic activity, thermal stability, pH activity/stability profile, refractoriness to inhibitors (e.g., product inhibition), stereospecificity, product purity, and solvent stability. The improvements in the ketoreductase enzyme can relate to a single enzyme property, such as pH stability/activity, or a combination of different enzyme properties, such as enzymatic activity and pH stability.

In some embodiments, the improved property of the polypeptides of the disclosure is with respect to an increase in enzymatic activity at a reaction condition of pH 6.75 to about 7.0 at 30° C. In one embodiment, the reaction is started at a pH of about 7.0 and decreased to a pH of about 6.75 after 2 hours. In a further embodiment, the pH is held at about 6.75 from about 2 hours to about 24 hours or until the reaction is substantially completed or the substrate is depleted. Improvements in enzymatic activity can be at least 1.2-fold, 1.5-fold, 2-fold, 3-fold, 5-fold, 10-fold or more greater than the ketoreductase activity of a reference ketoreductase, such as the polypeptide of SEQ ID NO: 2 or an engineered ketoreductase of SEQ ID NO:4, 6, 8, 10, 12, 14, 16, 18, 20, 22, 24, 26, 28, 30, 32, or 34 under the defined condition.

In some embodiments, the improved property of the ketoreductase polypeptide is with respect to an increase in pH stability under defined conditions relative to a reference ketoreductase (e.g., SEQ ID NO:4). In some embodiments, the pH stability can be reflected in enzymatic activity at an acidic pH (e.g., about pH 6.5-7.0), where the differences in enzymatic activity can be at least 1.5-fold, 2-fold, 3-fold, 5-fold, 10-fold, or more than the activity displayed by the polypeptide of SEQ ID NO:2, or an engineered ketoreductase of SEQ ID NO: 4, 6, 8, 10, 12, 14, 16, 18, 20, 22, 24, 26, 28, 30, 32, or 34 under the same defined acidic pH conditions.

In some embodiments, the improved enzymatic activity of the ketoreductase polypeptides of the disclosure can be an increase in the conversion rate of a substrate to product, such as improved conversion of compound (2) (1-(3-hydroxyphenyl)-2-(methylamino)ethanone) to the compound (1) ((R)-phenylephrine) under a defined condition. In some embodiments, the defined condition comprises 100 g/L of compound (2) under reaction conditions of pH of about 6.5-7.0 and about 30° C. in a reaction time of about 20-25 hrs with about with 0.7-1.0 g/L of a ketoreductase polypeptide of the disclosure.

In some embodiments, the engineered ketoreductase polypeptides are capable of conversion rate for converting compound (2) to compound (1) of at least about 50%, 60%, 70%, 75%, 80%, 85%, 90%, 91%, 92%, 93%, 94%, 95%, 96%, 97% 98%, 99%, or more up to the theoretical value of 100% conversion of substrate to the desired product under the defined condition.

In some embodiments, the improved ketoreductase is with respect to the conversion rate at a defined alkaline reaction condition. In some embodiments, the reaction condition comprises 100 g/L of the substrate of compound (2) under reaction conditions of pH of about 7.0 decreasing to 6.75 over about 2 hours and a temperature of about 30° C. in a reaction time of about 20-25 hours (e.g., 15, 16, 17, 18, 19, 20, 21, 22, 23, 24, or 25 hours) with about 0.7 to about 1.0 g/L of a ketoreductase polypeptide of the disclosure. In one embodiment, the reaction is started at a pH of about 7.0 and decreased to a pH of about 6.75 after 2 hours. In a further embodiment, the pH is held at about 6.75 from about 2 hours to about 24 hours or until the reaction is substantially completed or the substrate is depleted.

In some embodiments, the improved property of the engineered ketoreductase polypeptide is with respect to an increase in enantiomeric excess of (R)-phenylephrine produced by the polypeptide. In some embodiments, an enantiomeric excess of at least 99%, 99.1%, 99.2%, 99.3%, 99.4%, 99.5%, 99.6%, 99.7%, 99.8%, or 99.9% or more of the (R)-phenylephrine is produced.

In some embodiments, an improved property of the engineered ketoreductase is with respect to a decrease in non-enzymatic decomposition products formed in the conversion of a substrate of compound (2) having to a product of compound (1) as compared to the amount of decomposition product formed by a reference ketoreductase, such as the polypeptide of SEQ ID NO: 2 or 4.

In some embodiments, the amount of decomposition product is reduced by at least 25% as compared to the wild-type enzyme of SEQ ID NO: 2 or another engineered ketoreductase, such as SEQ ID NO: 4. In some embodiments, the amount of decomposition product is reduced by at least 50%, 60%, 75%, 80%, 85%, 90% or 95% or more as compared to the wild-type enzyme of SEQ ID NO:2 or another engineered ketoreductase, such as SEQ ID NO:4.

In some embodiments, an engineered ketoreductase polypeptide of the disclosure can comprise an amino acid sequence that has at least about 85%, 86%, 87%, 88%, 89%, 90%, 91%, 92%, 93%, 94%, 95%, 96%, 97%, 98%, 99% or more identity as compared to a reference sequence based on SEQ ID NO:2 having at the residue corresponding to I11, A64, T76, S96, V148 a Z1 amino acid; at the residue corresponding to V95, V99, E145, F147, T152, L153, Y190, D197 a Z2 amino acid; at the residue corresponding to A202 and Y249 a Z4 amino acid; at a residue corresponding to S159 a Z5 amino acid; at a residue corresponding to E200 a Z7 amino acid; and at a residue corresponding to M206 a cysteine amino acid; and wherein the polypeptides has ketoreductase activity.

In some embodiments, the improved ketoreductase polypeptides herein can comprise an amino acid sequence that has at least about 85%, 86%, 87%, 88%, 89%, 90%, 91%, 92%, 93%, 94%, 95%, 96%, 97%, 98%, 99% or more identity as compared to a reference sequence based on SEQ ID NO:4, 6, 8, 10, 12, 14, 16, 18, 20, 22, 24, 26, 28, 30, 32, or 34 wherein the residues corresponding to I11, A64, T76, V95, S96, V99, E145, A145, F147, L147, V148, T152, L153, S159, Y190, D197, E200, A202, M206, Y249 are not substituted and wherein the polypeptide has ketoreductase activity.

In some embodiments, the improved ketoreductase polypeptides can have residue differences in one or more residue positions as compared to the sequence of SEQ ID NO: 2 at residue positions corresponding to the following: I11, A64, T76, V95, S96, V99, E145, F147, V148, T152, L153, S159, Y190, D197, E200, A202, M206, Y249. In some embodiments, the residue differences comprise at positions corresponding to I11, A64, T76, S96, V148 a Z1 amino acid; at the residue corresponding to V95, V99, E145, F147, T152, L153, Y190, D197 a Z2 amino acid; at the residue corresponding to A202 and Y249 a Z4 amino acid; at a residue corresponding to S159 a Z5 amino acid; at a residue corresponding to E200 a Z7 amino acid. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40, 1-45, 1-50, 1-55, or 1-60 residue differences at other amino acid residue positions. In some embodiments, the number of differences can be 1, 2, 3, 4, 5, 6, 7, 8, 9, 10, 11, 12, 14, 15, 16, 18, 20, 22, 24, 26, 30, 35, 40, 45, 50, 55, or 60 residue differences at the other amino acid residue positions. In some embodiments, the residue differences at other residue positions comprise conservative mutations.

In some embodiments, the improved ketoreductase polypeptide comprises an amino acid sequence comprising SEQ ID NO:2 and having amino acid substitution(s) selected from the group consisting of at positions corresponding to: (i) I11 a Z1 amino acid; (ii) A64 a Z1 amino acid; (iii) T76 a Z1 amino acid; (iv) S96 a Z1 amino acid; (v) V148 a Z1 amino acid; (vi) V95 a Z2 amino acid; (vii) V99 a Z2 amino acid (viii) E145 a Z2 amino acid (ix) F147 a Z2 amino acid (x) T152 a Z2 amino acid; (xi) L153 a Z2 amino acid; (xii) Y190 a Z2 amino acid; (xiii) D197 a Z2 amino acid; (xiv) A202 a Z4 amino acid (xv) Y249 a Z4 amino acid; (xvi) S159 a Z5 amino acid; (xvii) E200 a Z7 amino acid; (xviii) M206 a cysteine; (xix) any combination of the foregoing; and (xx) 2 or 3, 3 or 4, 5 or 6, 7 or 8, 9 or 10, 11 or 12, 13 or 14, 14 or 15, 16 or 17, 2-4, 2-5, 2-6, 2-7, 2-8, 2-9, 2-10, 2-11, 2-12, 2-13, 2-14, 2-15, 2-16, 2-17, or 2-18 combinations of any of the foregoing substitutions. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40, 1-45, 1-50, 1-55, or 1-60 residue differences at other residue positions specifically described above. In some embodiments, the number of differences can be 1, 2, 3, 4, 5, 6, 7, 8, 9, 10, 11, 12, 14, 15, 16, 18, 20, 22, 24, 26, 30, 35, 40, 45, 50, 55, or 60 residue differences at the other residue positions. In some embodiments, the residue differences at other residue positions comprise conservative mutations.

Amino acid residue differences at other residue positions as compared to the wild-type L. kefir ketoreductase sequence of SEQ ID NO: 2 (Genbank acc. No. AAP94029.1; GI: 33112056) and the affect of these differences on enzyme function are provide by e.g., engineered ketoreductase polypeptides in the following patent publications, each of which is hereby incorporated by reference herein: U.S. Pat. Publ. Nos. 20080318295A1, 20090093031A1, 20090155863A1, 20090162909A1, 20090191605A1, 20100055751A1, and 20100062499A1; or PCT Publ. Nos. WO/2010/025238A2 and WO/2010/025287A1. Accordingly, in some embodiments, one or more of the amino acid differences provided in the engineered ketoreductase polypeptides of these publications could also be introduced into an engineered ketoreductase polypeptide of the present disclosure.

In some embodiments, the engineered ketoreductase polypeptide can comprise an amino acid sequence that is at least about 85%, 86%, 87%, 88%, 89%, 90%, 91%, 92%, 93%, 94%, 95%, 96%, 97%, 98%, 99% identical to a reference amino acid sequence based on SEQ ID NO:2 having the features described herein for the residues corresponding to T2, I11, A64, T76, V95, S96, V99, E145, F147, V148, T152, L153, S159, Y190, D197, E200, A202, M206, Y249 with the proviso that the engineered ketoreductase polypeptides have at the residues corresponding to T2, I11, A64, T76, V95, S96, V99, E145, F147, V148, T152, L153, S159, Y190, D197, E200, A202, M206, Y249 at least the preceding features (e.g., combination of residue differences found in any one of SEQ ID NO: 4, 6, 8, 10, 12, 14, 16, 18, 20, 22, 24, 26, 28, 30, 32, or 34).

In specific embodiments, the substitutions at residues of SEQ ID NO: 2 corresponding to I11, A64, T76, V95, S96, V99, E145, F147, V148, T152, L153, S159, Y190, D197, E200, A202, M206, Y249 comprise I11L, A64V, T76I, V95M, S96L, V99L, E145A, F147L, F147I, V148I, T152A, L153M, S159T, Y190C, Y190G, D197A, E200P, A202F, M206C, and Y249F.

Table 4 below lists engineered ketoreductase polypeptides (and encoding polynucleotides) by sequence identifier (SEQ ID NO) disclosed herein together with the specific residue differences of the engineered polypeptides with respect to the wild-type L. kefir ketoreductase polypeptide sequence (SEQ ID NO:2) from which they were derived by directed evolution (see e.g., Stemmer et al., 1994, Proc Natl Acad Sci USA 91:10747-10751). Each row of Table 4 lists two SEQ ID NOs, where the odd number refers to the nucleotide sequence that encodes for the polypeptide amino acid sequence provided by the even number.

The activity of each engineered ketoreductase polypeptide was determined relative to the engineered polypeptide SEQ ID NO: 4, which was used as the "parent" or "backbone" polypeptide for the directed evolution. Fold Improvement Over Parent ("FIOP") of activity was determined as conversion of 1-(3-hydroxyphenyl)-2-(methylamino)ethanone to (R)-phenylephrine at pH 6.5 and ambient temperature over 18-20 hours in the presence of NADP, as described in the Examples below.

The relative activity of the WT polypeptide of SEQ ID NO: 2 for the conversion of 1-(3-hydroxyphenyl)-2-(methylamino)ethanone to (R)-phenylephrine at pH 6.5 and ambient temperature was about 7% to about 10% of that of the engineered "backbone" polypeptide of SEQ ID NO: 4. Based on this ~10-fold greater relative activity of SEQ ID NO: 4 compared to WT, relative activities compared to WT for the engineered polypeptides of SEQ ID NOs: 6, 8, 10, 12, 14, 16, 18, 20, 22, 24, 26, 28, 30, 32, and 34, was calculated by multiplying by 10 the FIOP value relative to SEQ ID NO:4. These relative activities were quantified as follows: "+" indicates that the engineered ketoreductase activity is from 10-fold to 75-fold greater than the activity of the polypeptide of the WT (SEQ ID NO:2); "++" indicates that the engineered ketoreductase activity is from 75-fold to about 750-fold greater than the activity of WT (SEQ ID NO:2); and "+++" indicates that the engineered ketoreductase activity is from 750-fold to about 1600-fold greater than the activity of WT (SEQ ID NO:2).

TABLE 4

Ketoreductase polypeptides, specific residue differences, and relative activities for converting compound (2) to compound (1)

| SEQ ID NO: (nt/aa) | Residue Differences (relative to SEQ ID NO: 2) | No. of coding mutations compared to WT | FIOP (SEQ ID NO: 4) | Relative activity compared to WT |
|---|---|---|---|---|
| 1/2 | — | — | — | — |
| 3/4 | E145A; F147L; Y190C; | 3 | 1 | + |
| 5/6 | V95M; E145A; F147L; Y190C; A202F; M206C | 6 | 7.3 | + |
| 7/8 | V95M; E145A; F147L; Y190G; A202F; M206C | 6 | 14.6 | ++ |
| 9/10 | V95M; S96L; E145A; F147L; Y190G; A202F; M206C; Y249F | 8 | 29.2 | ++ |
| 11/12 | T2S; T76I; V95M; S96L; E145A; F147L; V148I; Y190G; A202F; M206C; Y249F | 11 | 46.7 | ++ |
| 13/14 | T76I; V95M; S96L; E145A; F147L; V148I; T152A; L153M; Y190G; A202F; M206C; Y249F | 12 | 74.75 | ++ |
| 15/16 | A64V; T76I; V95M; S96L; V99L; E145A; F147L; V148I; T152A; L153M; S159T; Y190G; D197A; E200P; A202F; M206C; Y249F | 17 | 112.1 | +++ |
| 17/18 | I11L; A64V; T76I; V95M; S96L; V99L; E145A; F147L; V148I; T152A; L153M; S159T; Y190G; D197A; E200P; A202F; M206C; Y249F | 18 | 134.6 | +++ |
| 19/20 | I11L; A64V; T76I; V95M; S96L; V99L; E145A; F147I; V148I; T152A; L153M; S159T; Y190G; D197A; E200P; A202F; M206C; Y249F | 18 | 161.5 | +++ |
| 21/22 | V95M; E145A; F147L; Y190C; | 4 | 1.4 | + |
| 23/24 | E145A; F147L; Y190C; M206C | 4 | 1.6 | + |
| 25/26 | E145A; F147L; Y190C; A202F | 4 | 2.9 | + |
| 27/28 | V95M; E145A; F147L; Y190C; A202F | 5 | 5.0 | + |
| 29/30 | V95M; E145A; F147L; Y190C; A202F; M206C; Y249F | 7 | 11.9 | ++ |
| 31/32 | V95M; E145A; F147L; Y190G; A202F; M206C; Y249F | 7 | 26.3 | ++ |
| 33/34 | T2S; V95M; E145A; F147L; Y190G; A202F; M206C; | 7 | 19.0 | ++ |

In some embodiments, the engineered ketoreductase polypeptide can comprise an amino acid sequence that is at least 70%, 75%, 80%, 81%, 82%, 83%, 84%, 85%, 86%, 87%, 88%, 89%, 90%, 91%, 92%, 93%, 94%, 95%, 96%, 97%, 98%, or 99% identical to a reference amino acid sequence of any one of SEQ ID NO:4, 6, 8, 10, 12, 14, 16, 18, 20, 22, 24, 26, 28, 30, 32, or 34 and wherein the amino acids at the positions of residue differences indicated in Table 4 (above) are unchanged and the polypeptide has ketoreductase activity. Accordingly, in some embodiments, the engineered polypeptides are capable of converting 1-(3-hydroxyphenyl)-2-(methylamino)ethanone to (R)-phenylephrine and comprise an amino acid sequence at least about 70% identical to SEQ ID NO: 4 and further comprise the combination of residue differences of any one of SEQ ID NO: 6, 8, 10, 12, 14, 16, 18, 20, 22, 24, 26, 28, 30, 32, or 34 as compared to SEQ ID NO: 2.

In some embodiments, these engineered polypeptides can have additionally (i.e., in addition to the mutations residue differences shown in Table 4) from about 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40, 1-45, 1-50, 1-55, or 1-60 residue differences as compared to the reference sequence. In some embodiments, the number of residue differences can be 1, 2, 3, 4, 5, 6, 7, 8, 9, 10, 11, 12, 14, 15, 16, 18, 20, 22, 24, 26, 30, 35, 40, 45, 50, 55, or 60 differences as compared to the reference sequence. The residue differences can comprise insertions, deletions, or substitutions, or combinations thereof. In some embodiments, the residue differences comprise conservative substitutions as compared to the references sequence.

In some embodiments, an engineered ketoreductase polypeptide comprises an amino acid sequence corresponding to SEQ ID NO: 4, 6, 8, 10, 12, 14, 16, 18, 20, 22, 24, 26, 28, 30, 32, or 34.

In some embodiments, the ketoreductase polypeptide is capable of stereospecifically converting 1-(3-hydroxyphenyl)-2-(methylamino)ethanone to (R)-phenylephrine under reaction conditions of pH of about 7.0 (decreasing to 6.75 over about 2 hours) and a temperature of about 30° C. in a reaction time of about 20-25 hours hrs with about 0.7 to about 1.0 g/L of an a ketoreductase polypeptide of the disclosure. In one embodiment, the reaction is started at a pH of about 7.0 and decreased to a pH of about 6.75 after 2 hours. In a further embodiment, the pH is held at about 6.75 from about 2 hours to about 24 hours or until the reaction is substantially completed or the substrate is depleted. In some embodiments, the ketoreductase polypeptide capable of stereospecifically converting at least 80%, 85%, 90%, 91%, 92%, 93%, 94%, 95%, 96%, 97%, 98%, 99%, or more of 1-(3-hydroxyphenyl)-2-(methylamino)ethanone to (R)-phenylephrine under reaction conditions of pH of about 7.0 (decreasing to about 6.75) and about 30° C. in about 20-24 hrs comprises an amino acid sequence selected from SEQ ID NO: 4, 6, 8, 10, 12, 14, 16, 18, 20, 22, 24, 26, 28, 30, 32, or 34.

In some embodiments, an engineered ketoreductase enzyme can comprise deletions of 1-20 amino acids typically at the N-terminal or C-terminal end. Thus, for each and every embodiment of the ketoreductase polypeptides of the disclosure, the deletions can comprise one or more amino acids, 2 or more amino acids, 3 or more amino acids, 4 or more amino acids, 5 or more amino acids, 6 or more amino acids, 8 or more amino acids, 10 or more amino acids, 15 or more amino acids, or 20 or more amino acids, up to 10% of the total number of amino acids, up to 20% of the total number of amino acids, or up to 30% of the total number of amino acids of the ketoreductase polypeptides, so long as the functional activity of the ketoreductase activity is maintained. In some embodiments, the number of deletions can be 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40, 1-45, 1-50, 1-55, or 1-60 amino acids. In some embodiments, the number of deletions can be 1, 2, 3, 4, 5, 6, 7, 8, 9, 10, 11, 12, 13, 14, 15, 16, 18, 20, 22, 24, 26, 29 or 30 amino acid residues.

In some embodiments, the present disclosure provides an engineered polypeptide capable of converting compound (2) to compound (1) with at least 1.2-fold, at least 1.5-fold, at least 2-fold, at least 3-fold, at least 5-fold, at least 10-fold, at least 25-fold, at least 40-fold, at least 60-fold, or greater increased activity relative to the activity of the polypeptide of SEQ ID NO: 2 or 4, which comprises an amino acid sequence having at least 80%, 85%, 86%, 87%, 88%, 89%, 90%, 91%, 92%, 93%, 94%, 95%, 96%, 97%, 98%, or 99% identity to a reference polypeptide of SEQ ID NO: 2 or 4, with the proviso that the amino acid sequence of any one or more of the ketoreductase polypeptides disclosed in any one or more of the following patent publications are excluded: U.S. Pat. Publ. Nos. 20080318295A1, 20090093031A1, 20090155863A1, 20090162909A1, 20090191605A1, 20100055751A1, and 20100062499A1; or PCT Publ. Nos. WO/2010/025238A2 and WO/2010/025287A1.

In some embodiments, the polypeptides described herein are not restricted to the genetically encoded amino acids and may be comprised, either in whole or in part, of naturally-occurring and/or synthetic non-encoded amino acids. Certain commonly encountered non-encoded amino acids of which the polypeptides described herein may be comprised include, but are not limited to: the D-stereoisomers of the genetically-encoded amino acids; 2,3-diaminopropionic acid (Dpr); α-aminoisobutyric acid (Aib); ε-aminohexanoic acid (Aha); δ-aminovaleric acid (Ava); N-methylglycine or sarcosine (MeGly or Sar); ornithine (Orn); citrulline (Cit); t-butylalanine (Bua); t-butylglycine (Bug); N-methylisoleucine (MeIle); phenylglycine (Phg); cyclohexylalanine (Cha); norleucine (Nle); naphthylalanine (Nal); 2-chlorophenylalanine (Ocf); 3-chlorophenylalanine (Mcf); 4-chlorophenylalanine (Pcf); 2-fluorophenylalanine (Off); 3-fluorophenylalanine (Mff); 4-fluorophenylalanine (Pff); 2-bromophenylalanine (Obf); 3-bromophenylalanine (Mbf); 4-bromophenylalanine (Pbf); 2-methylphenylalanine (Omf); 3-methylphenylalanine (Mmf); 4-methylphenylalanine (Pmf); 2-nitrophenylalanine (Onf); 3-nitrophenylalanine (Mnf); 4-nitrophenylalanine (Pnf); 2-cyanophenylalanine (Ocf); 3-cyanophenylalanine (Mcf); 4-cyanophenylalanine (Pcf); 2-trifluoromethylphenylalanine (Otf); 3-trifluoromethylphenylalanine (Mtf); 4-trifluoromethylphenylalanine (Ptf); 4-aminophenylalanine (Paf); 4-iodophenylalanine (Pif); 4-aminomethylphenylalanine (Pamf); 2,4-dichlorophenylalanine (Opef); 3,4-dichlorophenylalanine (Mpcf); 2,4-difluorophenylalanine (Opff); 3,4-difluorophenylalanine (Mpff); pyrid-2-ylalanine (2pAla); pyrid-3-ylalanine (3pAla); pyrid-4-ylalanine (4pAla); naphth-1-ylalanine (1nAla); naphth-2-ylalanine (2nAla); thiazolylalanine (taAla); benzothienylalanine (bAla); thienylalanine (tAla); furylalanine (fAla); homophenylalanine (hPhe); homotyrosine (hTyr); homotryptophan (hTrp); pentafluorophenylalanine (5ff); styrylkalanine (sAla); authrylalanine (aAla); 3,3-diphenylalanine (Dfa); 3-amino-5-phenypentanoic acid (Afp); penicillamine (Pen); 1,2,3,4-tetrahydroisoquinoline-3-carboxylic acid (Tic); β-2-thienylalanine (Thi); methionine sulfoxide (Mso); N(w)-nitroarginine (nArg); homolysine (hLys); phosphonomethylphenylalanine (pmPhe); phosphoserine (pSer); phosphothreonine (pThr); homoaspartic acid (hAsp); homoglutanic acid (hGlu); 1-aminocyclopent-(2 or 3)-ene-4 carboxylic acid; pipecolic acid (PA), azetidine-3-carboxylic acid (ACA); 1-aminocyclopentane-3-carboxylic acid; allylglycine (aOly); propargylglycine (pgGly); homoalanine (hAla); norvaline (nVal); homoleucine (hLeu), homovaline (hVal); homoisolencine (hIle); homoarginine (hArg); N-acetyl lysine (AcLys); 2,4-diaminobutyric acid (Dbu); 2,3-diaminobutyric acid (Dab); N-methylvaline (MeVal); homocysteine (hCys); homoserine (hSer); hydroxyproline (Hyp) and homoproline (hPro). Additional non-encoded amino acids of which the polypeptides described herein may be comprised will be apparent to those of skill in the art (see, e.g., the various amino acids provided in Fasman, 1989, *CRC Practical Handbook of Biochemistry and Molecular Biology*, CRC Press, Boca Raton, FL, at pp. 3-70 and the references cited therein, all of which are incorporated by reference). These amino acids may be in either the L- or D-configuration.

Those of skill in the art will recognize that amino acids or residues bearing side chain protecting groups may also comprise the polypeptides described herein. Non-limiting examples of such protected amino acids, which in this case belong to the aromatic category, include (protecting groups listed in parentheses), but are not limited to: Arg(tos), Cys(methylbenzyl), Cys(nitropyridinesulfenyl), Glu(δ-benzylester), Gln(xanthyl), Asn(N-δ-xanthyl), His(bom), His (benzyl), His(tos), Lys(fmoc), Lys(tos), Ser(O-benzyl), Thr (O-benzyl) and Tyr(O-benzyl).

Non-encoding amino acids that are conformationally constrained of which the polypeptides described herein may be composed include, but are not limited to, N-methyl amino acids (L-configuration); 1-aminocyclopent-(2 or 3)-ene-4-carboxylic acid; pipecolic acid; azetidine-3-carboxylic acid; homoproline (hPro); and 1-aminocyclopentane-3-carboxylic acid.

C. Polynucleotides Encoding Engineered Polypeptides

In another embodiment, the disclosure provides polynucleotides encoding the engineered ketoreductase enzymes. The polynucleotides may be operatively linked to one or more heterologous control sequences that regulate gene expression to create a recombinant polynucleotide capable of expressing the polypeptide. Expression constructs containing a heterologous polynucleotide encoding the engineered ketoreductase can be introduced into appropriate host cells to express the corresponding ketoreductase polypeptide.

Because of the knowledge of the codons corresponding to the various amino acids, availability of a protein sequence provides a description of all the polynucleotides capable of encoding the subject. The degeneracy of the genetic code, where the same amino acids are encoded by alternative or synonymous codons allows an extremely large number of nucleic acids to be made, all of which encode a ketoreductase enzymes disclosed herein. Thus, having identified a particular amino acid sequence, those skilled in the art could make any number of different nucleic acids by simply modifying the sequence of one or more codons in a way which does not change the amino acid sequence of the protein. In this regard, the disclosure specifically contemplates each and every possible variation of polynucleotides that could be made by selecting combinations based on the possible codon choices, and all such variations are to be considered specifically disclosed for any polypeptide disclosed herein, including the amino acid sequences presented in Table 2. In various embodiments, the codons are selected to fit the host cell in which the protein is being produced. For example, preferred codons used in bacteria are used to express the gene in bacteria; preferred codons used in yeast are used for expression in yeast; and preferred codons used in mammals are used for expression in mammalian cells.

In some embodiments, the polynucleotide comprises a nucleotide sequence encoding a ketoreductase polypeptide comprising an amino acid sequence that has at least about 85%, 86%, 87%, 88%, 89%, 90%, 91%, 92%, 93%, 94%, 95%, 96%, 97%, 98%, or 99% or more sequence identity to any of the reference engineered ketoreductase polypeptides described herein, e.g., any of SEQ ID NO: 4, 6, 8, 10, 12, 14, 16, 18, 20, 22, 24, 26, 28, 30, 32, or 34.

For example, in some embodiments, the polynucleotide comprises a sequence encoding a ketoreductase polypeptide with at least about 85%, 86%, 87%, 88%, 89%, 90%, 91%, 92%, 93%, 94%, 95%, 96%, 97%, 98%, or 99% or more sequence identity to a reference amino acid sequence based on SEQ ID NO:2 having amino acid modifications at T2, I11, A64, T76, V95, S96, V99, E145, F147, V148, T152, L153, S159, Y190, D197, E200, A202, M206, Y249 such as, for example, I11L, A64V, T76I, V95M, S96L, V99L, E145A, F147L, F147I, V148I, T152A, L153M, S159T, Y190C, Y190G, D197A, E200P, A202F, M206C, and Y249F.

In some embodiments, the polynucleotide encodes a ketoreductase polypeptide comprising an amino acid sequence that has at least about 85%, 86%, 87%, 88%, 89%, 90%, 91%, 92%, 93%, 94%, 95%, 96%, 97%, 98%, 99% or more identity as compared to a reference sequence based on SEQ ID NO:2 having at the residue corresponding to I11, A64, T76, S96, V148 a Z1 amino acid; at the residue corresponding to V95, V99, E145, F147, T152, L153, Y190, D197 a Z2 amino acid; at the residue corresponding to A202 and Y249 a Z4 amino acid; at a residue corresponding to S159 a Z5 amino acid; at a residue corresponding to E200 a Z7 amino acid; and at a residue corresponding to M206 a cysteine amino acid; and wherein the polypeptides has ketoreductase activity.

In some embodiments, the polynucleotide encodes a ketoreductase polypeptide comprising an amino acid sequence that has at least about 85%, 86%, 87%, 88%, 89%, 90%, 91%, 92%, 93%, 94%, 95%, 96%, 97%, 98%, 99% or more identity as compared to a reference sequence based on SEQ ID NO:4, 6, 8, 10, 12, 14, 16, 18, 20, 22, 24, 26, 28, 30, 32, or 34, wherein the residues corresponding to T2, I11, A64, T76, V95, S96, V99, A145, L147, V148, T152, L153, S159, C190, D197, E200, A202, M206, Y249 are not substituted and wherein the polypeptide has ketoreductase activity.

In some embodiments, the polynucleotide encodes a ketoreductase polypeptide comprising residue differences in one or more residue positions as compared to the sequence of SEQ ID NO:2 at residue positions corresponding to the following: T2, I11, A64, T76, V95, S96, V99, E145, F147, V148, T152, L153, S159, Y190, D197, E200, A202, M206, Y249. In some embodiments, the residue differences comprise at positions corresponding to I11, A64, T76, S96, V148 a Z1 amino acid; at the residue corresponding to V95, V99, E145, F147, T152, L153, Y190, D197 a Z2 amino acid; at the residue corresponding to A202 and Y249 a Z4 amino acid; at a residue corresponding to S159 a Z5 amino acid; at a residue corresponding to E200 a Z7 amino acid. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40, 1-45, 1-50, 1-55, or 1-60 residue differences at other amino acid residue positions. In some embodiments, the number of differences can be 1, 2, 3, 4, 5, 6, 7, 8, 9, 10, 11, 12, 14, 15, 16, 18, 20, 22, 24, 26, 30, 35, 40, 45, 50, 55, or 60 residue differences at the other amino acid residue positions. In some embodiments, the residue differences at other residue positions comprise conservative mutations.

In some embodiments, the polynucleotide encodes a ketoreductase polypeptide comprising an amino acid sequence comprising SEQ ID NO:2 and having amino acid substitution(s) selected from the group consisting of at positions corresponding to: (i) I11 a Z1 amino acid; (ii) A64 a Z1 amino acid; (iii) T76 a Z1 amino acid; (iv) S96 a Z1 amino acid; (v) V148 a Z1 amino acid; (vi) V95 a Z2 amino acid; (vii) V99 a Z2 amino acid (viii) E145 a Z2 amino acid (ix) F147 a Z2 amino acid (x) T152 a Z2 amino acid; (xi) L153 a Z2 amino acid; (xii) Y190 a Z2 amino acid; (xiii) D197 a Z2 amino acid; (xiv) A202 a Z4 amino acid (xv) Y249 a Z4 amino acid; (xvi) S159 a Z5 amino acid; (xvii) E200 a Z7 amino acid; (xviii) M206 a cysteine; (xix) any combination of the foregoing; and (xx) 2 or 3, 3 or 4, 5 or 6, 7 or 8, 9 or 10, 11 or 12, 13 or 14, 14 or 15, 16 or 17, 2-4, 2-5, 2-6, 2-7, 2-8, 2-9, 2-10, 2-11, 2-12, 2-13, 2-14, 2-15, 2-16, 2-17, or 2-18 combinations of any of the foregoing substitutions. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40, 1-45, 1-50, 1-55, or 1-60 residue differences at other residue positions specifically described above. In some embodiments, the number of differences can be 1, 2, 3, 4, 5, 6, 7, 8, 9, 10, 11, 12, 14, 15, 16, 18, 20, 22, 24, 26, 30, 35, 40, 45, 50, 55, or 60 residue differences at the other residue positions. In some embodiments, the residue differences at other residue positions comprise conservative mutations.

In some embodiments, the engineered ketoreductase polypeptide can comprise an amino acid sequence that is at least about 85%, 86%, 87%, 88%, 89%, 90%, 91%, 92%, 93%, 94%, 95%, 96%, 97%, 98%, 99% identical to a reference amino acid sequence based on SEQ ID NO: 2 having the features described herein for the residues corresponding to T2, I11, A64, T76, V95, S96, V99, E145, F147, V148, T152, L153, S159, Y190, D197, E200, A202, M206, Y249 with the proviso that the engineered ketoreductase polypeptides have at the residues corresponding to T2, I11, A64, T76, V95, S96, V99, E145, F147, V148, T152, L153, S159, Y190, D197, E200, A202, M206, Y249 at least the preceding features (e.g., combination of residue differences found in any one of SEQ ID NO: 4, 6, 8, 10, 12, 14, 16, 18, 20, 22, 24, 26, 28, 30, 32, or 34).

In some embodiments, the polynucleotide encodes a ketoreductase polypeptide comprising a sequence as set forth in SEQ ID NO: 2 but having at least one substitution at a residue corresponding to T2, I11, A64, T76, V95, S96, V99, E145, F147, V148, T152, L153, S159, Y190, D197, E200, A202, M206, or Y249. In specific embodiments, the substitutions comprise T2S, 11L, A64V, T76I, V95M, S96L, V99L, E145A, F147L, F147I, V148I, T152A, L153M, S159T, Y190C, Y190G, D197A, E200P, A202F, M206C, and Y249F.

In some embodiments, the polynucleotides encode an engineered ketoreductase polypeptide comprising an amino acid sequence selected from SEQ ID NO: 4, 6, 8, 10, 12, 14, 16, 18, 20, 22, 24, 26, 28, 30, 32, or 34.

In some embodiments, the polynucleotides encoding the engineered ketoreductases are selected from SEQ ID NO: 5, 7, 9, 11, 13, 15, 17, 19, 21, 23, 25, 27, 29, 31, or 33. In some embodiments, the polynucleotides are capable of hybridizing under highly stringent conditions to a polynucleotide consisting of a sequence selected from SEQ ID NO: 5, 7, 9, 11, 13, 15, 17, 19, 21, 23, 25, 27, 29, 31, or 33, where the polynucleotide that hybridizes under highly stringent conditions encode a functional ketoreductase capable of converting the substrate of structural formula (I) to the product of structural formula (III).

In some embodiments, the polynucleotides encode the polypeptides described herein but have about 80% or more sequence identity, about 85%, 86%, 87%, 88%, 89%, 90%, 91%, 92%, 93%, 94%, 95%, 96%, 97%, 98%, or 99% or more sequence identity at the nucleotide level to a reference polynucleotide encoding the engineered ketoreductase. In some embodiments, the reference polynucleotide is selected from polynucleotide sequences represented by SEQ ID NO: 5, 7, 9, 11, 13, 15, 17, 19, 21, 23, 25, 27, 29, 31, or 33.

An isolated polynucleotide encoding an improved ketoreductase polypeptide may be manipulated in a variety of ways to provide for expression of the polypeptide. In some embodiments, the polynucleotides encoding the engineered ketoreductase polypeptides can be provided as expression vectors where one or more control sequences is present to regulate the expression of the polynucleotides. Control sequences useful with polynucleotides of the present disclosure including among others, promoters, leader sequences, polyadenylation sequences, propeptide sequences, signal peptide sequences, and transcription terminators, are well known in the art of polynucleotide recombination and expression. Manipulation of the isolated polynucleotide prior to its insertion into a vector may be desirable or necessary depending on the expression vector. The techniques for modifying polynucleotides and nucleic acid sequences utilizing recombinant DNA methods are well known in the art. Guidance is provided in Sambrook et al., 2001, Molecular Cloning: A Laboratory Manual, 3$^{rd}$ Ed., Cold Spring Harbor Laboratory Press; and Current Protocols in Molecular Biology, Ausubel. F. ed., Greene Pub. Associates, 1998, updates to 2006.

In some embodiments, the disclosure provides a recombinant expression vector comprising a polynucleotide encoding an engineered ketoreductase polypeptide, and one or more expression regulating regions such as a promoter and a terminator, a replication origin, etc., depending on the type of hosts into which they are to be introduced. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present disclosure may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus), which can be conveniently subjected to recombinant DNA procedures and can bring about the expression of the polynucleotide sequence. The choice of the vector will typically depend on the compatibility of the vector with the host cell into which the vector is to be introduced. The vectors may be linear or closed circular plasmids. Vectors and host cells suitable for use with the polynucleotides encoding engineered ketoreductases of the present disclosure are well-known in the art.

In another embodiment, the disclosure provides a host cell comprising a polynucleotide encoding an improved ketoreductase polypeptide, the polynucleotide being operatively linked to one or more control sequences for expression of the ketoreductase enzyme in the host cell. Host cells for use in expressing the ketoreductase polypeptides encoded by the expression vectors of the disclosure are well known in the art and include, but are not limited to, bacterial cells, such as *E. coli, Lactobacillus, Streptomyces* and *Salmonella typhimurium* cells; fungal cells, such as yeast cells (e.g., *Saccharomyces cerevisiae* or *Pichia pastoris* (ATCC Accession No. 201178)); insect cells such as *Drosophila* S2 and *Spodoptera* Sf9 cells; animal cells such as CHO, COS, BHK, 293, and Bowes melanoma cells; and plant cells. Appropriate culture mediums and growth conditions for the above-described host cells are well known in the art.

Polynucleotides for expression of a ketoreductase may be introduced into cells by various methods known in the art. Techniques include among others, electroporation, biolistic particle bombardment, liposome mediated transfection, calcium chloride transfection, and protoplast fusion. Various methods for introducing polynucleotides into cells will be apparent to the skilled artisan.

An exemplary host cell is *Escherichia coli* W3110. An expression vector can be created by operatively linking a polynucleotide encoding an improved ketoreductase into the plasmid pCK110900 operatively linked to the lac promoter under control of the lacI repressor. The expression vector can also contain the P15a origin of replication and the chloramphenicol resistance gene. Cells containing the subject polynucleotide in *Escherichia coli* W3110 can be isolated by subjecting the cells to chloramphenicol selection.

In some embodiments, to make the improved ketoreductase polynucleotides and polypeptides of the disclosure, the naturally-occurring or wild-type ketoreductase enzyme used as the starting (or "parent") sequence for engineering is obtained (or derived) from *L. kefir*. In some embodiments, the parent polynucleotide sequence is codon optimized to enhance expression of the ketoreductase in a specified host cell.

As an illustration, a parental polynucleotide sequence encoding the wild-type ketoreductase polypeptide of *L. kefir* is constructed from oligonucleotides prepared based upon the ketoreductase sequence available in Genbank database (see, Genbank accession no. AAP94029.1, GI:33112056, incorporated herein by reference). The parental polynucleotide sequence can be codon optimized for expression in *E. coli* and the codon-optimized polynucleotide cloned into an expression vector. Clones expressing the active ketoreductase in *E. coli* can be identified and the genes sequenced to confirm their identity. The codon-optimized polynucleotide sequence can then be further used for engineering a desired activity, stability or a combination thereof.

The engineered ketoreductases can be obtained by subjecting the polynucleotide encoding a naturally occurring ketoreductase to mutagenesis and/or directed evolution methods, as discussed herein and known in the art. An exemplary directed evolution technique useful to make the engineered ketoreductases of the disclosure is mutagenesis and/or DNA shuffling as described in Stemmer et al., 1994, *Proc Natl Acad Sci USA* 91:10747-10751; WO 95/22625; WO 97/0078; WO 97/35966; WO 98/27230; WO 00/42651; WO 01/75767 and U.S. Pat. No. 6,537,746, each of which is hereby incorporated by reference herein. Other directed evolution procedures that can be used include, among others, staggered extension process (StEP), in vitro recombination (Zhao et al., 1998, *Nat. Biotechnol.* 16:258-261), mutagenic PCR (Caldwell et al., 1994, *PCR Methods Appl.* 3:S136-S140), and cassette mutagenesis (Black et al., 1996, *Proc Natl Acad Sci USA* 93:3525-3529).

The clones obtained following mutagenesis treatment are screened for engineered ketoreductases having a desired improved enzyme property. Measuring enzyme activity from the expression libraries can be performed using the standard biochemistry technique of monitoring the rate of decrease of substrate and/or increase in product. Where the improved enzyme property desired is thermal stability, enzyme activity may be measured after subjecting the enzyme preparations to a defined temperature and measuring the amount of enzyme activity remaining after heat treatments. Clones containing a polynucleotide encoding a ketoreductase are then isolated, sequenced to identify the nucleotide sequence changes (if any), and used to express the enzyme in a host cell.

Where the sequence of the engineered polypeptide is known, the polynucleotides encoding the enzyme can be prepared by standard solid-phase methods, according to known synthetic methods. In some embodiments, fragments of up to about 100 bases can be individually synthesized, then joined (e.g., by enzymatic or chemical ligation methods, or polymerase mediated methods) to form any desired continuous sequence. For example, polynucleotides and oligonucleotides of the invention can be prepared by chemical synthesis using, e.g., the classical phosphoramidite method described by Beaucage et al., 1981, *Tet Lett* 22:1859-69, or the method described by Matthes et al., 1984, *EMBO J.* 3:801-05, e.g., as it is typically practiced in automated synthetic methods. According to the phosphoramidite method, oligonucleotides are synthesized, e.g., in an automatic DNA synthesizer, purified, annealed, ligated and cloned in appropriate vectors. In addition, essentially any nucleic acid can be obtained from any of a variety of commercial sources, such as The Great American Gene Company, Ramona, CA, ExpressGen Inc. Chicago, IL, Operon Technologies Inc., Alameda, CA, and many others.

In some embodiments, the present disclosure also provides methods for preparing or manufacturing the non-naturally occurring polypeptides capable of converting compound (2) to compound (1), wherein the methods comprise: (a) culturing a host cell capable of expressing a polynucleotide encoding the non-naturally occurring polypeptide and (b) optionally isolating the polypeptide from the host cell. The non-naturally occurring polypeptides can be expressed in appropriate cells (as described above), and isolated (or recovered) from the host cells and/or the culture medium using any one or more of the well known techniques used for protein purification, including, among others, lysozyme treatment, sonication, filtration, salting-out, ultra-centrifugation, and chromatography. Chromatographic techniques for isolation of the ketoreductase polypeptide include, among others, reverse phase chromatography high performance liquid chromatography, ion exchange chromatography, gel electrophoresis, and affinity chromatography.

In some embodiments, the non-naturally occurring polypeptide of the disclosure can be prepared and used in various isolated forms including but not limited to crude extracts (e.g., cell-free lysates), powders (e.g., shake-flask powders), lyophilizates, and substantially pure preparations (e.g., DSP powders), as further illustrated in the Examples below.

In some embodiments, the non-naturally occurring polypeptide of the disclosure can be prepared and used in purified form. Generally, conditions for purifying a particular enzyme will depend, in part, on factors such as net charge, hydrophobicity, hydrophilicity, molecular weight, molecular shape, etc., and will be apparent to those having skill in the art. To facilitate purification, it is contemplated that in some embodiments the engineered ketoreductase polypeptides of the present disclosure can be expressed as fusion proteins with purification tags, such as His-tags having affinity for metals, or antibody tags for binding to antibodies, e.g., myc epitope tag.

Engineered ketoreductase enzymes expressed in a host cell can be recovered from the cells and or the culture medium using any one or more of the well known techniques for protein purification, including, among others, lysozyme treatment, sonication, filtration, salting-out, ultra-centrifugation, and chromatography. Suitable solutions for lysing and the high efficiency extraction of proteins from bacteria, such as *E. coli*, are commercially available under the trade name CelLytic B™ from Sigma-Aldrich of St. Louis MO.

Chromatographic techniques for isolation of the ketoreductase polypeptide include, among others, reverse phase chromatography high performance liquid chromatography, ion exchange chromatography, gel electrophoresis, and affinity chromatography. Conditions for purifying a particular enzyme will depend, in part, on factors such as net charge, hydrophobicity, hydrophilicity, molecular weight, molecular shape, etc., and will be apparent to those having skill in the art.

In some embodiments, affinity techniques may be used to purify the improved ketoreductase enzymes. For affinity chromatography purification, any antibody which specifically binds the ketoreductase polypeptide may be used. For the production of antibodies, various host animals, including but not limited to rabbits, mice, rats, etc., may be immunized by injection with a ketoreductase polypeptide. The polypeptide may be attached to a suitable carrier, such as BSA, by means of a side chain functional group or linkers attached to a side chain functional group. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacilli Calmette Guerin) and *Corynebacterium parvum*.

D. Methods of Using Engineered Ketoreductase Polypeptides

The engineered ketoreductase polypeptides described herein can be used in processes comprising the conversion of a (1-(3-hydroxyphenyl)-2-(methylamino)ethanone) substrate compound (e.g., compound (2) or compound (2a)) to an (R)-phenylephrine product compound (e.g., compound (1) or compound (1a)) such as shown in Scheme 1 or Scheme 5 (below).

In some embodiments, the disclosure provides processes for preparing an (R)-phenylephrine product compound comprising: contacting an engineered polypeptide of the present disclosure (e.g., as described above and elsewhere herein) with a mixture comprising a 1-(3-hydroxyphenyl)-2-(methylamino)ethanone substrate and a buffer under reaction conditions suitable to convert 1-(3-hydroxyphenyl)-2-(methylamino)ethanone to (R)-phenylephrine.

It is contemplated that any of the engineered polypeptides having ketoreductase activity disclosed herein may be used in the methods. For example, in some embodiments, the methods can be carried out wherein the engineered polypeptide is selected from an amino acid sequence at least about 70%, 75%, 80%, 81%, 82%, 83%, 84%, 85%, 86%, 87%, 88%, 89%, 90%, 91%, 92%, 93%, 94%, 95%, 96%, 97%, 98%, 99% or more identical to SEQ ID NO: 2, which further comprises the combination of residue differences of any one of SEQ ID NO: 4, 6, 8, 10, 12, 14, 16, 18, 20, 22, 24, 26, 28, 30, 32, or 34, as compared to SEQ ID NO: 2. In some embodiments, the any one or more of the polypeptides of SEQ ID NO: 4, 6, 8, 10, 12, 14, 16, 18, 20, 22, 24, 26, 28, 30, 32, or 34 may be used in the methods.

In certain embodiments, the methods for preparing an (R)-phenylephrine product compound can be carried out wherein the 1-(3-hydroxyphenyl)-2-(methylamino)ethanone substrate is selected from compound (2) or compound (2a) (i.e., the hydrosulfate form of compound (2) shown below).

The present disclosure contemplates a range of reaction steps and conditions that can be used in the methods, including but not limited to ranges of pH, temperature, buffer, solvent system, substrate loading, polypeptide loading, NADP cofactor loading, atmosphere, reaction time, and further product extraction and isolation conditions.

In certain embodiments, the methods for preparing (R)-phenylephrine of the present disclosure can be carried out wherein the reaction conditions comprise a pH of about 6.0 to about 7.5 (e.g., about 6.5 to about 7.0, or about 7.0). In some embodiments, the method can be carried out wherein the reaction conditions comprise an initial pH of about 7.0 and then adjusting the initial pH to about 6.75 after about 2 hours. In some embodiments, the method further comprises after completion of the enzymatic reaction the steps of saturating the mixture with salt (e.g., NaCl) and adjusting the pH to 8.0 to 9.0, thereby producing a free base of compound (1). In some embodiments, the method further comprises after completion of the enzymatic reaction the step of extraction of the free base of compound (1) with isopropyl alcohol (IPA). In some embodiments, the method further comprises after completion of the enzymatic reaction the step of acidifying (e.g., with HCl) the IPA extract of the mixture and isolating the (R)-phenylephrine salt (e.g., HCl salt of compound (1a) below).

In some embodiments, the methods for preparing (R)-phenylephrine of the present disclosure can be carried out wherein the mixture comprises at least about 50-400 g/L 1-(3-hydroxyphenyl)-2-(methylamino)ethanone substrate loading (e.g., about 50-100 g/L, about 50-200 g/L, about 50-300 g/L, about 50-400 g/L, about 100 g/L, about 200 g/L, about 300 g/L or about 400 g/L). The values for substrate loadings provided herein are based on the molecular weight of 1-(3-hydroxyphenyl)-2-(methylamino)ethanone (i.e., compound (2)) and contemplates that the equivalent molar amounts of 1-(3-hydroxyphenyl)-2-(methylamino)ethanone hydrosulfate (compound (2a)) also can be used (e.g., 100 g/L of compound (2) equals about 130 g/L of compound (2a)).

In some embodiments, the methods for preparing (R)-phenylephrine of the present disclosure can be carried out wherein the resulting engineered polypeptide concentration in the mixture is about 0.1-1.5 g/L, about 0.5-1.2 g/L, or about 0.7-1.0 g/L.

In certain embodiments, the method can be carried out wherein the reaction conditions comprise a temperature of about 25° C. to about 40° C. In certain embodiments, the temperature during the enzymatic reaction can be maintained at ambient (e.g., 25° C.), 30° C., 35° C., 37° C., 40° C.; or in some embodiments adjusted over a temperature profile during the reaction.

In certain embodiments, the method can be carried out wherein the mixture comprises a solvent comprising a buffer and 50% (v/v) isopropyl alcohol. In some embodiments, the buffer is selected from triethanolamine (e.g., about 0.1 M to about 0.2 M TEA) and potassium phosphate (e.g., about 0.025 M to about 0.10 M phosphate). As shown in the Examples, the method can be carried out using 0.1 M TEA buffer (prepared at pH 6.0) or 0.05 M potassium phosphate buffer (prepared at pH 6.0) with good results. However, the use of phosphate buffer can reduce impurities due to the presence of TEA.

In certain embodiments, the method can be carried out wherein the mixture comprises about 0.03-0.1 g/L NADP (e.g., about 0.05 g/L NADP).

In certain embodiments, the method can be carried out wherein the reaction conditions comprise an inert atmosphere (e.g., $N_2$, Ar, etc.).

Accordingly, in some embodiments, the methods for preparing (R)-phenylephrine of the present disclosure can be carried out using a combination of any of the mixture and reaction conditions disclosed above (and elsewhere herein) e.g., (1) a pH of about 6.75-7.0; (2) a temperature of about 30° C.; (3) about 50% isopropyl alcohol; (4) about 0.05 g/L NADP; (5) about 100 g/L 1-(3-hydroxyphenyl)-2-(methylamino)ethanone; (5) and about 0.7-1.1 g/L of the polypeptide; and (6) $N_2$ atmosphere.

In some embodiments, the method can be carried out wherein the reaction conditions comprise a pH of about 6.75-7.0, a temperature of about 30° C., about 100 g/L of compound (2) (or 130 g/L of the hydrosulfate of compound (2a)), and about 1 g/L of an polypeptide having a sequence as set forth in SEQ ID NO: 4, 6, 8, 10, 12, 14, 16, 18, 20, 22, 24, 26, 28, 30, 32, or 34 in a reaction time of about 19-24 hrs, wherein at least 50%-99% of the substrate is converted to (R)-phenylephrine.

In some embodiments, the enzymatic reaction of the method can be carried at 25° C. to 40° C. for about 8 hours to about 24 hours, at which time from about 50% to 99% of the substrate is converted to product (i.e., reaction is substantially completed or the substrate is depleted).

In some embodiments, the methods of the present disclosure results in production of the (R)-phenylephrine product (e.g., reaction of Scheme 1 or Scheme 5) in an enantiomeric excess of at least 99%, 99.1%, 99.2%, 99.3%, 99.4%, 99.5%, 99.6%, 99.7%, 99.8%, or 99.9%.

The engineered ketoreductase polypeptides described herein can catalyze stereoselective reduction of a range of ketone substrates. In some embodiments, the engineered ketoreductase polypeptides described herein, can be used in a method for the stereoselective conversion of a substrate compound of Formula II to a product compound of Formula I as shown in Scheme 2:

Scheme 2

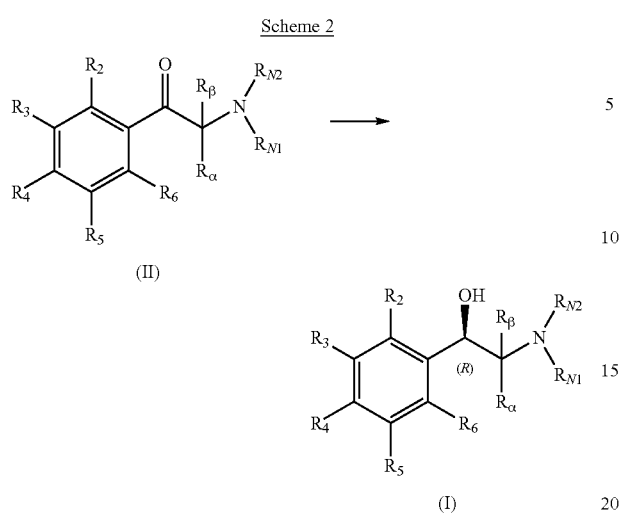

wherein $R_2$ is a group selected from: —H, —Cl, —Br, —I, —F, —CH$_3$, —OH, —OCH$_3$, —SH, —SCH$_3$, —NH$_2$, —NHCH$_3$, or a long chain alkyl; $R_3$ is a group selected from: —H, —Cl, —Br, —I, —F, —CH$_3$, —OH, —OCH$_3$, —SH, —SCH$_3$, —S(O)CH$_3$, —NH$_2$, —NHCH$_3$, —N(CH$_3$)$_2$, —OR, —SR, —NR$_2$, —SO$_2$NR$_2$ (wherein R=—H, —CH$_3$, or alkyl), ethyl, propyl, isopropyl, cyclopropyl, or a long chain alkyl; $R_4$ is a group selected from: —H, —Cl, —Br, —I, —F, —CH$_3$, —OH, —OCH$_3$, —SH, —SCH$_3$, —S(O)CH$_3$, —SO$_2$CH$_3$, —NH$_2$, —NHCH$_3$, —N(CH$_3$)$_2$, SO$_2$NR$_2$ (wherein R=—H, —CH$_3$); $R_5$ is a group selected from: —H, —Cl, —Br, —I, —F, —CH$_3$, —OH, —OCH$_3$, —SH, —SCH$_3$, —S(O)CH$_3$, —SO$_2$CH$_3$, —NH$_2$, —NHCH$_3$, —N(CH$_3$)$_2$, —OR, —SR, —NR$_2$, —SO$_2$NR$_2$ (wherein R=—H, —CH$_3$, or alkyl), ethyl, propyl, isopropyl, or cyclopropyl; $R_6$ is a group selected from: —H, —Cl, —Br, —I, —F, —CH$_3$, —OH, —SH, or —NH$_2$; wherein $R_2$ and $R_3$, $R_3$ and $R_4$, or $R_4$ and $R_5$ can optionally be connected as part of a 5 or 6 membered ring; wherein $R_\alpha$ is a group selected from: —H, —CH$_3$, ethyl, propyl, isopropyl, cyclopropyl, or a long chain alkyl; wherein $R_\beta$ is a group selected from: —H, —CH$_3$, ethyl, propyl, isopropyl, or cyclopropyl; wherein $R_\alpha$ and $R_\beta$ can form a ring, or wherein the $R_\alpha$-$R_\beta$ unit is a carbonyl or imino functional group; wherein $R_{N1}$ and $R_{N2}$ can be independently a group selected from: —H, —CH$_3$, —OH, —OCH$_3$, —OR, —C(O)R (wherein R=—H, —CH$_3$, or alkyl), ethyl, propyl, isopropyl, cyclopropyl, long chain alkyl, carbonyl, or carboxy.

The method for the stereoselective reduction of a substrate of Formula II to a product of Formula I comprises contacting a mixture comprising the compound of Formula II with an engineered ketoreductase polypeptide of the present disclosure under reaction conditions suitable to convert the compound of Formula II to the compound of Formula I. Suitable engineered ketoreductase polypeptides useful with the method comprise an amino acid sequence that is at least 85%, 86%, 87%, 88%, 89%, 90%, 91%, 92%, 93%, 94%, 95%, 96%, 97%, 98%, or 99% identical to a reference amino acid sequence of any one of SEQ ID NO: 4, 6, 8, 10, 12, 14, 16, 18, 20, 22, 24, 26, 28, 30, 32, or 34, wherein the amino acids at the positions of residue differences indicated in Table 4 are unchanged, and the polypeptide has ketoreductase activity.

In certain embodiments of the substrate of Formula II, positions $R_2$ and $R_3$, $R_3$ and $R_4$, or $R_4$ and $R_5$ can optionally be connected as part of a 5 or 6 membered ring. For example, as shown below:

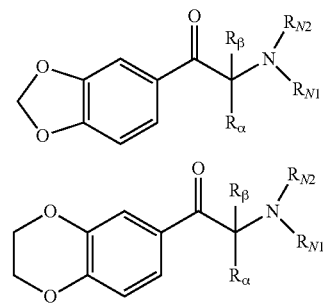

In certain embodiments of the substrate of Formula II, the methylene linker can be substituted with one or two groups ($R_\alpha$ and $R_\beta$). $R_\alpha$ is unrestricted and can include a group extending out of the pocket. $R_\beta$ can be 2 or 3 heavy atoms in size (small alkyl chain, Me, Et, possibly 2-propyl). Also one could connect the two positions in a ring, an example of which is given below, or have the $R_\alpha$-$R_\beta$ unit as a carbonyl or imino function (two structures on the right):

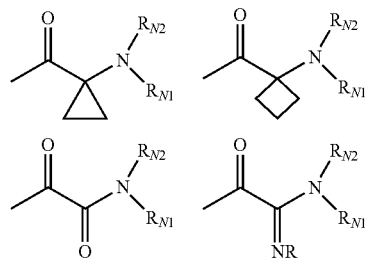

In certain embodiments of the substrate of Formula II, the amine residue is at the pocket limit when bound to a ketoreductase of the disclosure (essentially floating in solution). Accordingly, $R_{N1}$ and $R_{N2}$ can be any group such as, but not limited to, alkyls, carbonyl groups (to give an amide), carboxy groups (e.g., a carbamate), or modified to provide a urea or guanidine. One could also connect the methylene linker to the amine residue to give a 5 or 6 membered ring (e.g., imidazole, thiazole, pyridine and any stable saturated analogues such as oxazine).

Substrate compounds of Formula II can be prepared by standard chemistries or commercially purchased. For example, the substrate of compound (2) is synthesized as set forth in Scheme 3.

Scheme 3

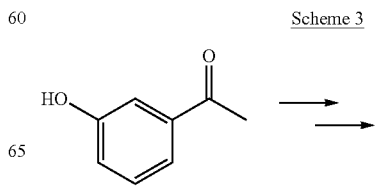

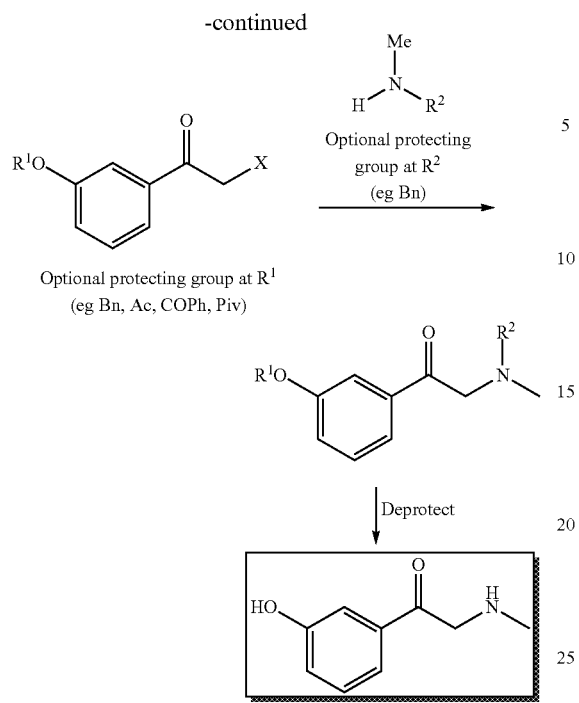

$R^1 = H; X = Br$
$R^1 = Ac, Bz; X = Br$
$R^1 = Ac; X = H$

Accordingly, in a method for the synthesis of (R)-phenylephrine, a step in the method comprises contacting an engineered ketoreductase polypeptide of the present disclosure with: (1) a mixture comprising an α-halo-ketone precursor of phenylephrine; or (2) a mixture comprising 1-(3-hydroxyphenyl)-2-methylaminoethanone.

In some embodiments, the engineered ketoreductases can be used in a method to synthesize analogs of phenylephrine.

Various features and embodiments of the disclosure are illustrated in the following representative examples, which are intended to be illustrative, and not limiting.

8. EXAMPLES

Example 1: Construction of Engineered Ketoreductase Polypeptide Expression Vectors The wild-type ketoreductase gene from *L. kefir* (SEQ ID NO: 1) was designed for expression in *E. coli* using standard codon optimization. (Codon-optimization software is reviewed in e.g., "OPTIMIZER: a web server for optimizing the codon usage of DNA sequences," Puigbò et al., Nucleic Acids Res. 2007 July; 35 (Web Server issue): W126-31. Epub 2007 Apr. 16.) Genes were synthesized using oligonucleotides composed of 42 nucleotides and cloned into expression vector pCK110900 (vector depicted as FIG. 3 in US Patent Application Publication 20060195947, which is hereby incorporated by reference herein) under the control of a lac promoter. The expression vector also contained the P15a origin of replication and the chloramphenicol resistance gene. Resulting plasmids were transformed into *E. coli* W3110 (fhu−) using standard methods. Polynucleotides encoding the engineered ketoreductase polypeptides were also cloned into vector pCK110900 for expression in *E. coli* W3110 or *E. coli* BL21.

Multiple rounds of directed evolution of the codon-optimized *L. kefir* gene were carried out using the gene encoding the most improved polypeptide from each round as the parent "backbone" sequence for the subsequent round of evolution. A polypeptide having a combination of mutations E145A, F147L, and Y190C (SEQ ID NO: 4) was found to increase the activity by at least 10-fold compared to WT and that variant was used as the backbone for the subsequent round of evolution. The resulting engineered ketoreductase polypeptide sequences and specific mutations and relative activities are listed in Table 4.

Example 2: Shake-Flask Procedure for Production of Engineered Ketoreductase Polypeptide Powders A shake-flask procedure is used to generate engineered polypeptide powders used in high-throughput activity assays. A single microbial colony of *E. coli* containing a plasmid encoding an engineered ketoreductase of interest is inoculated into 50 mL Luria Bertani broth containing 30 μg/ml chloramphenicol and 1% glucose. Cells are grown overnight (at least 16 hours) in an incubator at 30° C. with shaking at 250 rpm. The culture is diluted into 250 ml Terrific Broth (12 g/L bacto-tryptone, 24 g/L yeast extract, 4 ml/L glycerol, 65 mM potassium phosphate, pH 7.0, 1 mM MgSO4) containing 30 μg/ml chloramphenicol, in a 1 liter flask to an optical density at 600 nm (OD600) of 0.2 and allowed to grow at 30° C. Expression of the ketoreductase gene is induced by addition of isopropyl-β-D-thiogalactoside ("IPTG") to a final concentration of 1 mM when the OD600 of the culture is 0.6 to 0.8 and incubation is then continued overnight (at least 16 hours).

Cells are harvested by centrifugation (5000 rpm, 15 min, 4° C.) and the supernatant discarded. The cell pellet is resuspended with an equal volume of cold (4° C.) 100 mM triethanolamine (chloride) buffer, pH 7.0 (optionally including 2 mM MgSO$_4$), and harvested by centrifugation as above. The washed cells are resuspended in two volumes of the cold triethanolamine (chloride) buffer and passed through a French Press twice at 12,000 psi while maintained at 4° C. Cell debris is removed by centrifugation (9000 rpm, 45 minutes, 4° C.). The clear lysate supernatant was collected and stored at −20° C. Lyophilization of frozen clear lysate provides a dry shake-flask powder of crude ketoreductase polypeptide. Alternatively, the cell pellet (before or after washing) can be stored at 4° C. or −80° C.

Example 3: High Throughput Activity Assay

This example illustrates a high throughput spectrophotometric assay was carried out in 96-well plate format that is used as a first-tier screen of the relative activity of engineered ketoreductase polypeptides (as in Table 4), and for real-time monitoring of bioprocesses using these polypeptides.

The substrate (hydrosulfate of compound (2)) and NADP were dissolved in buffer, followed by addition of IPA and MgSO$_4$. The pH of the reaction mixture was adjusted to 6.5 with either HCl or NaOH. Cell lysate from a directed evolution sample or a bioprocess sample containing the engineered ketoreductase polypeptide (5-10% of total reaction volume) was then added to the reaction mixture and the reaction was shaken at ambient temperature for 18-20 hrs. Plates also contained negative controls (vector containing beta-lactamase gene) which need to be included in the assay for the calculation of conversion.

The reaction was diluted with 4 volumes of 1:1 MeCN/water mixture and mixed thoroughly to give a total 5-fold dilution. The quenched mixture was centrifuged at 4000 rpm for 10 min. An empty 96 well plate was pre-read on the UV spectrophotometer. A sample of the quenched mixture was then added and diluted with water to give an overall 5-fold dilution (i.e., 40 μL quenched mixture in 160 μL water). The plate was mixed well and then absorbance at 300 nm detected using the UV spectrophotometer. The assay conditions are summarized in Table 5.

TABLE 5

HTP activity assay conditions

| Chemicals/Reagents | Amount |
|---|---|
| Substrate (l-(3-Hydroxyphenyl)-2-methylaminoethanone sulfate) | 10 g/L |
| NADP | 0.1 g/L |
| Buffer (0.1 M TEA.HCl, pH 6.5) | 50% (v/v) |
| IPA | 50% (v/v) |
| MgSO$_4$ | 1 mM |
| Cell lysate Volume | 5-10% |
| Reaction Volume | 200 μL |
| Reaction Temperature | Ambient |
| Reaction time | 18-20 h |

The percentage conversion of the substrate to (R)-phenylephrine product was calculated based on the endpoint value obtained from the UV spectrophotometer as follows:
Percent Conversion=(Mean OD of neg ctrl−OD of sample)/(Mean OD of neg ctrl)*100%.

Example 4: HPLC Assays of Engineered Ketoreductase Activity

This example illustrates four HPLC methods that can be used to monitor and/or analyze products of enzymatic reactions carried out using the engineered ketoreductase polypeptides of the present disclosure.

Method 1 was used as a high throughput (HTP) method to determine percent conversion substrate compound (2) to (R)-phenylephrine product of compound (1). Method 2 was a gradient method for monitoring reactions in chemistry. Method 3 was an accurate method to analyze potency (weight % assay) of (R)-phenylephrine. Method 4 determined the enantiomeric purity of (R)-phenylephrine. The typical working concentration for each of the analytical methods is 100-1000 μg/mL which ensures that the analyses lie within the linear range of the method.

a. Method 1: HTP Method

In the 96-well plates, the reaction mixture was diluted with 4 volumes of 1:1 MeCN/water mixture and mixed thoroughly to give a total dilution of 5-fold (quench procedure). The quenched mixture was centrifuged at 4000 rpm for 10 min, then the samples were added and diluted with mobile phase (0.25% NaOAc, pH 5.0) to give an overall 10-fold dilution (i.e., 20 μL quenched mixture in 180 μL mobile phase). The plates were mixed well and then injected into HPLC. The chromatographic equipment, conditions, and analytical parameters are summarized in Table 7.

TABLE 7

Chromatographic Conditions

| Instrument | Agilent HPLC 1200 series |
|---|---|
| Column | Mightysil Aqua RP18, 250 × 4.6 mm, 5 μm |

TABLE 7-continued

Chromatographic Conditions

| Mobile Phase | 93% (0.25% NaOAc; pH 5.0)/7% MeCN |
|---|---|
| Flow Rate | 1.20 mL/min |
| Column Temperature | 40° C. |
| Wavelength | 275 nm |
| Injection Volume | 10 μL |
| Run time: | 6 min |
| Retention time | Product (3.3 min); Substrate (3.8 min) |

| Item | Analytical Parameter |
|---|---|
| Linearity | R = 1.0 (substrate); Linear Range = 0-817 mg/L |
| | R = 0.99995 (Product); Linear Range = 69.5-400 mg/L |
| LOD | 0.51 mg/L (Product); 0.17 mg/L (Substrate) |
| LOQ | 1.54 mg/L (Product); 0.43 mg/L (Substrate) |

An exemplary chromatogram obtained by this method under isocratic conditions showed a phenylephrine peak at 3.224 min and a slightly broader substrate peak at 3.701 min which is about two-thirds height of the phenylephrine peak.

Using the chromatographic information obtained by this method the % conversion can be calculated as follows:

$$\% \text{ Conversion} = \frac{(\text{Area of Product})}{[(\text{Area of Product}) + (\text{Area of Substrate} \times \text{Response factor})]} \times 100$$

The response factor was tested by injecting a 1:1 mixture of substrate and product solution at 0.5 mg/mL. Then response factor is calculated as the equation below:

$$\text{Response Factor} = \frac{\text{Peak Area of Product}}{\text{Peak Area of Substrate}}$$

b. Method 2: Chemistry Gradient Method

HPLC Sample Preparation: 50 μL of the reaction mixture was taken and dissolved in 0.95 mL of MeCN:water (50:50) mixture. The sample was then centrifuged to remove precipitated enzyme. 50 μL of the supernatant was taken and dissolved in 0.95 mL of mobile phase (0.25% NaOAc, pH 5.0), and injected onto the HPLC. The chromatographic equipment, conditions, and analytical parameters are summarized in Table 8, found in FIG. 1.

A typical chromatogram obtained from this method using 275 nm detection showed a phenylephrine peak at 5.4 min and a substrate peak at 6.4 min which was about one-fourth the height of the phenylephrine peak. LC/MS confirmed that no co-elution was found in the phenylephrine peak.

c. Method 3: Potency Method

A sample of (R)-phenylephrine product (20 mg) was accurately weighed into a 100 mL volumetric flask, and 20 mL of mobile phase was added. The mixture was shaken for 5 min, sonicated for 10 min, and then made up to the 100 mL mark by adding mobile phase. After passing through a 0.5 μm disc membrane, a sample was injected onto the HPLC. The chromatographic equipment, conditions, and analytical parameters are summarized in Table 9.

TABLE 9

| | |
|---|---|
| Chromatographic Conditions | |
| Instrument | Agilent HPLC 1200 series |
| Column | Mightysil Aqua RP18, 250 × 4.6 mm, 5 µm |
| Mobile Phase | 98.5% (0.25% NaOAc; pH 5.5)/1.5% MeCN |
| Flow Rate | 1.0 mL/min |
| Column Temperature | 40° C. |
| Detection Wavelength | 275 nm |
| Injection Volume | 10 µL |
| Run Time | 10 min |
| Retention Time | Substrate: 6.1 min; Phenylephrine: 7.5 min. |
| Item | Analytical Parameters |
| Specificity/Selectivity | No interference of solvents or buffers (0.1% IPA; 5% MeCN; 0.1% acetone; 0.25% NaOAc) with the product and substrate. All analyte peaks are pure according to Diode Array Detector. |
| System Suitability | % RSD of peak area: 1.84; % RSD of retention time: 0.30 (Phenylephrine concentration is 154 mg/L, n = 6) |
| Linearity | R = 0.99995 (Product); Linear Range = 69.5-400 mg/L |
| LOD | 0.51 mg/L, S/N > 3 |
| LOQ | 1.54 mg/L, S/N > 10; % RSD Area = 2.69 (n = 6) |

Using this method the percentage potency can be calculated as follows:

$$\% \text{ Potency} = \frac{\text{Peak Area of Sample} \times \text{Weight of Std} \times \text{Potency of Std}}{\text{Peak Area of Std} \times \text{Weight of Sample}} \times 100$$

A chromatogram obtained using this method showed a phenylephrine peak at about 6.05 min and a substrate peak at about 7.6 min which was broader and about 7-times higher than the phenylephrine peak.

d. Method 4: Chiral Method

HPLC Sample Preparation: 50 µL of the reaction mixture was taken and dissolved in 0.95 mL of 50:50 MeCN/water mixture. The sample was then centrifuged to remove precipitated enzyme. 50 µL of the supernatant was taken and dissolved in 0.95 mL of water, and injected onto the HPLC. The above preparation steps were based on 100 g/L substrate loading. The chromatographic equipment, conditions, and analytical parameters are summarized in Table 10.

TABLE 10

| | |
|---|---|
| Chromatographic Conditions | |
| Instrument | Agilent HPLC 1200 series |
| Column | Regis CBH 4.0 × 100 mm (5 µm) |
| Mobile Phase | 10% MeOH + 90% (8 mM NH$_4$OAc + 13 µM EDTA; pH 5.5) |
| Flow Rate | 0.8 mL/min |
| Column Temperature | Ambient |
| Detection Wavelength | 275 nm |
| Injection Volume | 10 µL |
| Run Time | 5 min |
| Retention Time | R (L): 2.6 min; S(D): 3.2 min |
| Item | Analytical Parameter |
| LOD | 0.11 mg/L, S/N > 3 |
| LOQ | 0.32 mg/L, S/N > 10 |

A typical chromatogram from this method showed a peak at about 2.6 min and a slightly shorter broader peak at about 3.3 min.

Example 5: Process for Enzymatic Synthesis of (R)-Phenylephrine

This example illustrates a process for preparing the (R)-phenylephrine HCl salt (compound (1a)) by contacting a substrate of compound (2a) (the hydrosulfate salt of compound (2)) with an engineered ketoreductase (KRED) polypeptide of the disclosure (e.g., the polypeptides of SEQ ID NO: 4, 6, 8, 10, 12, 14, 16, 18, 20, 22, 24, 26, 28, 30, 32, or 34) to form compound (1), which is then treated HCl and isolated. The hydrosulfate salt of the substrate was more stable to decomposition than the substrate free base under the process conditions. The general reaction for the process is depicted below in Scheme 5.

Scheme 5

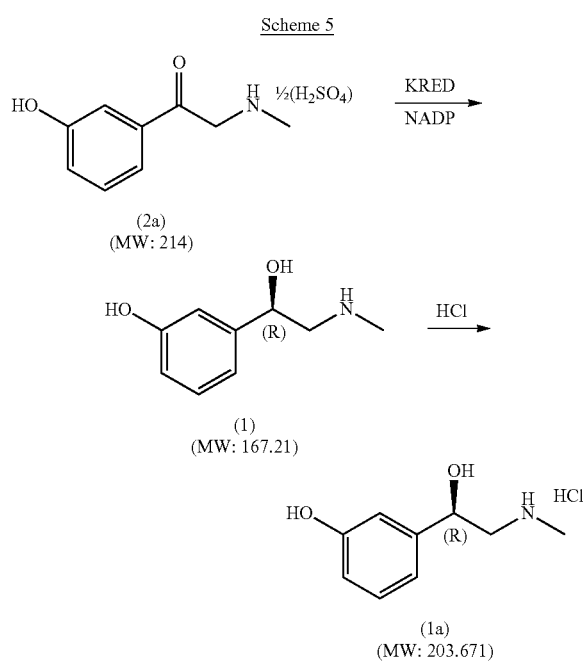

A total of 6.5 g of compound (2a) (the hydrosulfate salt of the substrate—which corresponds to 5.0 g of substrate free base) was added into 44 mL of an aqueous co-solvent solution of 0.1 M TEA buffer (pH 6.0) and 50% isopropyl alcohol (IPA) at 30° C., contained in a 3 neck round bottom flask. (There was little difference between reactions run with 0.1 M and 0.2 M TEA buffer.) After stirring 30 min, the starting pH of 6.0 was adjusted to 7.0, and 2.5 mg of NADP and 50 mg of the ketoreductase polypeptide of SEQ ID NO: 20 (~1.0 g/L) were added to the reaction solution. The pH was maintained at pH 7.0 (or reduced from pH 7.0 to pH 6.75 after 2 h).

After completion of enzymatic reaction (e.g., at 24 h), the reaction mixture was filtered through Celite, washed with 25 mL of MTBE, and saturated with NaCl. The pH was adjusted to 8.0-8.5 to produce the free base form of (R)-phenylephrine (compound (1)) and the IPA (organic layer) was separated from reaction mixture. The aqueous layer was further extracted with 2×20 mL IPA. The combined IPA extracts were concentrated to 0.25 of the volume under the reduced pressure. After acidifying the concentrated IPA extracts with HCl/IPA and standing at 5° C. for 24 h, (R)-phenylephrine HCl salt (compound (1a)) was isolated in ~82-92% yield with ~94-99% purity after filtration.

The effects of pH and temperature on the enzymatic process also were evaluated by running reactions at pH 6.0-7.5 and at temperatures from 25° C.-40° C. with all other parameters kept constant. When carried out at pH 6.0, the enzymatic reaction resulted in 1.3-fold lower conversion of substrate to product than the reactions performed at pH 6.5. Reactions at 25° C. with pH ranging from pH 6.75-7.25 showed similar conversion rates in the range of 81-85%. However, formation of substrate decomposition products increased significantly at 25° C. and pH above 7.25, with ~3.5% and 8.5% decomposition product formed after 24 h reaction at pH 7.3 and 7.45, respectively (~20% of the substrate decomposes in the absence of enzyme after 24 h at pH 7.0, 50% IPA/TEA buffer). Reactions at 30° C. showed >99% substrate conversion to phenylephrine product at pH 6.75-7.0, but reactions at 30° C. and pH 7.25 yielded only 96% conversion with no remaining substrate at 24 h. Reactions at 35° C. resulted in ~4% substrate decomposition at pH 6.75-7.0 with no remaining substrate at 24 h.

Phosphate buffer can also be used in the above enzymatic reaction in order to reduce product contamination is with trace triethanolamine. Instead of 44 mL of 0.1 M of TEA buffer (pH 6.0)/50% IPA, the same amount of 0.05 M of potassium phosphate buffer (pH 6.0)/50% IPA solution is used at 30° C., and the same pH adjustments are carried. The same extraction steps also are used. The phosphate buffered reaction provided >98% conversion after 24 h with only <1.5% substrate decomposition.

The conditions for the process of Example 5 are summarized in Table 6.

TABLE 6

| Exemplary Enzymatic Process Conditions | |
|---|---|
| Substrate Loading | 100 g/L as freebase |
| | 130 g/L as hydrosulfate salt |
| KRED polypeptide (e.g., SEQ ID NO: 20) | 1 g/L |
| NADP | 0.05 g/L |
| Buffer/Solvent System | 0.1 M TEA/50% IPA (pH 6.0) OR |
| | 0.05 M phosphate/50% IPA (pH 6.0) |
| pH profile | Starting pH 6.0, adjust to pH 7.0 (then add enzyme); hold at pH 7.0 for duration of reaction. OR |
| | Starting pH 6.0, adjust to pH 7.0 (then add enzyme); hold at pH 7.0 for 2 h and allow to drop to 6.75, hold at 6.75 until completion. |
| Reaction Temperature | 30° C. |

Example 6: Process for Enzymatic Synthesis of (R)-Phenylephrine at 50 g Scale

This example illustrates a process for preparing the (R)-phenylephrine HCl salt at a 50 g scale using an engineered ketoreductase (KRED) polypeptide of the disclosure. The general reaction for the process was as depicted in Scheme 5 (above). Generally, the reaction was carried out as described for Example 5 with the following differences:

The enzymatic reaction mixture of 500 mL was charged in a three-neck flask and included: 100 g/L of 1-(3-hydroxyphenyl)-2-(methylamino)ethanone substrate (~65 g of compound (2a)), 0.05 g/L NADP, and 1.0 g/L polypeptide of SEQ ID NO: 20, in 0.05 M potassium phosphate buffer (pH 6.0) with 50% IPA (v/v).

The pH of the solution was adjusted to 7.0 and maintained throughout with a pH stat. Temperature was maintained at 30° C. Otherwise the conditions were the same as in Example 5. The reaction was complete (~99% conversion) at 22 h.

After filtering through Celite the reaction mixture was concentrated to ½ volume, washed with MTBE. The mixture was brought back up to 500 mL with IPA and saturated with NaCl. The pH was then adjusted to pH 8.0 to 8.5 and the organic layer allowed to separate and removed. The remaining aqueous layer was extracted 2× with IPA and the extracted organic layers were combined and further concentrated. After addition of MeOH the concentrated organic phase was filtered through Celite then further concentrated. This final organic phase concentrate was then acidified with a solution of HCl/IPA and allowed to crystallize.

Following filtration and drying of the crystals, the process resulted in ~54 g of (R)-phenylephrine-HCl for an overall 91% isolation yield at 97.1-98.8% purity.

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. An engineered polypeptide capable of converting 1-(3-hydroxyphenyl)-2-(methylamino)ethanone to (R)-phenylephrine, wherein the amino acid sequence of the polypeptide has at least 95% identity to SEQ ID NO: 4 and comprises at least one residue difference selected from C190G, A202F, M206C, and Y249F.

2. The engineered polypeptide of claim 1, wherein the polypeptide is capable of stereospecifically converting 1-(3-hydroxyphenyl)-2-(methylamino)ethanone to (R)-phenylephrine in an enantiomeric excess of at least 99%.

3. An engineered polynucleotide encoding the engineered polypeptide of claim 1.

4. A method for producing a compound of Formula I from a compound of Formula II:

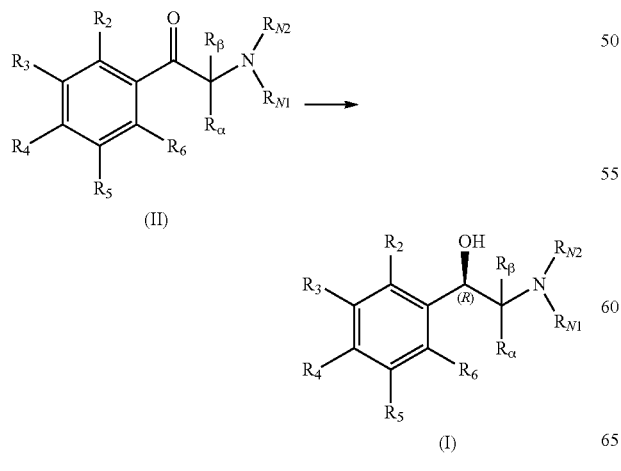

wherein $R_2$ is a group selected from: —H, —Cl, —Br, —I, —F, —$CH_3$, —OH, —$OCH_3$, —SH, —$SCH_3$, —$NH_2$, —$NHCH_3$, or a long chain alkyl;

wherein $R_3$ is a group selected from: —H, —Cl, —Br, —I, —F, —$CH_3$, —OH, —$OCH_3$, —SH, —$SCH_3$, —S(O)$CH_3$, —$NH_2$, —$NHCH_3$, —N($CH_3$)$_2$, —OR, —SR, —$NR_2$, —$SO_2NR_2$ (wherein R=—H, —$CH_3$, or alkyl), ethyl, propyl, isopropyl, cyclopropyl, or a long chain alkyl;

wherein $R_4$ is a group selected from: —H, —Cl, —Br, —I, —F, —$CH_3$, —OH, —$OCH_3$, —SH, —$SCH_3$, —S(O)$CH_3$, —$SO_2CH_3$, —$NH_2$, —$NHCH_3$, —N($CH_3$)$_2$, $SO_2NR_2$ (wherein R=—H, —$CH_3$);

wherein $R_5$ is a group selected from: —H, —Cl, —Br, —I, —F, —$CH_3$, —OH, —$OCH_3$, —SH, —$SCH_3$, —S(O)$CH_3$, —$SO_2CH_3$, —$NH_2$, —$NHCH_3$, —N($CH_3$)$_2$, —OR, —SR, —$NR_2$, —$SO_2NR_2$ (wherein R=—H, —$CH_3$, or alkyl), ethyl, propyl, isopropyl, or cyclopropyl;

wherein $R_6$ is a group selected from: —H, —Cl, —Br, —I, —F, —$CH_3$, —OH, —SH, or —$NH_2$;

wherein $R_2$ and $R_3$, $R_3$ and $R_4$, or $R_4$ and $R_5$ can optionally be connected as part of a 5 or 6 membered ring;

wherein $R_\alpha$ is a group selected from: —H, —$CH_3$, ethyl, propyl, isopropyl, cyclopropyl, or a long chain alkyl;

wherein $R_\beta$ is a group selected from: —H, —$CH_3$, ethyl, propyl, isopropyl, or cyclopropyl;

wherein $R_\alpha$ and $R_\beta$ can form a ring, or wherein the $R_\alpha$-$R_\beta$ unit is a carbonyl or imino functional group;

wherein $R_{N1}$ and $R_{N2}$ can be independently a group selected from: —H, —$CH_3$, —OH, —$OCH_3$, —OR, —C(O)R (wherein R=—H, —$CH_3$, or alkyl), ethyl, propyl, isopropyl, cyclopropyl, long chain alkyl, carbonyl, or carboxy;

the method comprising contacting a mixture comprising the compound of Formula II with a polypeptide of claim 1, under reaction conditions suitable to convert the compound of Formula II to the compound of Formula I.

5. The method of claim 4, comprising:
contacting a polypeptide of claim 1 with a mixture comprising a 1-(3-hydroxyphenyl)-2-(methylamino) ethanone substrate and a buffer under reaction conditions suitable to convert 1-(3-hydroxyphenyl)-2-(methylamino)ethanone to (R)-phenylephrine.

6. The method of claim 4, wherein the reaction conditions comprise a temperature of about 25° C. to about 35° C.

7. The method of claim 4, wherein the reaction conditions comprise a temperature of about 30° C.

8. The method of claim 4, wherein the reaction conditions comprise a pH of about 6.5 to about 7.0.

9. The method of claim 4, wherein the reaction conditions comprise an initial pH of about 7.0 and then adjusting the initial pH to about 6.75 after about 2 hours.

10. The method of claim 4, wherein the mixture comprises 50% isopropyl alcohol.

11. The method of claim 4, wherein the buffer is selected from 0.1 M triethanolamine and 0.05 M potassium phosphate.

12. The method of claim 4, wherein the mixture comprises about 0.05 g/L NADP.

13. The method of claim 4, wherein the reaction conditions comprise an inert atmosphere.

14. The method of claim 4, wherein the reaction conditions comprise a pH of about 6.75-7.0, a temperature of about 30° C., about 50% isopropyl alcohol, about 0.05 g/L NADP, about 100 g/L 1-(3-hydroxyphenyl)-2-(methylamino)ethanone, and about 0.9-1.1 g/L of the polypeptide, wherein the reaction is carried out under $N_2$ for about 19-24 hours.

* * * * *